US012590079B2

(12) United States Patent
Ruppel et al.

(10) Patent No.: US 12,590,079 B2
(45) Date of Patent: Mar. 31, 2026

(54) COMPOUNDS AND USES THEREOF

(71) Applicant: FOGHORN THERAPEUTICS INC., Watertown, MA (US)

(72) Inventors: Sabine K. Ruppel, Cambridge, MA (US); Zhaoxia Yang, Belmont, MA (US); Jason T. Lowe, East Bridgewater, MA (US)

(73) Assignee: FOGHORN THERAPEUTICS INC., Watertown, MA (US)

( * ) Notice: Subject to any disclaimer, the term of this patent is extended or adjusted under 35 U.S.C. 154(b) by 943 days.

(21) Appl. No.: 17/631,791

(22) PCT Filed: Jul. 31, 2020

(86) PCT No.: PCT/US2020/044508
§ 371 (c)(1),
(2) Date: Jan. 31, 2022

(87) PCT Pub. No.: WO2021/022163
PCT Pub. Date: Feb. 4, 2021

(65) Prior Publication Data

US 2022/0289711 A1 Sep. 15, 2022

Related U.S. Application Data

(60) Provisional application No. 62/880,815, filed on Jul. 31, 2019.

(51) Int. Cl.

| | |
|---|---|
| ***C07D 401/14*** | (2006.01) |
| ***C07D 471/04*** | (2006.01) |
| ***C07D 471/10*** | (2006.01) |
| ***C07D 487/04*** | (2006.01) |

(52) U.S. Cl.
CPC ......... *C07D 401/14* (2013.01); *C07D 471/04* (2013.01); *C07D 471/10* (2013.01); *C07D 487/04* (2013.01)

(58) Field of Classification Search
CPC .. C07D 401/14; C07D 471/04; C07D 471/10; C07D 487/04; A61P 35/00
See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 6,352,694 | B1 | 3/2002 | June et al. |
| 6,534,055 | B1 | 3/2003 | June et al. |

(Continued)

FOREIGN PATENT DOCUMENTS

| | | | |
|---|---|---|---|
| CN | 107056772 | A | 8/2017 |
| CN | 108690020 | A | 10/2018 |

(Continued)

OTHER PUBLICATIONS

Al-Hamdany et al., World J Pharm Pharm Sci, 2018, 7:200-211 (Year: 2018).*

(Continued)

*Primary Examiner* — Andrew D Kosar
*Assistant Examiner* — Jonathan D Mahlum
(74) *Attorney, Agent, or Firm* — Clark & Elbing LLP

(57) ABSTRACT

The present disclosure features compounds useful for the treatment of BAF complex-related disorders.

20 Claims, 13 Drawing Sheets

Compound 1

(56) References Cited

U.S. PATENT DOCUMENTS

| | | | |
|---|---|---|---|
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,056,883 | B2 | 6/2006 | Ito et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,205,103 | B2 | 4/2007 | Emerson |
| 7,232,566 | B2 | 6/2007 | June et al. |
| 7,572,631 | B2 | 8/2009 | Berenson et al. |
| 8,476,434 | B2 | 7/2013 | Geuns-Meyer et al. |
| 9,271,978 | B2 | 3/2016 | Liu et al. |
| 9,353,051 | B2 | 5/2016 | Byrd et al. |
| 9,410,943 | B2 | 8/2016 | Kadoch et al. |
| 9,708,338 | B2 | 7/2017 | Yukimasa et al. |
| 9,718,821 | B2 | 8/2017 | Woods et al. |
| 9,908,885 | B2 | 3/2018 | Bennett et al. |
| 9,919,998 | B2 | 3/2018 | Ebright et al. |
| 10,023,592 | B2 | 7/2018 | Boloor |
| 10,047,068 | B2 | 8/2018 | Tojo et al. |
| 10,105,420 | B2 | 10/2018 | Kadoch et al. |
| 10,138,827 | B2 | 11/2018 | Dudar |
| 10,183,009 | B2 | 1/2019 | Albrecht et al. |
| 10,321,345 | B2 | 6/2019 | Kazmi et al. |
| 10,336,722 | B2 | 7/2019 | Bair et al. |
| 10,464,925 | B2 | 11/2019 | Bradner et al. |
| 10,584,101 | B2 | 3/2020 | Crew et al. |
| 10,646,575 | B2 | 5/2020 | Phillips et al. |
| 10,660,968 | B2 | 5/2020 | Phillips et al. |
| 10,725,057 | B2 | 7/2020 | Tojo et al. |
| 10,799,508 | B2 | 10/2020 | Beeharry et al. |
| 10,849,982 | B2 | 12/2020 | Phillips et al. |
| 10,889,593 | B2 | 1/2021 | Chan et al. |
| 10,905,768 | B1 | 2/2021 | Phillips et al. |
| 10,976,320 | B2 | 4/2021 | Dykhuizen et al. |
| 11,185,592 | B2 | 11/2021 | Phillips et al. |
| 11,285,218 | B2 | 3/2022 | Buckley et al. |
| 11,319,318 | B2 | 5/2022 | Martin et al. |
| 11,376,264 | B2 | 7/2022 | Evans et al. |
| 11,402,372 | B2 | 8/2022 | Matyskiela et al. |
| 11,414,416 | B1 | 8/2022 | Ruppel et al. |
| 11,459,335 | B2 | 10/2022 | Phillips et al. |
| 11,560,381 | B1 | 1/2023 | Ruppel et al. |
| 11,584,748 | B2 | 2/2023 | Nasveschuk et al. |
| 11,623,929 | B2 | 4/2023 | Nasveschuk et al. |
| 11,767,330 | B2 | 9/2023 | Gu et al. |
| 11,773,085 | B2 | 10/2023 | Zhou et al. |
| 11,787,800 | B2 | 10/2023 | Ruppel et al. |
| 11,851,445 | B2 | 12/2023 | Ruppel et al. |
| 12,048,747 | B2 | 7/2024 | Phillips et al. |
| 2005/0079512 | A1 | 4/2005 | Emerson et al. |
| 2011/0053897 | A1 | 3/2011 | Che et al. |
| 2011/0061116 | A1 | 3/2011 | Haldar et al. |
| 2016/0058872 | A1 | 3/2016 | Crew et al. |
| 2017/0050968 | A1 * | 2/2017 | Bennett ................ C07D 471/06 |
| 2018/0085465 | A1 | 3/2018 | Bradner et al. |
| 2018/0328913 | A1 | 11/2018 | Kadoch et al. |
| 2019/0076539 | A1 | 3/2019 | Phillips et al. |
| 2020/0206344 | A1 | 7/2020 | Kadoch et al. |
| 2021/0198256 | A1 | 7/2021 | Nasveschuk et al. |
| 2021/0290676 | A1 | 9/2021 | Chaudhary |
| 2021/0388040 | A1 | 12/2021 | Kadoch et al. |
| 2022/0098190 | A1 | 3/2022 | Ruppel et al. |
| 2022/0193205 | A1 | 6/2022 | Zhou et al. |
| 2022/0265618 | A1 | 8/2022 | Malatesta et al. |
| 2022/0289711 | A1 | 9/2022 | Ruppel et al. |
| 2022/0315578 | A1 | 10/2022 | Chen et al. |
| 2023/0065463 | A1 | 3/2023 | Ruppel et al. |
| 2023/0066136 | A1 | 3/2023 | Ruppel et al. |
| 2023/0072053 | A1 | 3/2023 | Ruppel et al. |
| 2023/0077730 | A1 | 3/2023 | Ruppel et al. |
| 2023/0142883 | A1 | 5/2023 | Ruppel et al. |
| 2023/0331722 | A1 | 10/2023 | Ruppel et al. |
| 2023/0416246 | A1 | 12/2023 | Ruppel et al. |
| 2024/0002382 | A1 | 1/2024 | Ruppel et al. |
| 2024/0067642 | A1 | 2/2024 | Ruppel et al. |
| 2024/0150328 | A1 | 5/2024 | Zhou et al. |
| 2024/0150348 | A1 | 5/2024 | Ruppel et al. |
| 2024/0166668 | A1 | 5/2024 | Ruppel et al. |
| 2024/0190894 | A1 | 6/2024 | Gu et al. |
| 2024/0325370 | A1 | 10/2024 | Chen et al. |

FOREIGN PATENT DOCUMENTS

| | | | | | |
|---|---|---|---|---|---|
| JP | H0733773 | A | | 2/1995 | |
| WO | WO-03062392 | A2 | * | 7/2003 | ............. A61P 37/06 |
| WO | WO-2011/014515 | A1 | | 2/2011 | |
| WO | WO-2013/126656 | A1 | | 8/2013 | |
| WO | WO-2016036873 | A1 | * | 3/2016 | ............. A61P 35/00 |
| WO | WO-2016/051187 | A1 | | 4/2016 | |
| WO | WO-2016/133935 | A1 | | 8/2016 | |
| WO | WO-2017/197051 | A1 | | 11/2017 | |
| WO | WO-2017/197056 | A1 | | 11/2017 | |
| WO | WO-2017223452 | A1 | * | 12/2017 | ............. A61P 35/00 |
| WO | WO-2018/102725 | A1 | | 6/2018 | |
| WO | WO-2018/177297 | A1 | | 10/2018 | |
| WO | WO-2019/099868 | A2 | | 5/2019 | |
| WO | WO-2019/152437 | A1 | | 8/2019 | |
| WO | WO-2019/152440 | A1 | | 8/2019 | |
| WO | WO-2019/195201 | A1 | | 10/2019 | |
| WO | WO-2019/207538 | A1 | | 10/2019 | |
| WO | WO-2019195609 | A2 | * | 10/2019 | ............. A61P 35/00 |
| WO | WO-2020/051235 | A1 | | 3/2020 | |
| WO | WO-2020/078933 | A1 | | 4/2020 | |
| WO | WO-2020/132561 | A1 | | 6/2020 | |
| WO | WO-2020/160192 | A1 | | 8/2020 | |
| WO | WO-2020/160193 | A2 | | 8/2020 | |
| WO | WO-2020/160198 | A1 | | 8/2020 | |
| WO | WO-2020/239103 | A1 | | 12/2020 | |
| WO | WO-2020/264177 | A1 | | 12/2020 | |
| WO | WO-2021/055295 | A1 | | 3/2021 | |
| WO | WO-2021155225 | A1 | | 8/2021 | |
| WO | WO-2021/178920 | A1 | | 9/2021 | |
| WO | WO-2023/283263 | A1 | | 1/2023 | |
| WO | WO-2023/039208 | A1 | | 3/2023 | |
| WO | WO-2023/200800 | A1 | | 10/2023 | |
| WO | WO-2024/006292 | A2 | | 1/2024 | |
| WO | WO-2024/013766 | A1 | | 1/2024 | |
| WO | WO-2024/013812 | A1 | | 1/2024 | |
| WO | WO-2024/014021 | A1 | | 1/2024 | |
| WO | WO-2024/037578 | A1 | | 2/2024 | |
| WO | WO-2024/163609 | A1 | | 8/2024 | |
| WO | WO-2024163641 | A2 | | 8/2024 | |
| WO | WO-2024163751 | A1 | | 8/2024 | |
| WO | WO-2025/015149 | A2 | | 1/2025 | |
| WO | WO-2025/015152 | A1 | | 1/2025 | |

OTHER PUBLICATIONS

Bondeson et al., Annu Rev Pharmacol Tolixol, 2017, 57:107-23 (Year: 2017).*

Che et al., Bioorg Med Chem Lett, 2018, 28:2585-2592 (Year: 2018).*

Fligiel et al., Am J Pathol, 1984, 115:418-425 (Year: 1984).*

Bondeson et al., Annu Rev Pharmacol Toxicol, 2017, 57:107-123 (Year: 2017).*

Che et al., Bioor Med Chem Lett, 2018, 28:2585-2592 (Year: 2018).*

Cyrus et al., Chem Med Chem, 2010, 5:979-985 (Year: 2010).*

Lai et al., Nat Rev Drug Discov, 2017, 16:101-114 (Year: 2017).*

Pettersson et al., Drug Disc Today Technol, 2019, 31:15-27 (Year: 2019).*

Steinebach et al., Med Chem Commun, 2019, 10:1037-1041 (Year: 2019).*

Yang et al., Drug Discov Today Technol, 2019, 31:43-51 (Year: 2019).*

(56) References Cited

OTHER PUBLICATIONS

Zoppi et al., J Med Chem, 2019, 62:699-726 (Year: 2019).*
Remillard et al., Angew Chem Int Ed, 2017, 56:5738-5743 (Year: 2017).*
U.S. Appl. No. 17/245,379, Sandoval et al.
U.S. Appl. No. 18/292,508, Huang, Liyue.
"Acute Leukemia," Merck Manual (Online Edition), retrieved Jul. 10, 2013 (6 pages).
Amako et al., "Development and Advances of PROTACs: Induced Protein Degradation by Hijacking Ubiquitin Ligase," Journal of Synthetic Organic Chemistry, Japan 76(4):358-9 (2018). English abstract included.
Baheti et al., "Excipients used in lyophilization of small molecules," J. Excipients and Food Chem. 1(1):41-54 (2010).
Ballatore et al., "Aminothienopyridazine inhibitors of tau aggregation: evaluation of structure-activity relationship leads to selection of candidates with desirable in vivo properties," Bioorg Med Chem. 20(14):4451-61 (Jul. 15, 2012).
Brien et al., "Targeted degradation of BRD9 reverses oncogenic gene expression in synovial sarcoma," eLife. 7:e41305 (Nov. 15, 2018) (26 pages).
Börold et al., "BRD9 is a druggable component of interferon-stimulated gene expression and antiviral activity," EMBO Rep. 22(10):e52823 (Aug. 16, 2021) (18 pages).
Choi et al., "Correlation of computed tomography and positron emission tomography in patients with metastatic gastrointestinal stromal tumor treated at a single institution with imatinib mesylate: proposal of new computed tomography response criteria," J Clin Oncol. 25(13):1753-9 (May 1, 2007).
Crawford et al., "Inhibition of bromodomain-containing protein 9 for the prevention of epigenetically-defined drug resistance," Bioorg Med Chem Lett. 27(15):3534-41(2017).
Croce, "Oncogenes and cancer," N Engl J Med. 358(5):502-11 (Jan. 31, 2008).
Cui et al., "The chromatin-remodeling BAF complex mediates cellular antiviral activities by promoter priming," Mol Cell Biol. 24(10):4476-86 (May 2004).
Extended European Search Report for European Application No. 21748348.6, dated Jan. 4, 2024 (6 pages).
Extended European Search Report for European Patent Application No. 20749033.5, dated Sep. 29, 2022 (5 pages).
Extended European Search Report for European Patent Application No. 20749034.3, issued Jan. 16, 2023 (9 pages).
Gura, "Systems for identifying new drugs are often faulty," Science. 278(5340):1041-2 (1997).
Hay et al., "Design and synthesis of potent and selective inhibitors of BRD7 and BRD9 bromodomains," Med. Chem. Commun. 6:1381-86 (2015).
Hohmann et al., "Sensitivity and engineered resistance of myeloid leukemia cells to BRD9 inhibition," Nat Chem Biol. 12(9): 672-679 (Sep. 2016) (12 pages).
Hu et al., "Genomic characterization of genes encoding histone acetylation modulator proteins identifies therapeutic targets for cancer treatment," Nat Commun. 10(1):733 (Feb. 2019) (17 pages).
International Preliminary Report on Patentability for International Application No. PCT/US2020/015740, issued Jul. 27, 2021 (6 pages).
International Preliminary Report on Patentability for International Application No. PCT/US2020/044508, mailed Feb. 10, 2022 (6 pages).
International Preliminary Report on Patentability for International Application No. PCT/US2022/036252, mailed Dec. 14, 2023 (11 pages).
International Preliminary Report on Patentability for International Patent Application No. PCT/US2020/015741, issued Jul. 27, 2021 (6 pages).
International Preliminary Report on Patentability for International Patent Application No. PCT/US2020/044043, issued Jan. 31, 2023 (7 pages).
International Search Report and Written Opinion for International Application No. PCT/US20/15740, mailed Jun. 26, 2020 (11 pages).
International Search Report and Written Opinion for International Application No. PCT/US20/44043, mailed Nov. 9, 2020 (15 pages).
International Search Report and Written Opinion for International Application No. PCT/US20/44508, mailed Jan. 12, 2021 (9 pages).
International Search Report and Written Opinion for International Application No. PCT/US2020/015741, mailed Jul. 20, 2020 (16 pages).
International Search Report and Written Opinion for International Application No. PCT/US2023/018195, mailed Aug. 31, 2023 (13 pages).
International Search Report and Written Opinion for International Application No. PCT/US21/15630, mailed Apr. 8, 2021 (8 pages).
International Search Report and Written Opinion for International Application No. PCT/US22/36252, mailed Nov. 15, 2022 (15 pages).
International Search Report and Written Opinion for International Application No. PCT/US22/38641, mailed Nov. 17, 2022 (10 pages).
International Search Report and Written Opinion for International Application No. PCT/US22/38668 mailed Jan. 20, 2023 (11 pages).
International Search Report and Written Opinion for International Application No. PCT/US23/26363, mailed Jan. 4, 2024 (15 pages).
International Search Report and Written Opinion for International Application No. PCT/US24/13766, mailed May 3, 2024 (10 pages).
International Search Report and Written Opinion for International Application No. PCT/US24/13812, mailed Jul. 16, 2024 (17 pages).
International Search Report and Written Opinion for International Application No. PCT/US24/14021, mailed Jun. 21, 2024 (15 pages).
International Search Report and Written Opinion for International Patent Application No. PCT/US2022/028511, mailed Aug. 1, 2022 (14 pages).
International Search Report and Written Opinion for International Patent Application No. PCT/US21/15813, mailed Apr. 6, 2021 (24 pages).
Johnson et al., "Relationships between drug activity in NCI preclinical in vitro and in vivo models and early clinical trials," Br J Cancer. 84(10):1424-31 (2001).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Kadoch et al., "Reversible Disruption of mSWI/SNF (BAF) Complexes by the SS18-SSX Oncogenic Fusion in Synovial Sarcoma," Cell. 153(1):71-85 (2013).
Khaminets et al., "Ubiquitin-Dependent and Independent Signals in Selective Autophagy," Trends Cell Biol. 26(1):6-16 (Jan. 2016).
Kotla et al., "Mechanism of action of lenalidomide in hematological malignancies," J Hematol Oncol. 2:36 (Aug. 12, 2009) (10 pages).
Krämer et al., "BRD9 Inhibition, Alone or in Combination with Cytostatic Compounds as a Therapeutic Approach in Rhabdoid Tumors," Int J Mol Sci. 18(7):1537 (Jul. 16, 2017) (12 pages).
Lopez-Girona et al. "Cereblon is a direct protein target for immunomodulatory and anti proliferative activities of lenalidomide and pomalidomide," Leukemia. 26(11):2326-2335 (2012).
Martin et al., "Structure-Based Design of an in Vivo Active Selective BRD9 Inhibitor," J Med Chem. 59(10):4462-75 (2016).
McBride et al., "Disruption of mammalian SWI/SNF and polycomb complexes in human sarcomas: mechanisms and therapeutic opportunities," J Pathol. 244(5): 638-649 (Apr. 2018).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Muscal et al., "Plasma and cerebrospinal fluid pharmacokinetics of thalidomide and lenalidomide in nonhuman primates," Available in PMC Jun. 18, 2013. Published in final edited form as: Cancer Chemother Pharmacol. 69(4):943-7 (Apr. 2012) (10 pages).

(56) References Cited

OTHER PUBLICATIONS

Pan et al., "A major chromatin regulator determines resistance of tumor cells to T cell-mediated killing," Science. 359(6377):770-75 (Jan. 2018) (11 pages).
Partial Supplementary European Search Report for European Application No. 20749034.3, dated Oct. 11, 2022 (12 pages).
PCT/US2024/037567. Filed Jul. 11, 2024.
PCT/US2024/037578. Filed Jul. 11, 2024.
Pearce et al., Chapter 18: Failure modes in anticancer drug discovery and development. *Cancer Drug Design and Discovery*. Stephen Neidle, 424-435 (2008).
Picaud et al., "9H-purine scaffold reveals induced-fit pocket plasticity of the BRD9 bromodomain," J Med Chem. 58(6):2718-36 (2015).
PubChem CID 12097004 "7-Phenyl-5H-furo[3,2-c] pyridin-4-one," created Feb. 7, 2007, retrieved Apr. 28, 2020 (9 pages).
PubChem CID 68310947, "7-Methyl-4-phenyl-2H-isoquinolin-1-one," created Nov. 30, 2012, retrieved Apr. 28, 2020 (8 pages).
Remillard et al., "Degradation of the BAF Complex Factor BRD9 by Heterobifunctional Ligands," Angew Chem Int Ed Engl. 56(21):5738-43 (2017) (7 pages).
Remillard et al., "Degradation of the BAF Complex Factor BRD9 by Heterobifunctional Ligands," available in PMC May 24, 2018, published in final edited form as: Angew Chem Int Ed Engl. 56(21):5738-5743 (2017) (14 pages).
Search Report and Written Opinion for Singaporean Patent Application No. 11202251301D, dated Jan. 10, 2024 (10 Pages).
Simone, "Oncology: Introduction," Cecil Textbook of Medicine, 20th Edition, vol. 1, pp. 1004-1010, (1996) (8 pages).
Supporting Information for Remillard et al., "Degradation of the BAF Complex Factor BRD9 by Heterobifunctional Ligands," Angew Chem Int Ed Engl. 56(21):5738-43 (2017) (43 pages).
Teuscher et al., "A Versatile Method to Determine the Cellular Bioavailability of Small-Molecule Inhibitors," J Med Chem. 60(1): 157-169 (2017).
Theodoulou et al., "Discovery of I-BRD9, a Selective Cell Active Chemical Probe for Bromodomain Containing Protein 9 Inhibition," J Med Chem. 59(4):1425-39 (2015).
Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).
Wang et al., "NMR Fragment Screening Hit Induces Plasticity of BRD7/9 Bromodomains," Chembiochem. 17(15):1456-63 (2016).
Zhu et al., "Targeting BRD9 for Cancer Treatment: A New Strategy," Onco Targets Ther. 13:13191-13200 (Dec. 24, 2020).
Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (Jan. 2019).
International Search Report and Written Opinion for International Patent Application No. PCT/US2024/037567, mailed Dec. 2, 2024 (16 pages).
Dorwald et al., "Side reactions in organic synthesis: A guide to successful design." Weinheim: WILEY-VCH Verlag GmbH & Co. KGaA, (4 pages) (2005).
Merriam-Webster, "Definition of Isomer." obtained from https://www.merriam- webster.com/dictionary/isomer. (7 pages) (Mar. 2025).

* cited by examiner

| | G0+G1 (%) | S (%) | G2+M (%) | Sub G1 (%) |
|---|---|---|---|---|
| **DMSO** | 58.22 | 27.01 | 9.43 | 5.17 |
| **Compound 1 (200 nM)** | 58.9 | 10.3 | 3.95 | 26.61 |
| **Compound 1 (1μM)** | 61.08 | 12.36 | 4.8 | 21.46 |
| **Lenalidomide (200 nM)** | 50.45 | 22.27 | 8.61 | 18.43 |

| | G0+G1 (%) | S (%) | G2+M (%) | Sub G1 (%) |
|---|---|---|---|---|
| **DMSO** | 60.83 | 27.29 | 7.53 | 3.88 |
| **Compound 1 (200 nM)** | 71.9 | 14.06 | 4.76 | 9.1 |
| **Compound 1 (1μM)** | 72.21 | 14.53 | 5.08 | 7.91 |
| **Lenalidomide (200 nM)** | 58.67 | 27.28 | 6.71 | 7.11 |

| | DMSO | Compound 1 (200 nM) | Compound 1 (1μM) | Lenalidomide (200 nM) |
|---|---|---|---|---|
| Early Apoptosis Cell | 6.94 | 18.72 | 20.08 | 21.77 |
| Late Apoptosis Cell | 10.66 | 16.52 | 17.41 | 14.13 |

COMPOUNDS AND USES THEREOF

BACKGROUND

Disorders can be affected by the BAF complex. BRD9 is a component of the BAF complex. The present invention relates to useful compositions and methods for the treatment of BAF complex-related disorders, such as cancer and infection.

SUMMARY

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents that reduce the levels and/or activity of BRD9 may provide new methods for the treatment of disease and disorders, such as cancer and infection. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Additionally, evidence suggests that the BAF complex is involved in cellular antiviral activities. Thus, agents that degrade BRD9 (e.g., compounds) are useful in the treatment of disorders (e.g., cancers or infections) related to BAF, BRD9, and/or SS18-SSX.

The present disclosure features compounds and methods useful for treating BAF-related disorders (e.g., cancer or infection).

In an aspect, the invention features a compound having the structure of Formula I:

A-L-B    Formula I, wherein

B is a degradation moiety,

L is a linker, and

A has the structure of Formula II:

Formula II

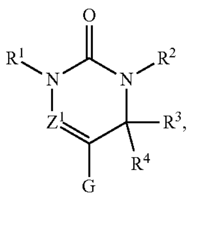

where $R^1$ is, independently, H, optionally substituted $C_1$-$C_6$ alkyl, optionally substituted $C_1$-$C_6$ heteroalkyl, or optionally substituted $C_3$-$C_{10}$ carbocyclyl;

$Z^1$ is $CR^5$ or N;

$R^2$ is, independently, H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted sulfone, or optionally substituted sulfonamide, or $R^2$ and $R^3$ together with the atoms to which each is attached, form an optionally substituted $C_2$-$C_9$ heterocyclyl;

$R^3$ and $R^4$ are, independently, H, halogen, hydroxyl, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, thiol, optionally substituted sulfone, or optionally substituted amino, and/or $R^2$ and $R^3$ together with the atoms to which each is attached, form an optionally substituted $C_2$-$C_9$ heterocyclyl;

$R^5$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and G is

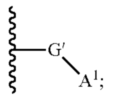

G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and $A^1$ is a bond between A and the linker, or a pharmaceutically acceptable salt thereof.

In some embodiments, $Z^1$ is $CR^5$. In some embodiments, $R^5$ is H. In some embodiments, $R^3$ and $R^4$ are both H.

In some embodiments, $R^1$ is H, optionally substituted $C_1$-$C_6$ alkyl, optionally substituted $C_1$-$C_6$ heteroalkyl, or optionally substituted $C_3$-$C_{10}$ carbocyclyl. In some embodiments, $R^1$ is H, optionally substituted $C_1$-$C_6$ alkyl, optionally substituted $C_2$-$C_6$ alkenyl, or optionally substituted $C_3$-$C_{10}$ carbocyclyl. In some embodiments, $R^1$ is H, optionally substituted $C_1$-$C_6$ alkyl, or optionally substituted $C_3$-$C_{10}$ carbocyclyl.

In some embodiments, optionally substituted $C_1$-$C_6$ alkyl is $C_1$-$C_6$ perfluoroalkyl.

In some embodiments, $R^1$ is H,

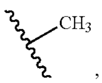 , 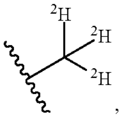 , 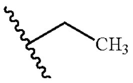 ,

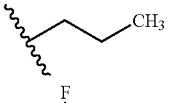 , 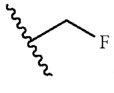 , 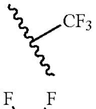 ,

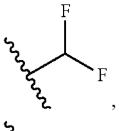 , 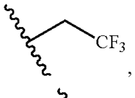 , 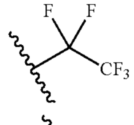 ,

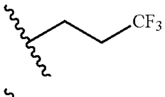 , 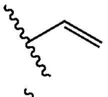 , 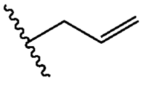 ,

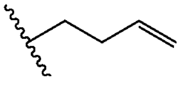 , 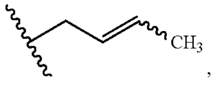 , or

-continued

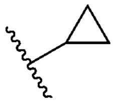

.

In some embodiments, $R^1$ is

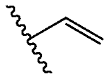, 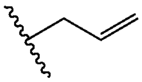, 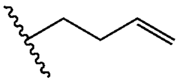,

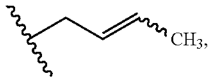, 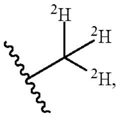, or 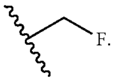.

In some embodiments, $R^1$ is H,

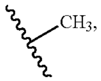, 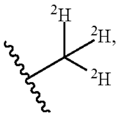, 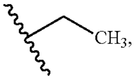,

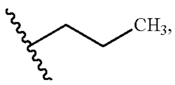, 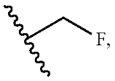, or 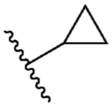.

In some embodiments, $R^1$ is H

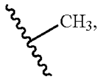, 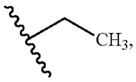, 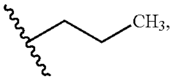,

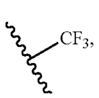, 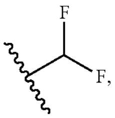, 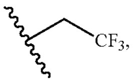, 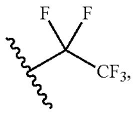,

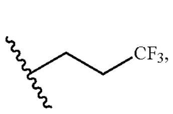, or 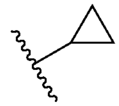.

In some embodiments, $R^1$ is H,

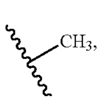, 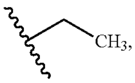, 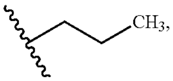, or

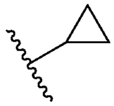

.

In some embodiments, $R^1$ is H,

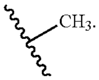

In some embodiments, $R^1$ is H. In some embodiments, $R^1$ is

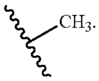

In some embodiments, $R^2$ is optionally substituted $C_1$-$C_6$ alkyl. In some embodiments, the optionally substituted $C_1$-$C_6$ alkyl is methyl.

In some embodiments, G' is optionally substituted $C_3$-$C_{10}$ carbocyclylene or optionally substituted $C_2$-$C_9$ heterocyclylene. In some embodiments, G' is optionally substituted $C_6$-$C_{10}$ arylene or optionally substituted $C_2$-$C_9$ heteroarylene.

In some embodiments, G' is optionally substituted $C_3$-$C_{10}$ carbocyclylene. In some embodiments, G' is optionally substituted $C_6$-$C_{10}$ arylene. In some embodiments, G' is optionally substituted $C_2$-$C_9$ heterocyclylene. In some embodiments, G' is optionally substituted $C_2$-$C_9$ heteroarylene.

In some embodiments, G' is

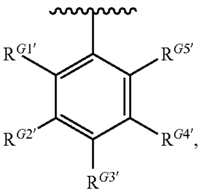

where each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{G1'}$ and $R^{G2'}$, $R^{G2'}$ and $R^{G3'}$, $R^{G3'}$ and $R^{G4'}$, or $R^{G4'}$ and $R^{G5'}$, together with the carbon atoms to which each is attached, combine to form

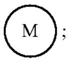;

and

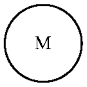

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G1'}$, $R^{G2'}$, $R^{G3'}$, $R^{G4'}$, and $R^{G5'}$ is $A^1$; or

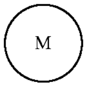

is substituted with $A^1$.

In some embodiments, each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{G1}$ and $R^{G2}$, $R^{G2}$ and $R^{G3}$, $R^{G3}$ and $R^{G4}$ and/or $R^{G4}$ and $R^{G5}$, together with the carbon atoms to which each is attached, combine to form

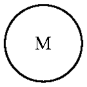

and

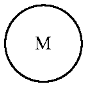

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, In some embodiments, each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, or optionally substituted —O—$C_3$-$C_6$ carbocyclyl; or $R^{G1}$ and $R^{G2}$, $R^{G2}$ and $R^{G3}$, $R^{G3}$ and $R^{G4}$, and/or $R^{G4}$ and $R^{G5}$, together with the carbon atoms to which each is attached, combine to form

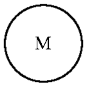

and

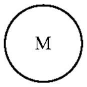

is optionally substituted $C_2$-$C_9$ heteroaryl or optionally substituted $C_2$-$C_9$ heterocyclyl, any of which is optionally substituted with $A^1$.

In some embodiments, each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, or optionally substituted —O—$C_3$-$C_6$ carbocyclyl.

In some embodiments, each of $R^{G1'}$, $R^{G2'}$, $R^{G3'}$, $R^{G4'}$, and $R^{G5'}$ is, independently, H, $A^1$, F, Cl,

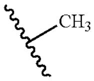, 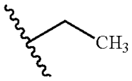, 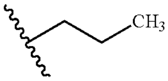,

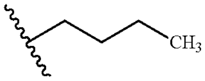, 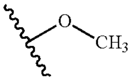,

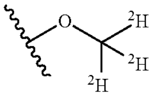, 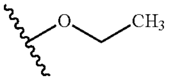,

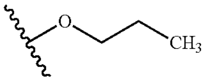, 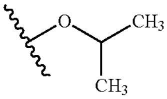,

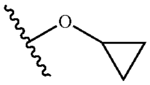, 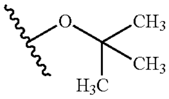, 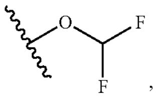,

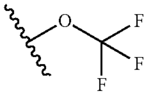, 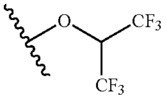,

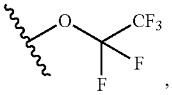, 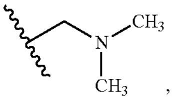,

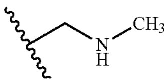, 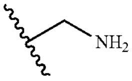, 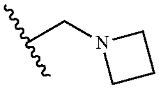,

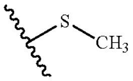, or 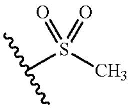.

In some embodiments, each of $R^{G1'}$, $R^{G2'}$, $R^{G3'}$, $R^{G4'}$, and $R^{G5'}$ is, independently, H, A, F,

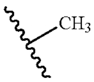, 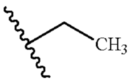, 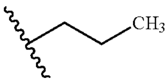,

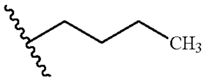, 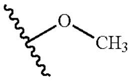,

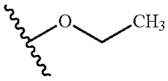, 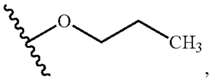,

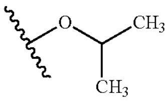, 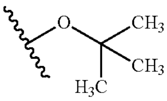,

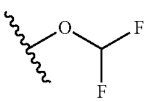, 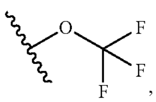, 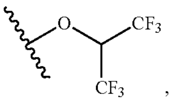,

-continued

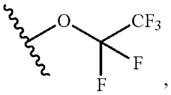 , 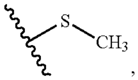 , or 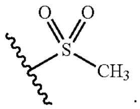 .

In some embodiments, each of $R^{G1'}$, $R^{G2'}$, $R^{G3'}$, $R^{G4'}$, and $R^{G5'}$ is, independently, H, $A^1$, F, Cl,

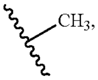 , 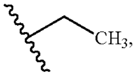 , 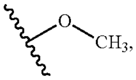 ,

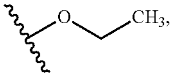 , 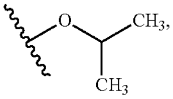 , or

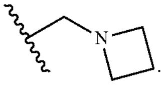 .

In some embodiments,

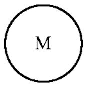

is optionally substituted $C_2$-$C_9$ heteroaryl or optionally substituted $C_2$-$C_9$ heterocyclyl, any of which is optionally substituted with $A^1$.

In some embodiments, G' is

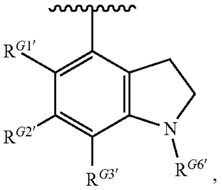 , 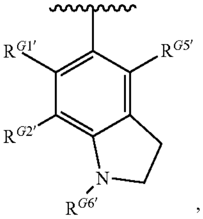 ,

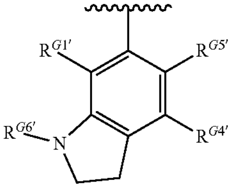 , 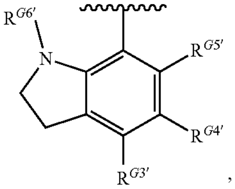 ,

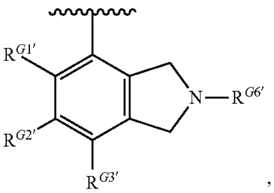 , 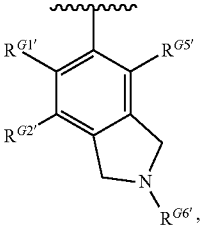 ,

-continued

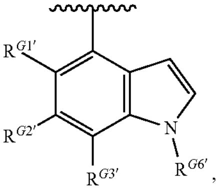 , 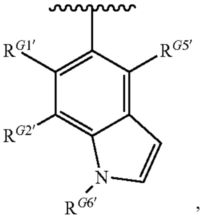 ,

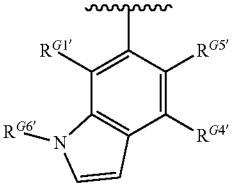 , or 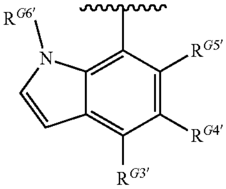 , where $R^{G6'}$ is H, $A^1$, or optionally substituted $C_1$-$C_6$ alkyl.

In some embodiments, $R^{G6'}$ is H, $A^1$,

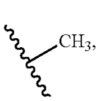 , 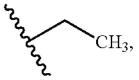 ,

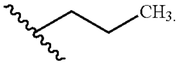 .

In some embodiments, $R^{G6'}$ is H, $A^1$, or

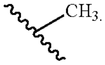 .

In some embodiments, $R^{G6'}$ is H or $A^1$.

In some embodiments, $R^{G6'}$ is $A^1$.

In some embodiments, $R^{G1'}$ is H, $A^1$, F,

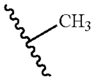 , 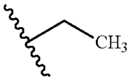 , 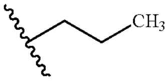 ,

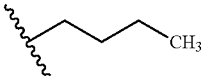 , 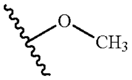 ,

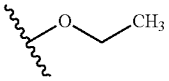 , 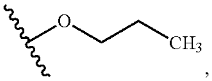 ,

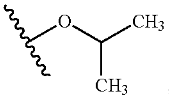 , 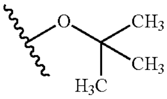 ,

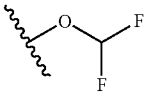 , 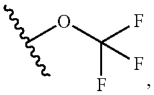 , 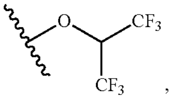 ,

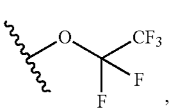 , 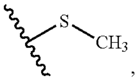 , or 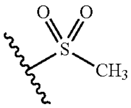 .

In some embodiments, $R^{G2\prime}$ is H, $A^1$, F,

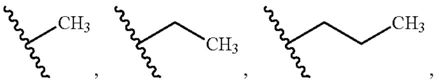
, , ,
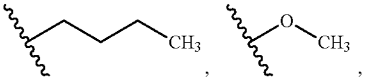
, ,
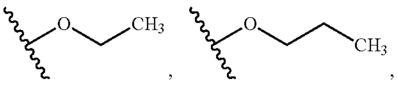
, ,
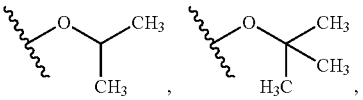
, ,
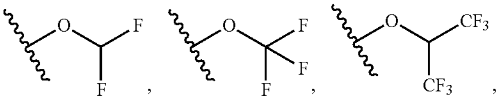
, , ,
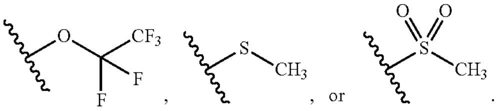
, , or .

In some embodiments, $R^{G3\prime}$ is H, $A^1$, F,

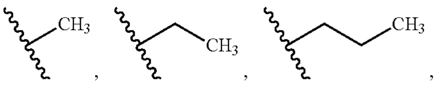
, , ,
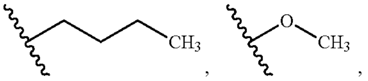
, ,
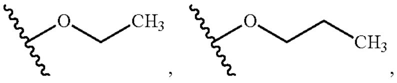
, ,
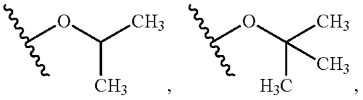
, ,
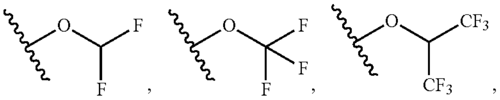
, , ,
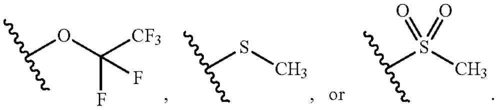
, , or .

In some embodiments, $R^{G4\prime}$ is H, $A^1$, F,

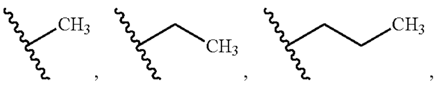
, , ,
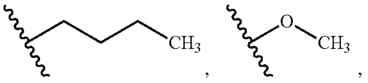
, ,
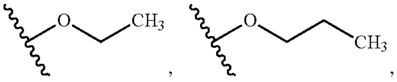
, ,

-continued

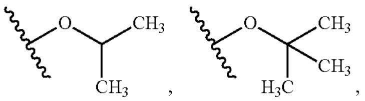
, ,
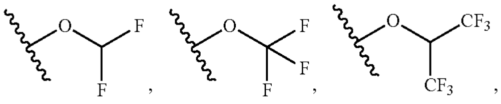
, , ,
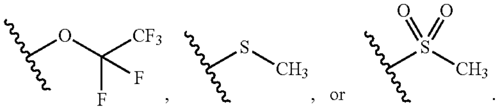
, , or .

In some embodiments, $R^{G5\prime}$ is H, $A^1$, F,

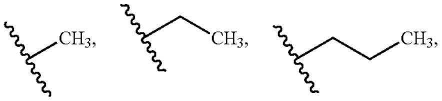
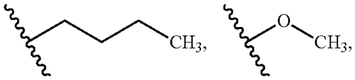
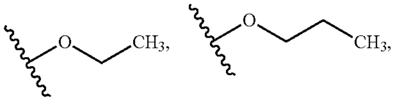
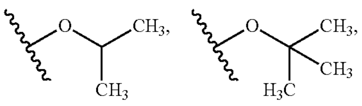
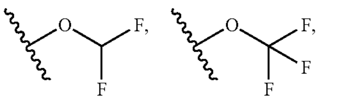
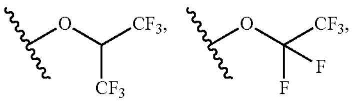
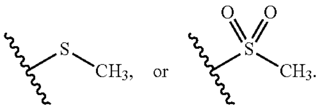
or In some embodiments, one or more of $R^{G1\prime}$, $R^{G2\prime}$, $R^{G3\prime}$, $R^{G4\prime}$, and $R^{G5\prime}$ is H. In some embodiments, two or more of $R^{G1\prime}$, $R^{G2\prime}$, $R^{G3\prime}$, $R^{G4\prime}$, and $R^{G5\prime}$ is H. In some embodiments, three or more of $R^{G1\prime}$, $R^{G2}$, $R^{G3\prime}$, $R^{G4\prime}$, and $R^{G5\prime}$ is H.

In some embodiments, $R^{G1\prime}$ is $A^1$. In some embodiments, $R^{G2\prime}$ is $A^1$. In some embodiments, $R^{G3\prime}$ is $A^1$. In some embodiments, $R^{G4\prime}$ is $A^1$. In some embodiments, $R^{G5\prime}$ is $A^1$. In some embodiments,

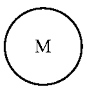

is substituted with $A^1$.

In some embodiments, G is

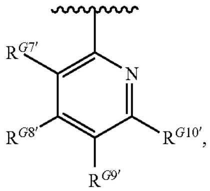

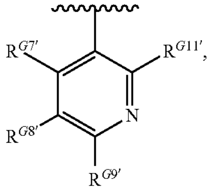

or

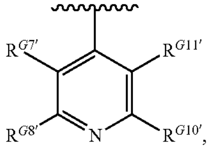

where each of $R^{G7'}$, $R^{G8'}$, $R^{G9'}$, $R^{G10'}$, and $R^{G11'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{G7}$ and $R^{G8}$, $R^{G8}$ and $R^{G9}$, $R^{G9}$ and $R^{G10}$, and/or $R^{G10}$ and $R^{G11}$, together with the carbon atoms to which each is attached, combine to form

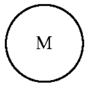

and

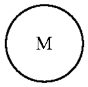

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^1$, where one of $R^{G7'}$, $R^{G8'}$, $R^{G9'}$, $R^{G10'}$, and $R^{G11'}$ is $A^1$; or

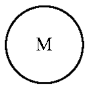

is substituted with $A^1$.

In some embodiments, each of $R^{G7'}$, $R^{G8'}$, $R^{G9'}$, $R^{G10'}$, and $R^{G11'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{G7}$ and $R^{G8}$, $R^{G8}$ and $R^{G9}$, $R^{G9}$ and $R^{G10}$, and/or $R^{G10}$ and $R^{G11}$, together with the carbon atoms to which each is attached, combine to form

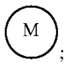

;

and

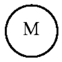

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^1$, where one of $R^{G7'}$, $R^{G8'}$, $R^{G9'}$, $R^{G10'}$, and $R^{G11'}$ is $A^1$; or

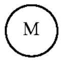

is substituted with $A^1$.

In some embodiments, G is

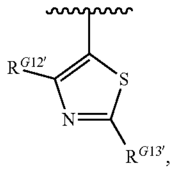

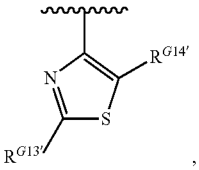

, or

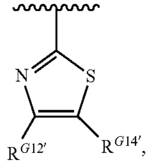

where each of $R^{G12'}$, $R^{G13'}$, and $R^{G14'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{G12}$ and $R^{G14}$ together with the carbon atoms to which each is attached, combine to form

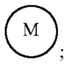

;

and

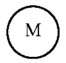

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G12'}$, $R^{G13'}$, and $R^{G14'}$ is $A^1$; or

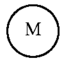

is substituted with $A^1$.

In some embodiments, each of $R^{G12'}$, $R^{G13'}$, and $R^{G14'}$ is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{G12}$, $R^{G14}$ together with the carbon atoms to which each is attached, combine to form

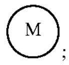;

and

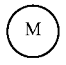

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, where one of $R^{G12'}$, $R^{G13'}$, and $R^{G14'}$ is $A^1$; or

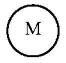

is substituted with $A^1$.

In some embodiments, A has the structure of Formula IIa:

Formula IIa

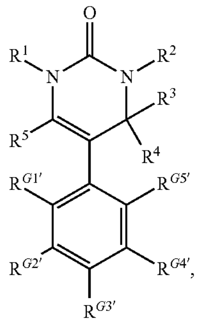

or a pharmaceutically acceptable salt thereof.

In some embodiments, A has the structure of Formula IIb:

Formula IIb

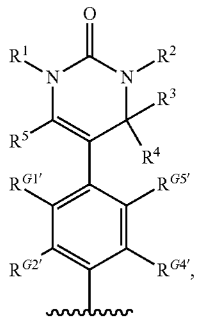

or a pharmaceutically acceptable salt thereof.

In some embodiments, A has the structure of Formula IIc:

Formula IIc

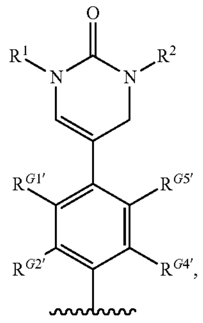

or a pharmaceutically acceptable salt thereof.

In some embodiments, the degradation moiety is a ubiquitin ligase binding moiety.

In some embodiments, the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

In some embodiments, the degradation moiety includes the structure of Formula AA:

Formula AA

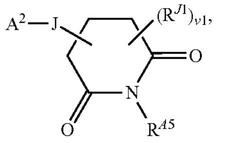

where $A^2$ is a bond between B and the linker;

v1 is 0, 1, 2, 3, 4, or 5;

$R^{5A}$ is H, optionally substituted $C_1$-$C_6$ alkyl, or optionally substituted $C_1$-$C_6$ heteroalkyl;

each $R^{J1}$ is, independently, halogen, optionally substituted $C_1$-$C_6$ alkyl, or optionally substituted $C_1$-$C_6$ heteroalkyl; and J is absent, optionally substituted $C_3$-$C_{10}$ carbocyclylene, optionally substituted $C_6$-$C_{10}$ arylene, optionally substituted $C_2$-$C_9$ heterocyclylene, or optionally substituted $C_2$-$C_9$ heteroarylene, or a pharmaceutically acceptable salt thereof.

In some embodiments, v1 is 0, 1, 2, or 3. In some embodiments, v1 is 0. In some embodiments, v1 is 1. In some embodiments, v1 is 2. In some embodiments, v1 is 3.

In some embodiments, the structure of Formula AA has the structure of

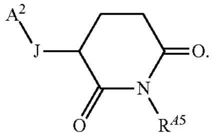

In some embodiments, J is absent. In some embodiments, the structure of Formula AA has the structure of

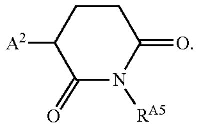

In some embodiments, J is optionally substituted $C_2$-$C_9$ heterocyclylene or optionally substituted $C_2$-$C_9$ heteroarylene.

In some embodiments, J is optionally substituted heterocyclylene.

In some embodiments, the structure of Formula AA has the structure of

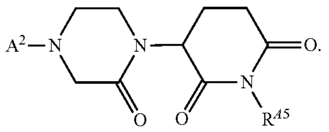

In some embodiments, $R^{A5}$ is H or optionally substituted $C_1$-$C_6$ alkyl. In some embodiments, $R^{A5}$ is H or methyl. In some embodiments, $R^{A5}$ is H. In some embodiments, $R^{A5}$ is methyl.

In some embodiments, the structure of Formula AA has the structure of Formula A:

Formula A

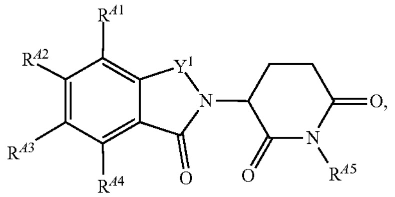

where $Y^1$ is

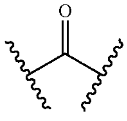, 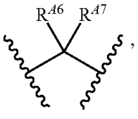, or 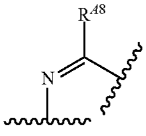;

$R^{A5}$ is H, optionally substituted $C_1$-$C_6$ alkyl, or optionally substituted $C_1$-$C_6$ heteroalkyl;

$R^{A6}$ is H or optionally substituted $C_1$-$C_6$ alkyl; and $R^{A7}$ is H or optionally substituted $C_1$-$C_6$ alkyl; or $R^{A6}$ and $R^{A7}$, together with the carbon atom to which each is bound, form an optionally substituted $C_3$-$C_6$ carbocyclyl or optionally substituted $C_2$-$C_5$ heterocyclyl; or $R^{A6}$ and $R^{A7}$, together with the carbon atom to which each is bound, form an optionally substituted $C_3$-$C_6$ carbocyclyl or optionally substituted $C_2$-$C_5$ heterocyclyl;

$R^{A8}$ is H, optionally substituted $C_1$-$C_6$ alkyl, or optionally substituted $C_1$-$C_6$ heteroalkyl;

each of $R^{A1}$, $R^{S2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

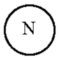;

and

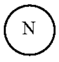

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$; or

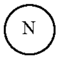

is substituted with $A^2$, or a pharmaceutically acceptable salt thereof.

In some embodiments, each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

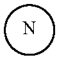;

and

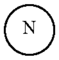

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, In some embodiments, each of $R^{A1}$, $R^{A2}$, $R^{A3}$, and $R^{A4}$ is, H, $A^2$, halogen, optionally substituted $C_1$-$C_6$ alkyl, optionally substituted $C_1$-$C_6$ heteroalkyl, optionally substituted —O—$C_3$-$C_6$ carbocyclyl, hydroxyl, optionally substituted amino; or $R^{A1}$ and $R^{A2}$, $R^{A2}$ and $R^{A3}$, or $R^{A3}$ and $R^{A4}$, together with the carbon atoms to which each is attached, combine to form

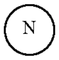; and 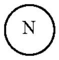

is optionally substituted $C_2$-$C_9$ heterocyclyl, which is optionally substituted with $A^2$, where one of $R^{A1}$, $R^{A2}$, $R^{A3}$, and $R^{A4}$ is $A^2$; or

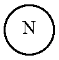

is substituted with $A^2$.

In some embodiments, each of $R^{A1}$, $R^{A2}$, $R^{A3}$, and $R^{A4}$ is, independently, H, $A^2$, F,

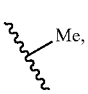, 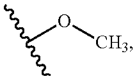, 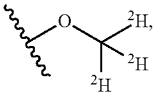, or

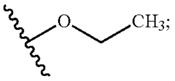;

or $R^{A1}$ and $R^{A2}$, $R^{A2}$ and $R^{A3}$, or $R^{A3}$ and $R^{A4}$, together with the carbon atoms to which each is attached, combine to form

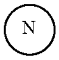; and 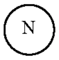

is optionally substituted $C_2$-$C_9$ heterocyclyl, which is optionally substituted with $A^2$, where one of $R^{A1}$, $R^{A2}$, $R^{A3}$, and $R^{A4}$ is $A^2$; or

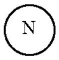

is substituted with $A^2$.

In some embodiments, $R^{A1}$ is $A^2$. In some embodiments, $R^{A2}$ is $A^2$. In some embodiments, $R^{A3}$ is $A^2$. In some embodiments, $R^{A4}$ is $A^2$. In some embodiments, $R^{A5}$ is $A^2$.

In some embodiments, $R^{A5}$ is H or optionally substituted $C_1$-$C_6$ alkyl.

In some embodiments, $R^{A5}$ is H or

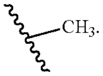.

In some embodiments, $R^{A5}$ is H. In some embodiments, $R^{A5}$ is

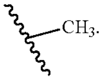.

In some embodiments, $Y^1$ is

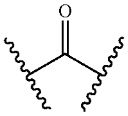 or 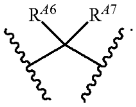.

In some embodiments, $Y^1$ is

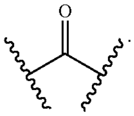 [SMILES: *C(*)=O].

In some embodiments, $Y^1$ is

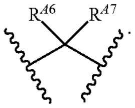.

In some embodiments, each of $R^{A6}$ and $R^{A7}$ is, independently, H, F

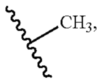, 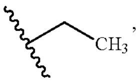, or 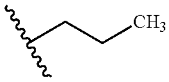;

or $R^{A6}$ and $R^{A7}$, together with the carbon atom to which each is bound, form

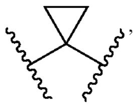, 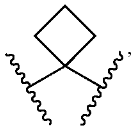, 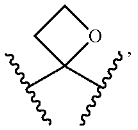, or 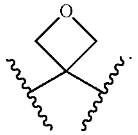.

In some embodiments, $Y^1$ is

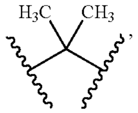, 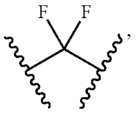,

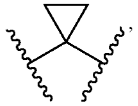, 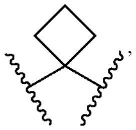, 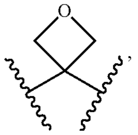, or

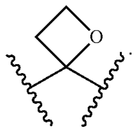.

In some embodiments, the structure of Formula A has the structure of Formula A1:

Formula A1

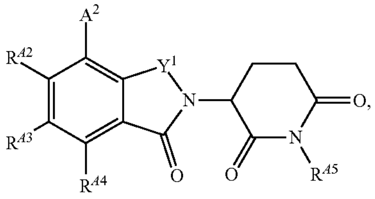

or a pharmaceutically acceptable salt thereof.

In some embodiments, the structure of Formula A has the structure of Formula A2:

Formula A2

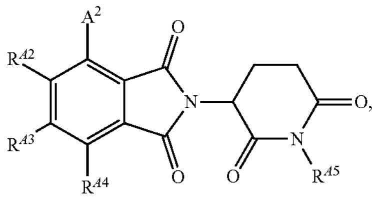

or a pharmaceutically acceptable salt thereof.

In some embodiments, the structure of Formula A has the structure of Formula A3:

Formula A3

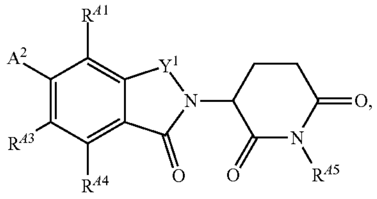

or a pharmaceutically acceptable salt thereof.

In some embodiments, the structure of Formula A has the structure of Formula A4:

Formula A4

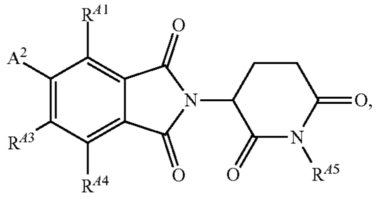

or a pharmaceutically acceptable salt thereof.

In some embodiments, the structure of Formula A has the structure of Formula A5:

Formula A5

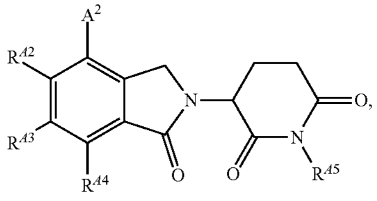

or a pharmaceutically acceptable salt thereof.

In some embodiments, the structure of Formula A has the structure of Formula A6:

Formula A6

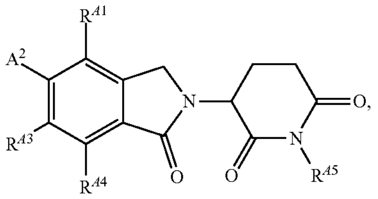

or a pharmaceutically acceptable salt thereof.

In some embodiments, the structure of Formula A has the structure of Formula A7:

Formula A7

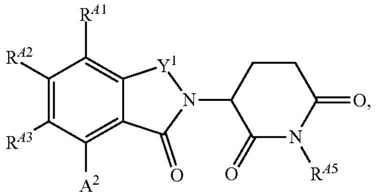

or a pharmaceutically acceptable salt thereof.

In some embodiments, the structure of Formula A has the structure of Formula A8:

Formula A8

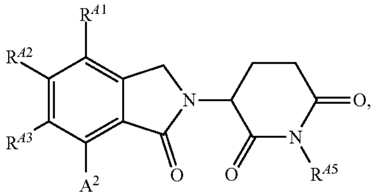

or a pharmaceutically acceptable salt thereof.

In some embodiments, the structure of Formula A has the structure of Formula A9:

Formula A9

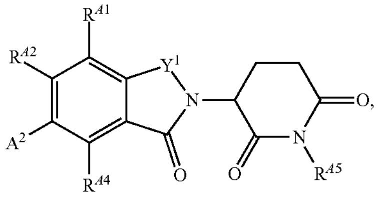

or a pharmaceutically acceptable salt thereof.

In some embodiments, the structure of Formula A has the structure of Formula A10:

Formula A10

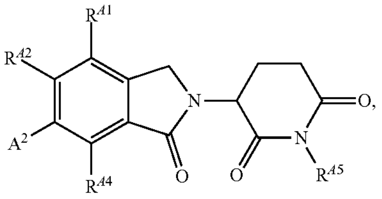

or a pharmaceutically acceptable salt thereof.

In some embodiments, wherein the structure of Formula A is

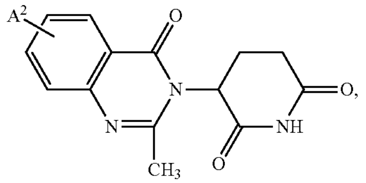

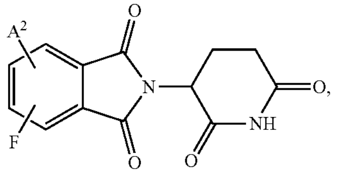

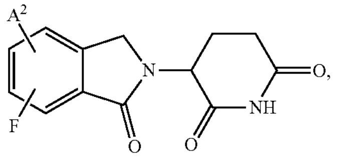

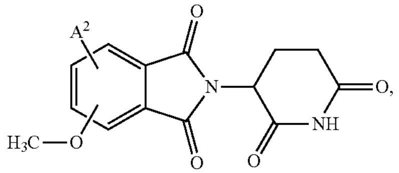

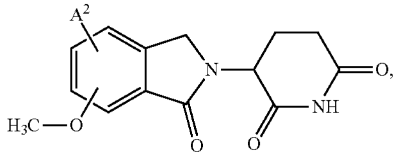

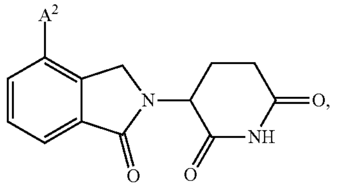

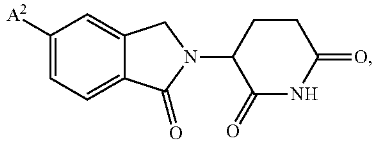

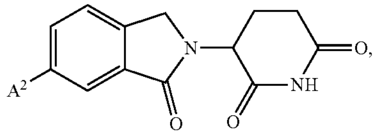

-continued

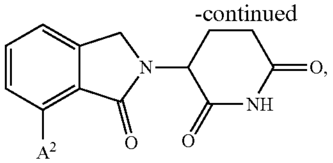

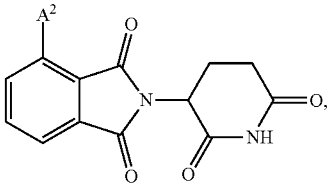

or

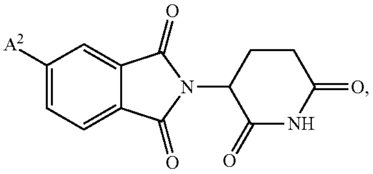

or derivative or analog thereof.

In some embodiments, the structure of Formula A

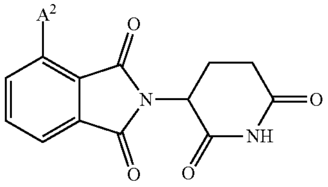

or

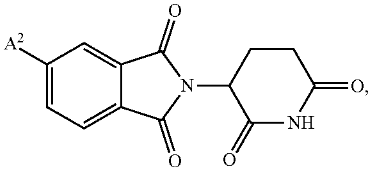

or derivative or analog thereof.

In some embodiments,

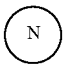

is

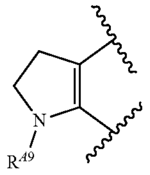

or

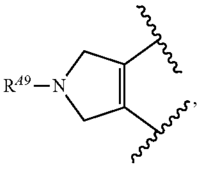

where $R^{A9}$ is H, $A^2$, optionally substituted $C_1$-$C_6$ alkyl, or optionally substituted $C_1$-$C_6$ heteroalkyl.

In some embodiments, the structure of Formula A is

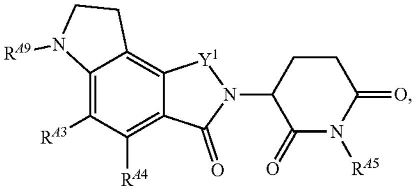

-continued

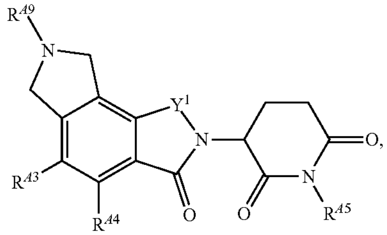

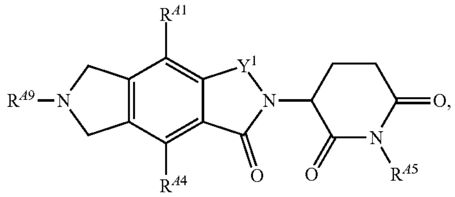

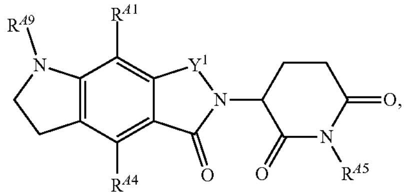

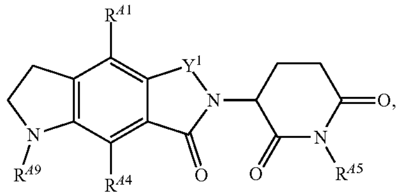

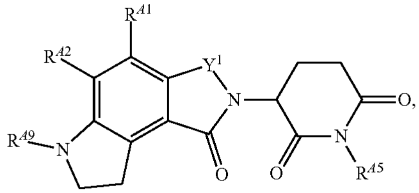

or

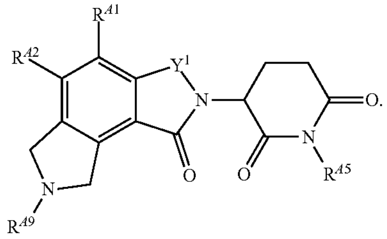

In some embodiments, $R^{A9}$ is H, $A^2$, or optionally substituted $C_1$-$C_6$ alkyl. In some embodiments, $R^{A9}$ is H, $A^2$, or methyl. In some embodiments, $R^{9A}$ is H. In some embodiments, $R^{9A}$ is methyl. In some embodiments, $R^{A9}$ is $A^2$.

In some embodiments, the structure of Formula A is

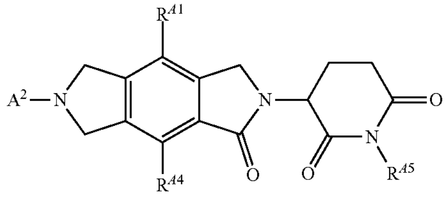

or

-continued

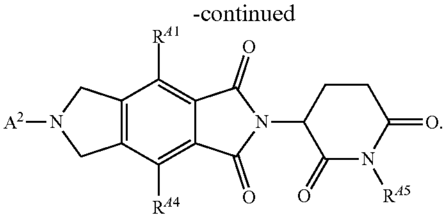

In some embodiments, the structure of Formula AA has the structure of Formula B:

Formula B

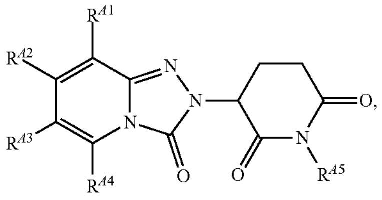

where $R^{A5}$ is H, optionally substituted $C_1$-$C_6$ alkyl, or optionally substituted $C_1$-$C_6$ heteroalkyl;

each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

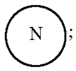;

and

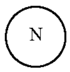

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$; or

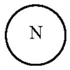

is substituted with $A^2$, or a pharmaceutically acceptable salt thereof.

In some embodiments, each of $R^{A1}$, $R^{A2}$, $R^{A3}$, and $R^{A4}$ is, H, $A^2$, halogen, optionally substituted $C_1$-$C_6$ alkyl, optionally substituted $C_1$-$C_6$ heteroalkyl, optionally substituted —O—$C_3$-$C_6$ carbocyclyl, hydroxyl, optionally substituted amino; or $R^{A1}$ and $R^{A2}$, $R^{A2}$ and $R^{A3}$, or $R^{A3}$ and $R^{A4}$, together with the carbon atoms to which each is attached, combine to form

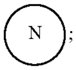; and 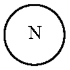

is optionally substituted $C_2$-$C_9$ heterocyclyl, which is optionally substituted with $A^2$, where one of $R^{A1}$, $R^{A2}$, $R^{A3}$, and $R^{A4}$ is $A^2$; or

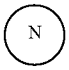

is substituted with $A^2$.

In some embodiments, each of $R^{A1}$, $R^{A2}$, $R^{A3}$, and $R^{A4}$ is, independently, H, $A^2$, F,

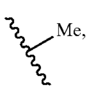, 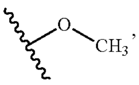, 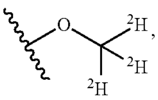, or 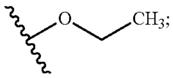;

or $R^{A1}$ and $R^{A2}$, $R^{A2}$ and $R^{A3}$, or $R^{A3}$ and $R^{A4}$, together with the carbon atoms to which each is attached, combine to form

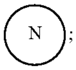; and 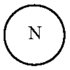

is optionally substituted $C_2$-$C_9$ heterocyclyl, which is optionally substituted with $A^2$, where one of $R^{A1}$, $R^{A2}$, $R^{A3}$, and $R^{A4}$ is $A^2$; or

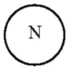

is substituted with $A^2$.

In some embodiments, $R^{A1}$ is $A^2$. In some embodiments, $R^{A2}$ is $A^2$. In some embodiments, $R^{A3}$ is $A^2$. In some embodiments, $R^{A4}$ is $A^2$. In some embodiments, $R^{A5}$ is $A^2$.

In some embodiments, $R^{A5}$ is H or optionally substituted $C_1$-$C_6$ alkyl.

In some embodiments, $R^{A5}$ is H or

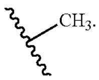.

In some embodiments, $R^{A5}$ is H. In some embodiments, $R^{A5}$ is

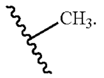

In some embodiments, the structure of Formula B has the structure of Formula B1:

Formula B1

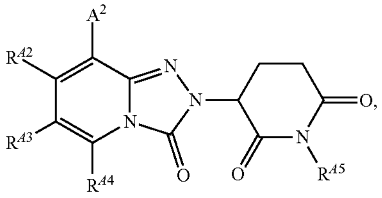

or a pharmaceutically acceptable salt thereof.

In some embodiments, the structure of Formula B has the structure of Formula B2:

Formula B2

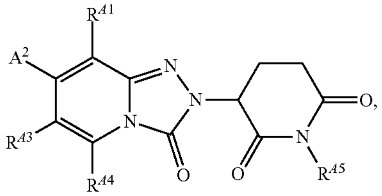

or a pharmaceutically acceptable salt thereof.

In some embodiments, the structure of Formula B has the structure of Formula B3:

Formula B3

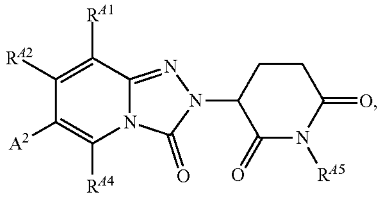

or a pharmaceutically acceptable salt thereof.

In some embodiments, the structure of Formula B has the structure of Formula B4:

Formula B4

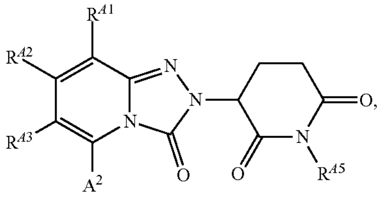

or a pharmaceutically acceptable salt thereof.

In some embodiments, the structure of Formula B is

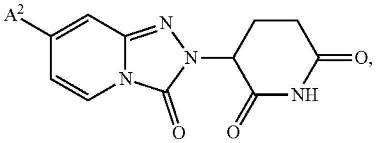

or

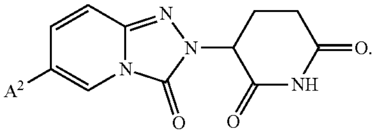

In some embodiments, the structure of Formula B

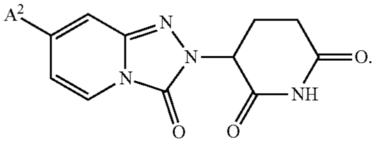

In some embodiments, the structure of Formula B is

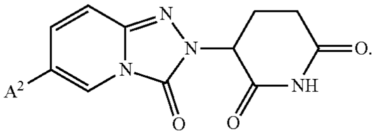

In some embodiments, the degradation moiety includes the structure of Formula C:

Formula C

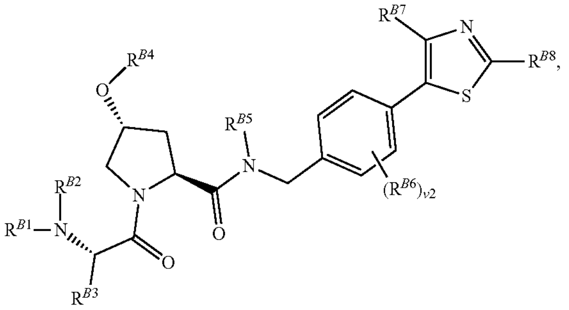

where $R^{B1}$ is H, $A^2$, optionally substituted $C_1$-$C_6$ alkyl, or optionally substituted $C_1$-$C_6$ heteroalkyl;

$R^{B2}$ is H, optionally substituted $C_1$-$C_6$ alkyl, or optionally substituted $C_1$-$C_6$ heteroalkyl;

$R^{B3}$ is $A^2$, optionally substituted $C_1$-$C_6$ alkyl, optionally substituted $C_1$-$C_6$ heteroalkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B4}$ is H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B5}$ is H, optionally substituted $C_1$-$C_6$ alkyl, or optionally substituted $C_1$-$C_6$ heteroalkyl;

v2 is 0, 1, 2, 3, or 4;

each $R^{B6}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each of $R^{B7}$ and $R^{B8}$ is, independently, H, halogen, optionally substituted $C_1$-$C_6$ alkyl, or optionally substituted $C_6$-$C_{10}$ aryl, where one of $R^{B1}$ and $R^{B3}$ is $A^2$, or a pharmaceutically acceptable salt thereof.

In some embodiments, the structure of Formula C is

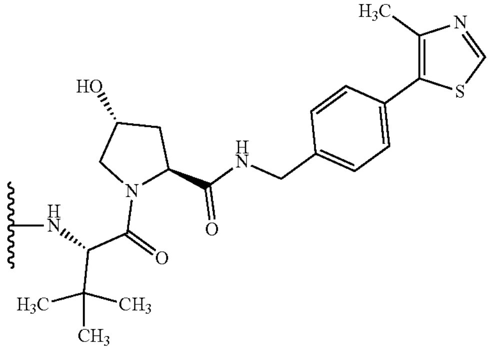

or

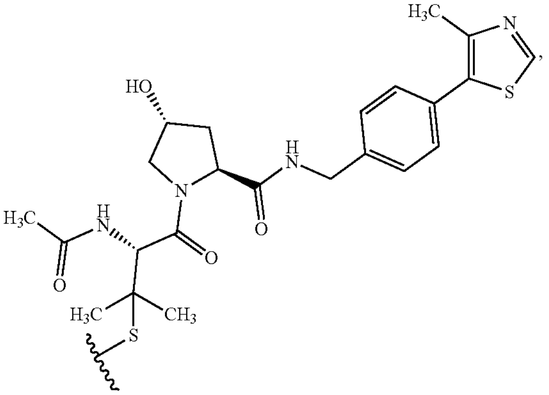

or derivative or analog thereof.

In some embodiments, the degrader moiety includes the structure of Formula D:

Formula D

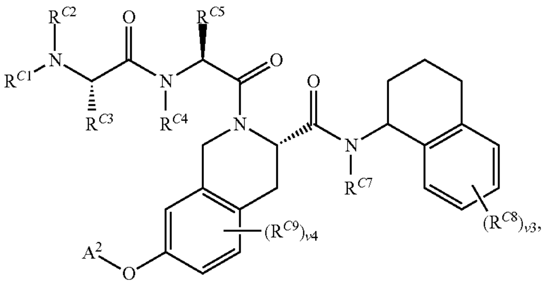

where $A^2$ is a bond between B and the linker;

each of $R^{C1}$, $R^{C2}$, and $R^{C7}$ is, independently, H, optionally substituted $C_1$-$C_6$ alkyl, or optionally substituted $C_1$-$C_6$ heteroalkyl;

$R^{C3}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{C5}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

v3 is 0, 1, 2, 3, or 4;

each $R^{C8}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

v4 is 0, 1, 2, 3, or 4; and each $R^{C9}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula D is

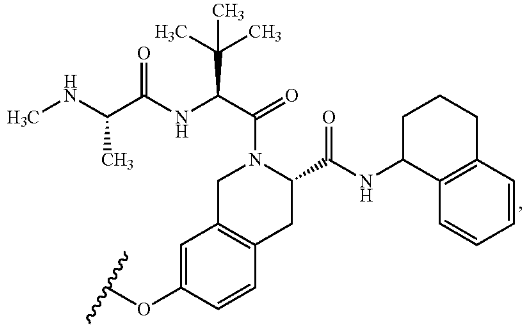 [SMILES: *Oc1ccc2c(c1)CN(C(=O)[C@@H](NC(=O)[C@H](C)NC)C(C)(C)C)[C@H](C(=O)NC1CCCc3ccccc31)C2]

or derivative or analog thereof.

In some embodiments, the degrader moiety includes the structure of Formula E:

Formula E

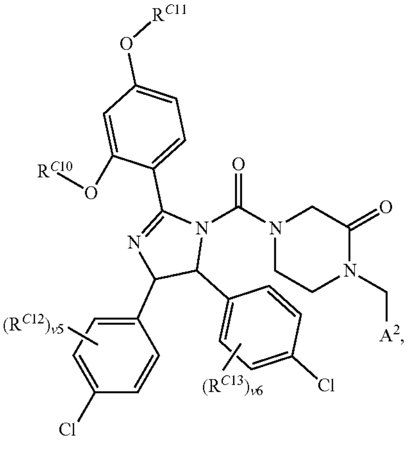

where $A^2$ is a bond between B and the linker;

each of $R^{C10}$ and $R^{C11}$ is, independently, H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

v5 is 0, 1, 2, 3, or 4;

each $R^{C12}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

v6 is 0, 1, 2, 3, or 4; and each $R^{21}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula E

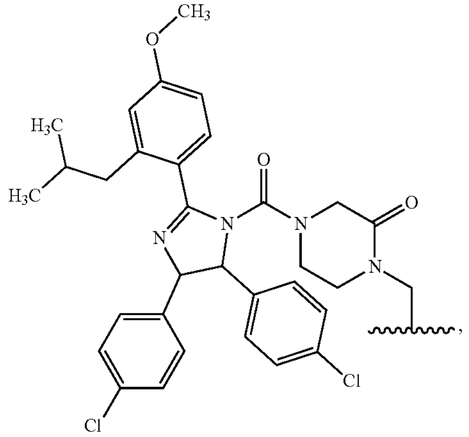 [SMILES: *CN1CCN(C(=O)N2C(c3ccc(OC)cc3CC(C)C)=NC(c3ccc(Cl)cc3)C2c2ccc(Cl)cc2)CC1=O]

or derivative or analog thereof.

In some embodiments, the linker has the structure of Formula III:

$$A^1\text{-}(B^1)_f\text{-}(C^1)_g\text{-}(B^2)_h\text{-}(D)\text{-}(B^3)_i\text{-}(C^2)_j\text{-}(B^4)_k\text{-}A^2 \quad \text{Formula III}$$

where $A^1$ is a bond between the linker and A;

$A^2$ is a bond between B and the linker;

each of $B^1$, $B^2$, $B^3$, and $B^4$ is, independently, optionally substituted $C_1$-$C_2$ alkyl, optionally substituted $C_1$-$C_3$ heteroalkyl, O, S, $S(O)_2$, or $NR^N$;

each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

each of $C^1$ and $C^2$ is, independently, carbonyl, thiocarbonyl, sulphonyl, or phosphoryl;

each of f, g, h, i, j, and k is, independently, 0 or 1; and

D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$-$(C^1)_g$-$(B^2)_h$- to -$(B^3)_i$-$(C^2)_j$-$(B^4)_k$-$A^2$.

In some embodiments, each of $B^1$, $B^2$, $B^3$, and $B^4$ is, independently, optionally substituted $C_1$-$C_4$ alkyl, optionally substituted $C_1$-$C_4$ heteroalkyl, or $NR^N$.

In some embodiments, each $R^N$ is, independently, H or optionally substituted $C_1$-$C_4$ alkyl.

In some embodiments, each $R^N$ is, independently, H or methyl.

In some embodiments, each of $B^1$ and $B^4$ is, independently,

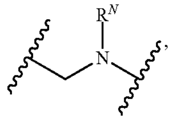,
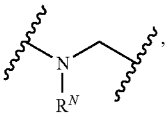,
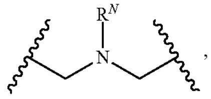,
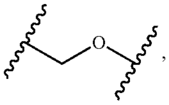,
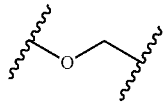, or
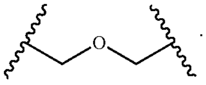.

In some embodiments, $B^1$ is

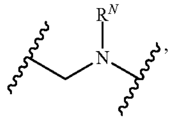,
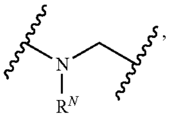,
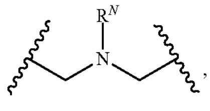, or
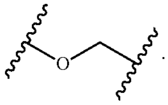.

In some embodiments, each of $C^1$ and $C^2$ is, independently,

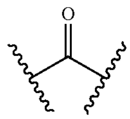 or
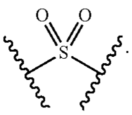.

In some embodiments, $C^1$ is

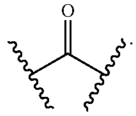 [SMILES: *C(*)=O].

In some embodiments, $B^2$ is $NR^N$. In some embodiments, $B^2$ is optionally substituted $C_1$-$C_4$ alkyl.

In some embodiments, f is 0. In some embodiments, f is 1. In some embodiments, g is 1. In some embodiments, h is 0. In some embodiments, h is 1. In some embodiments, i is 0. In some embodiments, j is 0. In some embodiments, k is 0.

In some embodiments, the linker has the structure of

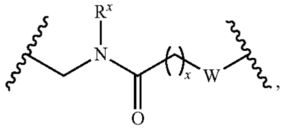, 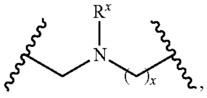,

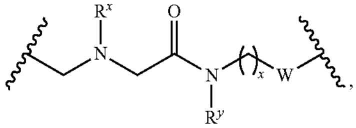,

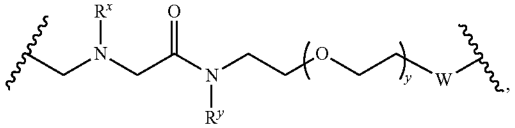,

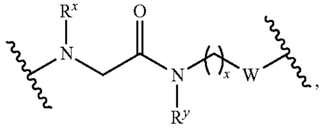,

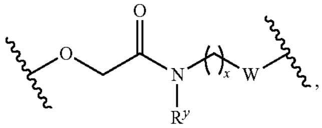,

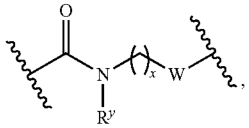, or

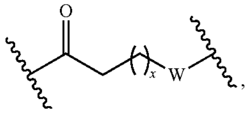, wherein x is 1, 2, 3, 4, 5, 6, 7, or 8;

y is 1, 2, 3, or 4;

$R^x$ is H, optionally substituted $C_1$-$C_6$ alkyl, optionally substituted $C_1$-$C_6$ heteroalkyl, or optionally substituted $C_3$-$C_6$ carbocyclyl;

$R^y$ is H, optionally substituted $C_1$-$C_6$ alkyl, optionally substituted $C_1$-$C_6$ heteroalkyl, or optionally substituted $C_3$-$C_6$ carbocyclyl; and W is O or $NR^w$, wherein $R^w$ is H, optionally substituted $C_1$-$C_6$ alkyl, optionally substituted $C_1$-$C_6$ heteroalkyl, or optionally substituted $C_3$-$C_6$ carbocyclyl.

In some embodiments, $R^x$ is H or me optionally substituted $C_1$-$C_6$ alkyl. In some embodiments, $R^y$ is H or optionally substituted $C_1$-$C_6$ alkyl. In some embodiments, $R^w$ is H or optionally substituted $C_1$-$C_6$alkyl.

In some embodiments, $R^x$ is H or methyl. In some embodiments, $R^y$ is H or methyl. In some embodiments, $R^w$ is H or methyl.

In some embodiments, the linker has the structure of

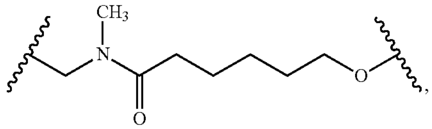,

-continued

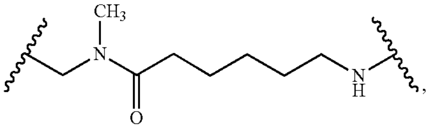,

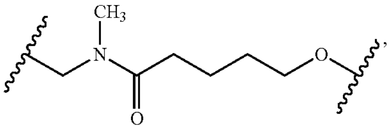,

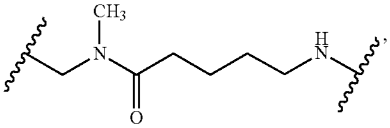,

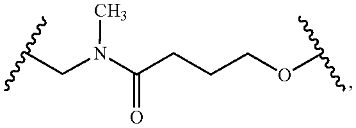,

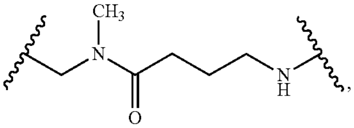,

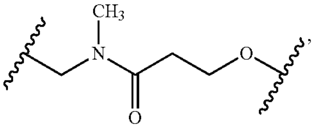,

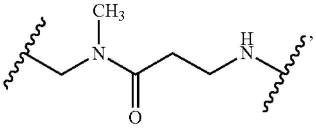,

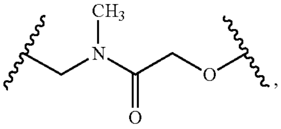,

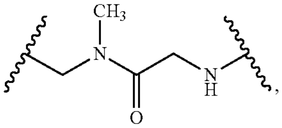, 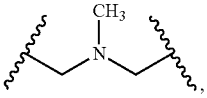,

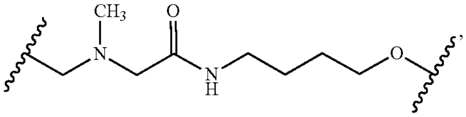,

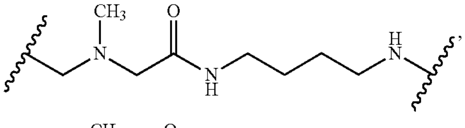,

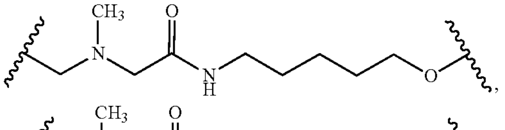,

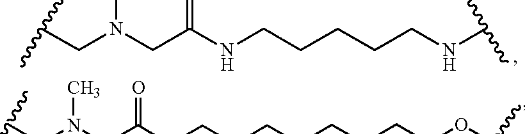,

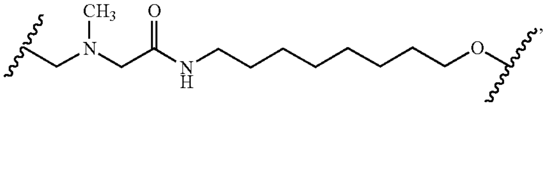,

-continued

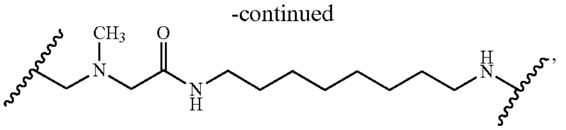
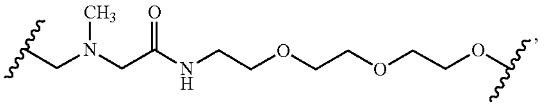
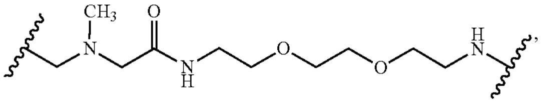
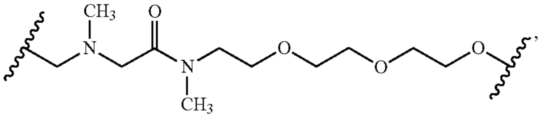
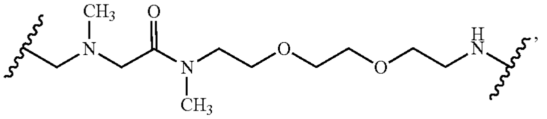
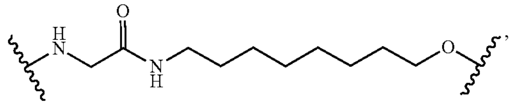
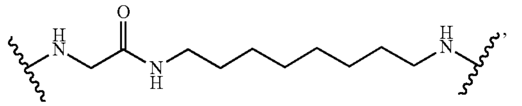
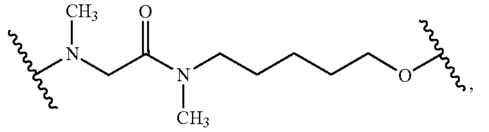
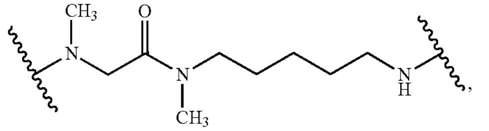
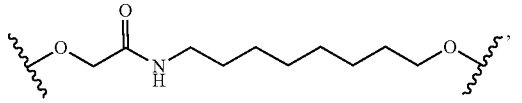
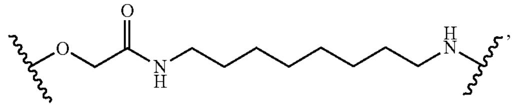
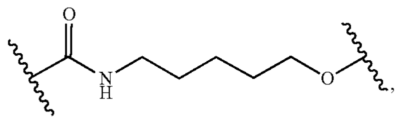
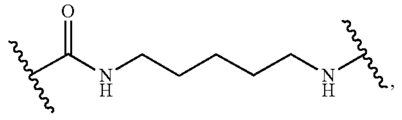
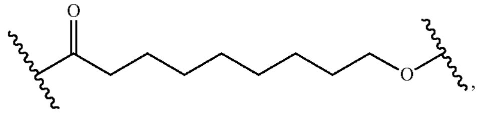
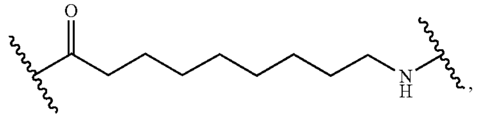

-continued

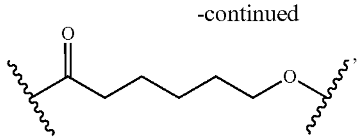

or

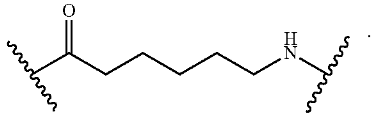

In some embodiments, L has the structure of Formula IV:

$$A^1\text{-}(E^1)\text{-}(F^1)\text{-}(C^3)_m\text{-}(E^3)_n\text{-}(F^2)_{o1}\text{-}(F^3)_{o2}\text{-}(E^2)_p\text{-}A^2 \qquad \text{Formula IV}$$

where $A^1$ is a bond between the linker and A;

$A^2$ is a bond between B and the linker;

each of m, n, o1, o2, and p is, independently, 0 or 1;

each of $E^1$ and $E^2$ is, independently, O, S, $NR^N$, optionally substituted $C_{1-10}$ alkyl, optionally substituted $C_{2-10}$ alkenyl, optionally substituted $C_{2-10}$ alkynyl, optionally substituted $C_2$-$C_{10}$ polyethylene glycol, or optionally substituted $C_{1-10}$ heteroalkyl;

$E^3$ is O, S, or $NR^N$;

each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

$C^3$ is carbonyl, thiocarbonyl, sulphonyl, or phosphoryl; and each of $F^1$, $F^2$, and $F^3$ is, independently, optionally substituted $C_3$-$C_{10}$ carbocyclyl, optionally substituted $C_{2-10}$ heterocyclyl, optionally substituted $C_6$-$C_{10}$ aryl, or optionally substituted $C_2$-$C_9$ heteroaryl.

In some embodiments, the linker has the structure of Formula IVa:

$$A^1\text{-}(E^1)\text{-}(F^1)\text{-}(C^3)_m\text{-}(E^2)_p\text{-}A^2. \qquad \text{Formula IVa}$$

In some embodiments, the linker has the structure of Formula IVb:

$$A^1\text{-}(E^1)\text{-}(F^1)\text{-}(E^2)_p\text{-}A^2. \qquad \text{Formula IVb}$$

In some embodiments, the linker has the structure of Formula IVc:

$$A^1\text{-}(E^1)\text{-}(F^1)\text{-}A^2. \qquad \text{Formula IVc}$$

In some embodiments, the linker has the structure of Formula IVd:

$$A^1\text{-}(E^1)\text{-}(F^1)\text{-}(C^3)_m\text{-}(F^2)_{o1}\text{-}A^2. \qquad \text{Formula IVd}$$

In some embodiments, the linker has the structure of Formula IVe $$A^1\text{-}(E^1)\text{-}(F^1)\text{-}(E^3)_n\text{-}(F^2)_{o1}\text{-}(E^2)_p\text{-}A^2. \qquad \text{Formula IVe}$$

In some embodiments, each of $E^1$ and $E^2$ is, independently, $NR^N$, optionally substituted $C_{1-10}$ alkyl, optionally substituted $C_2$-$C_{10}$ polyethylene glycol, or optionally substituted $C_{1-10}$ heteroalkyl.

In some embodiments, $E^3$ is O.

In some embodiments, each $R^N$ is, independently, H or optionally substituted $C_{1-4}$ alkyl.

In some embodiments, each $R^N$ is, independently, H or methyl.

In some embodiments, $E^1$ is
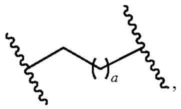,
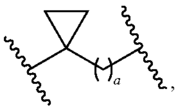,
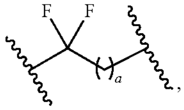,
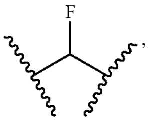,
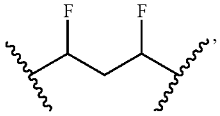,
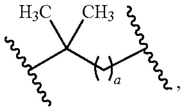, or
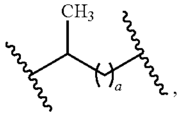,
where a is 0, 1, 2, 3, 4, or 5.
In some embodiments, $E^1$ is
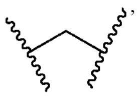,
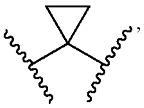,
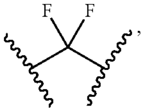,
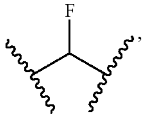,
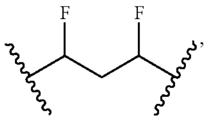,
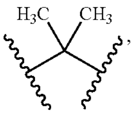,
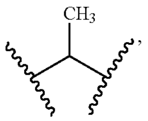,
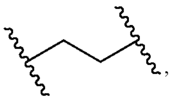, or
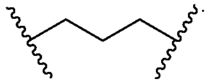.
In some embodiments, $E^1$ is
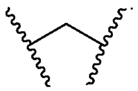 [SMILES: *C*].
In some embodiments, $E^1$ is
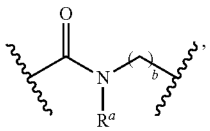,
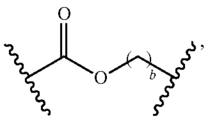,
-continued
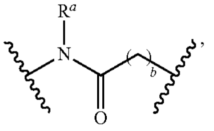,
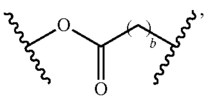,
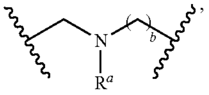,
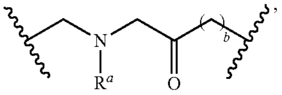,
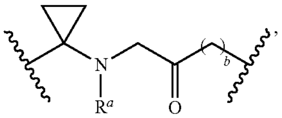,
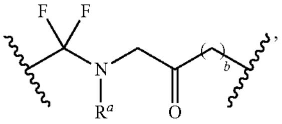,
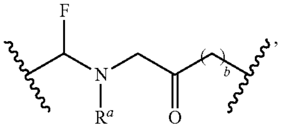,
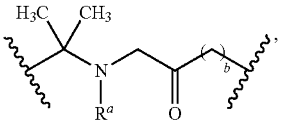,
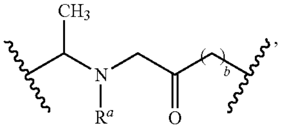,
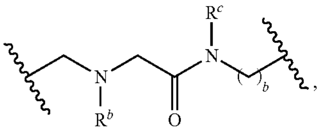,
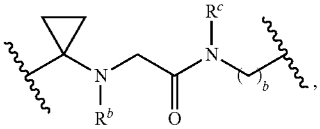,
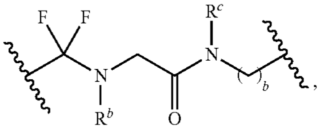,
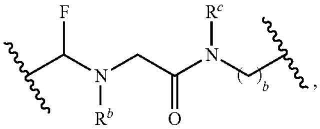,
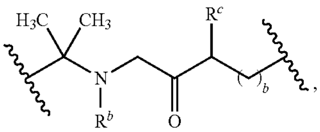,
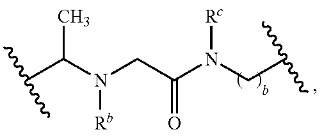, -continued

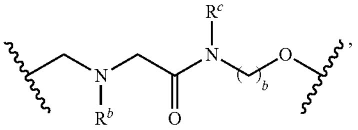

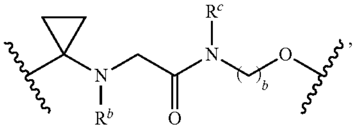

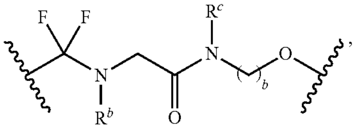

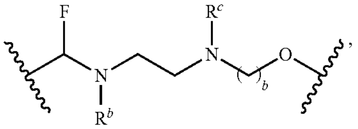

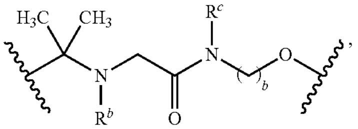

or

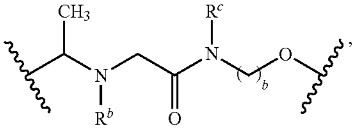

where b is 0, 1, 2, 3, 4, 5, or 6;

$R^a$ is H, optionally substituted $C_1$-$C_6$ alkyl, optionally substituted $C_1$-$C_6$ heteroalkyl, or optionally substituted $C_3$-$C_6$ carbocyclyl;

$R^b$ is H, optionally substituted $C_1$-$C_6$ alkyl, optionally substituted $C_1$-$C_6$ heteroalkyl, or optionally substituted $C_3$-$C_6$ carbocyclyl; and $R^c$ is H, optionally substituted $C_1$-$C_6$ alkyl, optionally substituted $C_1$-$C_6$ heteroalkyl, or optionally substituted $C_3$-$C_6$ carbocyclyl.

In some embodiments, $E^1$ is

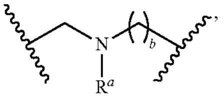

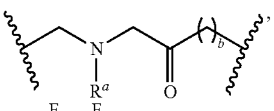

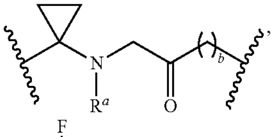

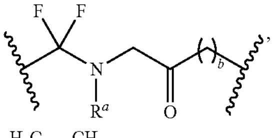

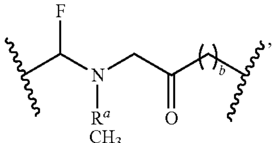

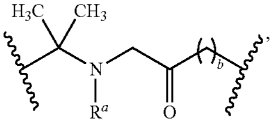

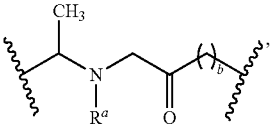

-continued

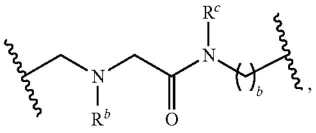

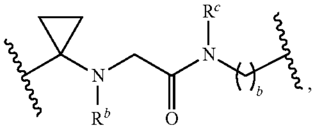

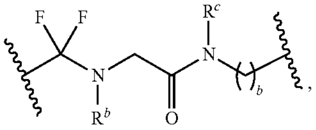

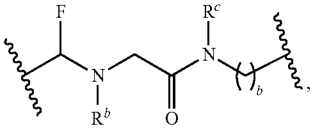

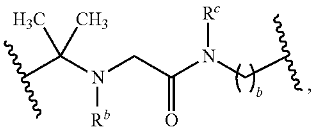

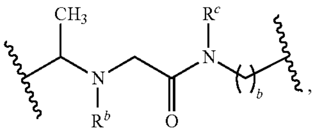

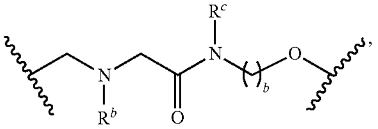

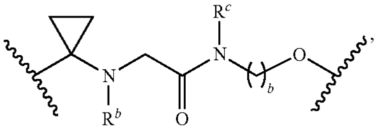

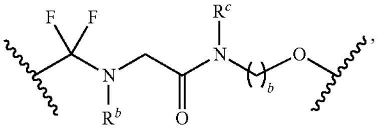

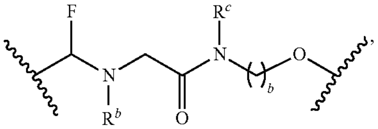

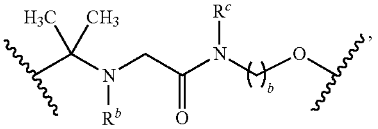

or

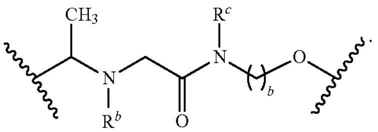

In some embodiments, $E^1$ is

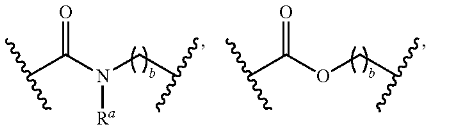

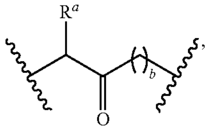

or

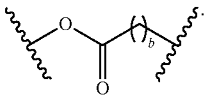

In some embodiments, $E^1$ is

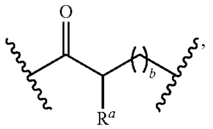

or

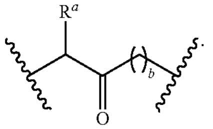

In some embodiments, $R^a$ is H or optionally substituted $C_1$-$C_6$ alkyl. In some embodiments, $R^b$ is H or optionally substituted $C_1$-$C_6$ alkyl. In some embodiments, $R^c$ is H or optionally substituted $C_1$-$C_6$ alkyl.

In some embodiments, $R^a$ is H or methyl. In some embodiments, $R^b$ is H or methyl. In some embodiments, $R^c$ is H or methyl.

In some embodiments, b is 0, 1, 2, or 3. In some embodiments, b is 0. In some embodiments, b is 1. In some embodiments, b is 2. In some embodiments, b is 3.

In some embodiments, $E^1$ is

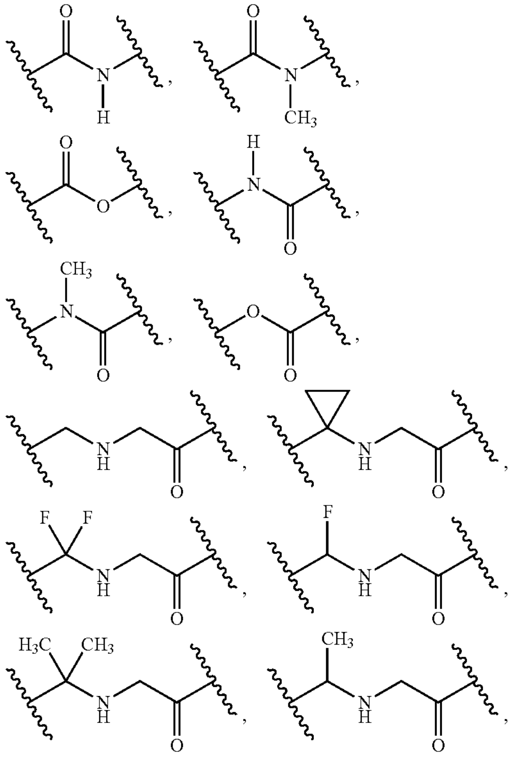

-continued

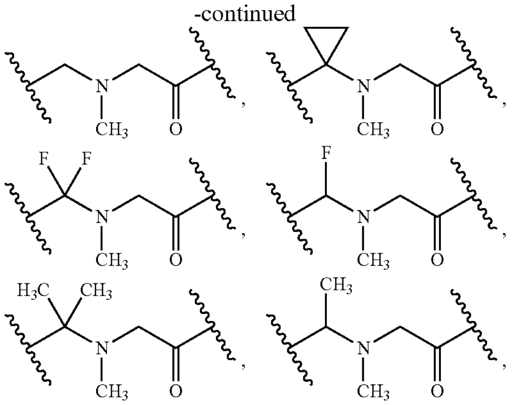

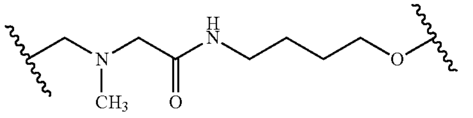

or

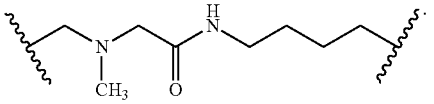

In some embodiments, $E^1$ is

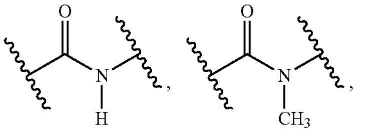

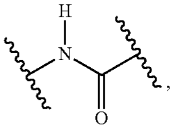

or

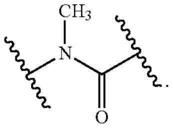

In some embodiments, $E^1$ is

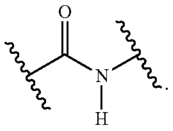 [SMILES: *NC(*)=O]

In some embodiments, $E^1$ is

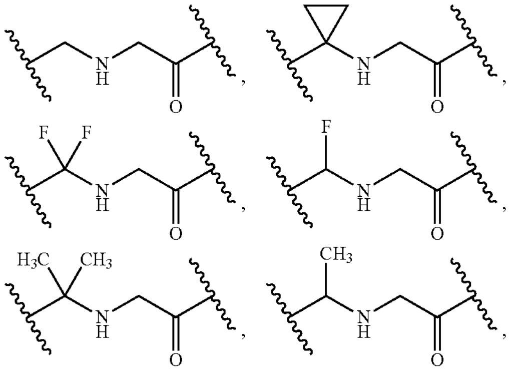

-continued

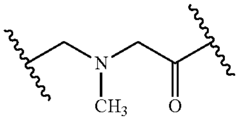, 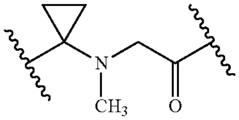,

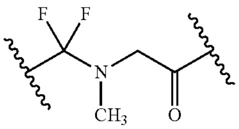, 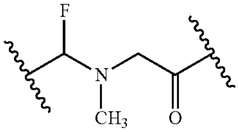,

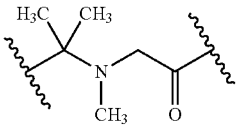, 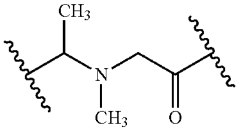,

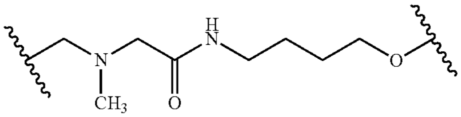 or

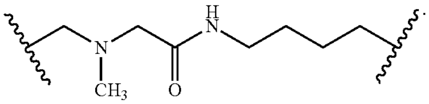.

In some embodiments, $E^1$ is

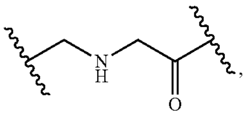, 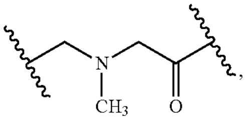,

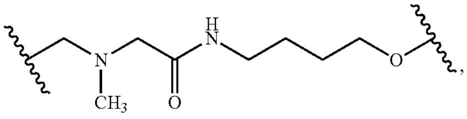, or

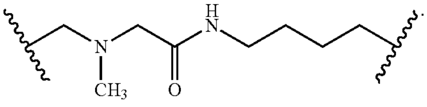.

In some embodiments, $E^1$ is

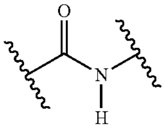, 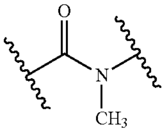,

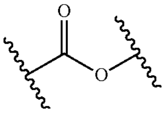, 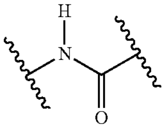,

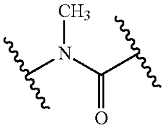, or 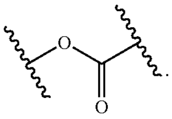.

In some embodiments, $E^2$ is O, $NR^w$,

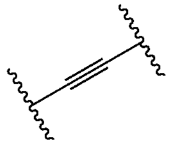, 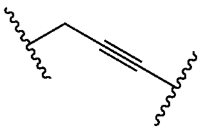,

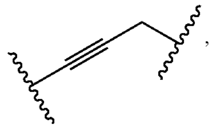, 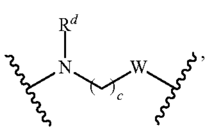,

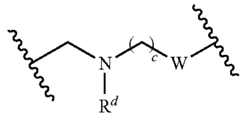, 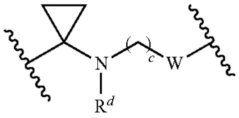,

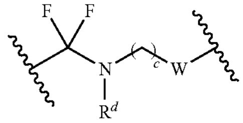, 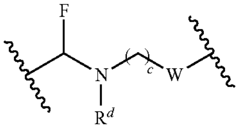,

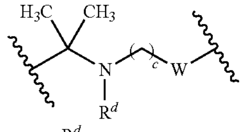, 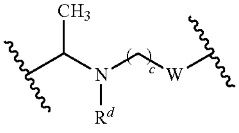,

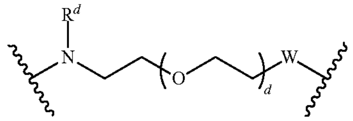,

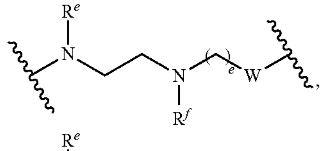,

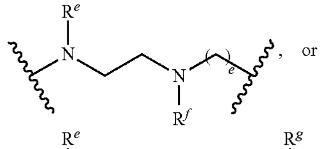, or

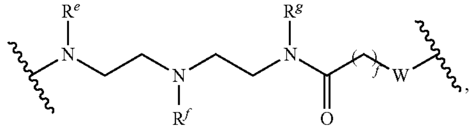, wherein c is 0, 1, 2, 3, 4, 5, 6, 7, or 8;

d is 0, 1, 2, or 3;

e is 0, 1, 2, 3, 4, 5, or 6;

f is 0, 1, 2, 3, or 4;

$R^d$ is H, optionally substituted $C_1$-$C_6$ alkyl, optionally substituted $C_1$-$C_6$ heteroalkyl, or optionally substituted $C_3$-$C_6$ carbocyclyl;

$R^e$ is H, optionally substituted $C_1$-$C_6$ alkyl, optionally substituted $C_1$-$C_6$ heteroalkyl, or optionally substituted $C_3$-$C_6$ carbocyclyl;

$R^f$ is H, optionally substituted $C_1$-$C_6$ alkyl, optionally substituted $C_1$-$C_6$ heteroalkyl, or optionally substituted $C_3$-$C_6$ carbocyclyl;

$R^g$ is H, optionally substituted $C_1$-$C_6$ alkyl, optionally substituted $C_1$-$C_6$ heteroalkyl, or optionally substituted $C_3$-$C_6$ carbocyclyl; and W is O or $NR^w$, wherein $R^w$ is H or optionally substituted $C_1$-$C_6$ alkyl.

In some embodiments, $E^2$ is O, $NR^w$,

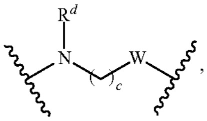,

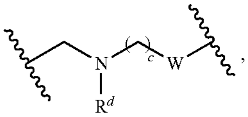,

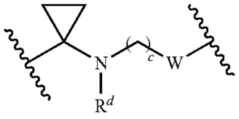,

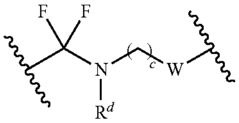,

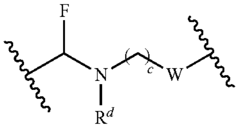,

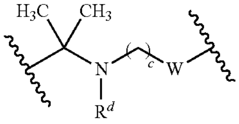,

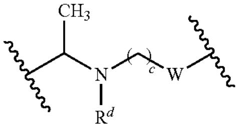,

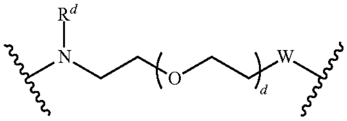,

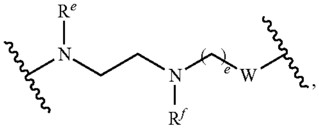,

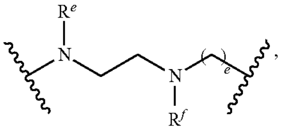, or

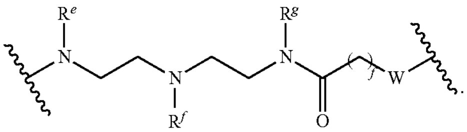.

In some embodiments, $R^d$ is H or optionally substituted $C_1$-$C_6$ alkyl. In some embodiments, $R^e$ is H or optionally substituted $C_1$-$C_6$ alkyl. In some embodiments, $R^f$ is H or optionally substituted $C_1$-$C_6$ alkyl. In some embodiments, $R^g$ is H or optionally substituted $C_1$-$C_6$ alkyl. In some embodiments, $R^w$ is H or optionally substituted $C_1$-$C_6$ alkyl.

In some embodiments, $R^d$ is H or methyl. In some embodiments, $R^e$ is H or methyl. In some embodiments, $R^f$ is H or methyl. In some embodiments, $R^g$ is H or methyl. In some embodiments, $R^w$ is H or methyl.

In some embodiments, $E^2$ is

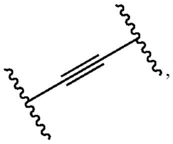,

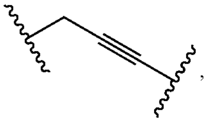, or

-continued

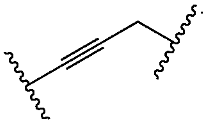.

In some embodiments, $E^2$ is O,

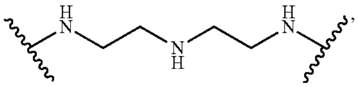,

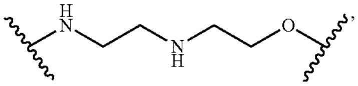,

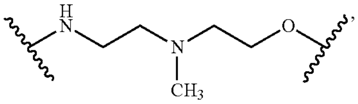,

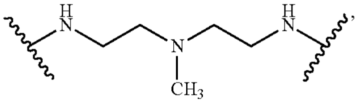,

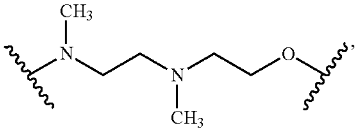,

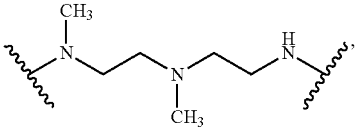,

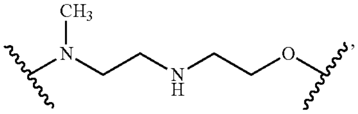,

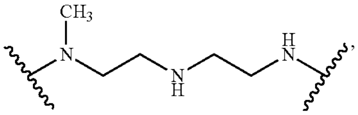,

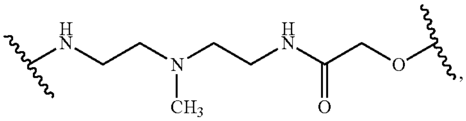, or

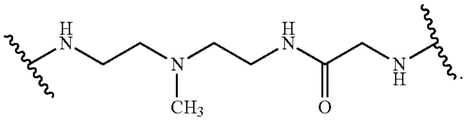.

In some embodiments, each of $F^1$, $F^2$, or $F^3$ is, independently, optionally substituted $C_3$-$C_{10}$ carbocyclyl.

In some embodiments, the $C_3$-$C_{10}$ carbocyclyl is monocyclic. In some embodiments, the $C_3$-$C_{10}$ carbocyclyl is polycyclic.

In some embodiments, the $C_3$-$C_{10}$ carbocyclyl is bicyclic.

In some embodiments, the $C_3$-$C_{10}$ carbocyclyl is bridged. In some embodiments, the $C_3$-$C_{10}$ carbocyclyl is fused. In some embodiments, the $C_3$-$C_{10}$ carbocyclyl is spirocyclic.

In some embodiments, the $C_3$-$C_{10}$ carbocyclyl is

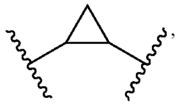, 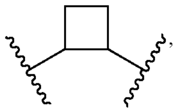, 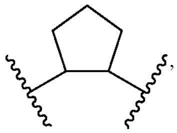, or 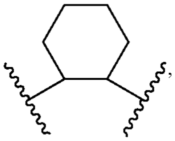,

In some embodiments, $F^2$ is

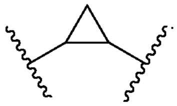 [SMILES: *C1CC1*].

In some embodiments, the $C_3$-$C_{10}$ carbocyclyl is

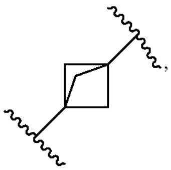, 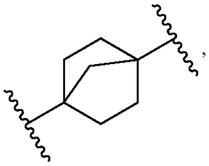, 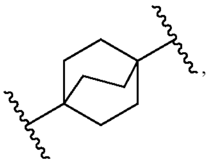, or 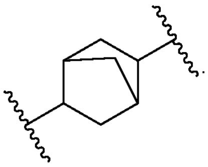.

In some embodiments, $F^1$ is

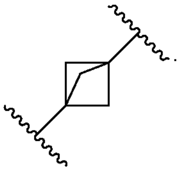 [SMILES: *C12CC(*)(C1)C2].

In some embodiments, each of $F^1$, $F^2$, or $F^3$ is, independently, optionally substituted $C_2$-$C_9$ heterocyclyl.

In some embodiments, the $C_2$-$C_9$ heterocyclyl is monocyclic. In some embodiments, the $C_2$-$C_9$ heterocyclyl is polycyclic.

In some embodiments, the $C_2$-$C_9$ heterocyclyl is bicyclic.

In some embodiments, the $C_2$-$C_9$ heterocyclyl is bridged. In some embodiments, the $C_2$-$C_9$ heterocyclyl is fused. In some embodiments, the $C_2$-$C_9$ heterocyclyl is spirocyclic.

In some embodiments, the $C_2$-$C_9$ heterocyclyl includes a quaternary amine.

In some embodiments, the $C_2$-$C_9$ heterocyclyl is

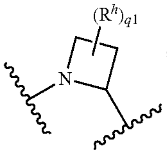, 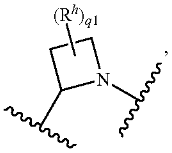,

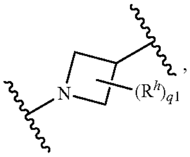, 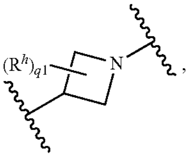,

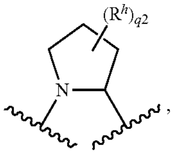, 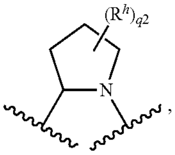,

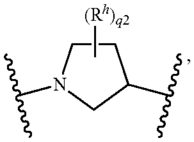, 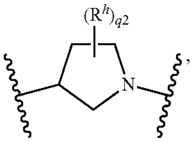,

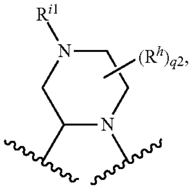 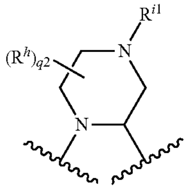,

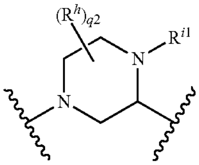, 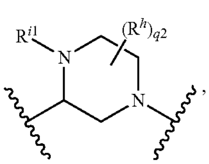,

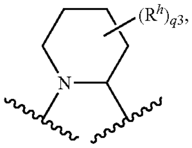 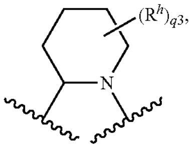

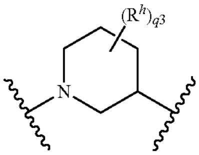, 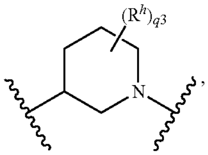,

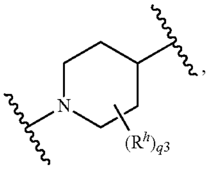, 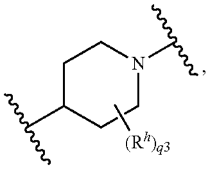,

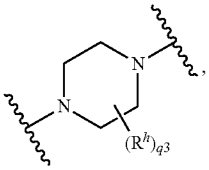, 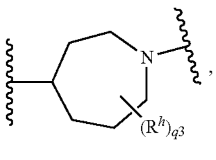, or

-continued

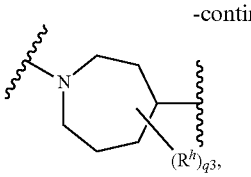

where q1 is 0, 1, 2, 3, or 4;

q2 is 0, 1, 2, 3, 4, 5, or 6;

q3 is 0, 1, 2, 3, 4, 5, 6, 7, or 8;

each $R^h$ is, independently, $^2$H, halogen, optionally substituted $C_1$-$C_6$ alkyl, $OR^{i2}$, or $NR^{i3}R^{i4}$; or two $R^h$ groups, together with the carbon atom to which each is attached, combine to form an optionally substituted $C_3$-$C_{10}$ carbocyclyl or optionally substituted $C_2$-$C_9$ heterocyclyl; or two $R^h$ groups, together with the carbon atoms to which each is attached, combine to form an optionally substituted $C_3$-$C_{10}$ carbocyclyl or optionally substituted $C_2$-$C_9$ heterocyclyl;

$R^{i1}$ is H or optionally substituted $C_1$-$C_6$ alkyl;

$R^{i2}$ is H, optionally substituted $C_1$-$C_6$ alkyl, optionally substituted $C_1$-$C_6$ heteroalkyl, or optionally substituted $C_3$-$C_6$ carbocyclyl;

$R^{i3}$ is H or optionally substituted $C_1$-$C_6$ alkyl; and $R^{i4}$ is H or optionally substituted $C_1$-$C_6$ alkyl.

In some embodiments, each $R^h$ is, independently, halogen, optionally substituted $C_1$-$C_6$ alkyl, $OR^{i2}$, or $NR^{i3}R^{i4}$. In some embodiments, $R^{i1}$ is H or optionally substituted $C_1$-$C_6$ alkyl. In some embodiments, $R^{i2}$ is H or optionally substituted $C_1$-$C_6$ alkyl. In some embodiments, $R^{i3}$ is H or optionally substituted $C_1$-$C_6$ alkyl. In some embodiments, $R^{i4}$ is H or optionally substituted $C_1$-$C_6$ alkyl.

In some embodiments, the $C_2$-$C_9$ heterocyclyl is

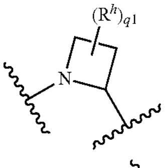 , 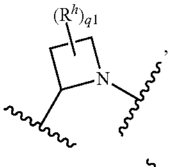 ,

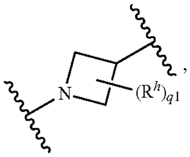 , 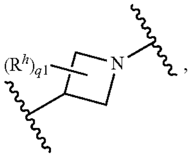 ,

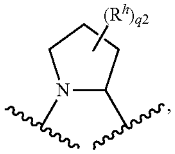 , 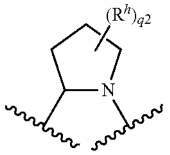 ,

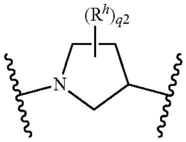 , 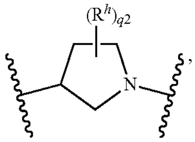 ,

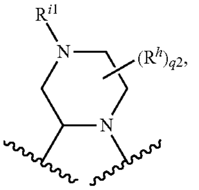 , 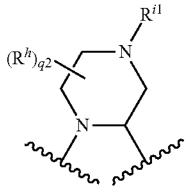 ,

-continued

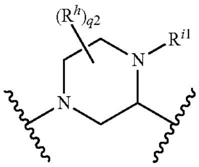 , 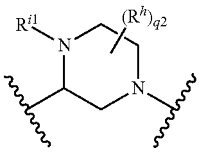 ,

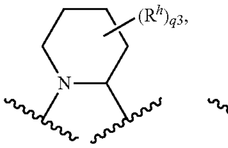 , 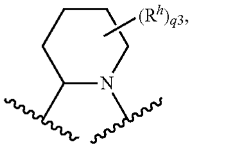 ,

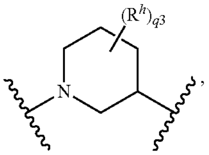 , 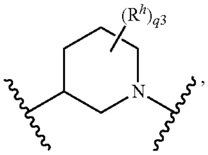 ,

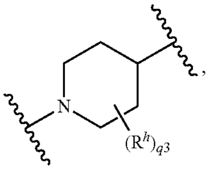 , 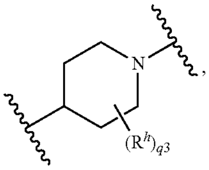 , or

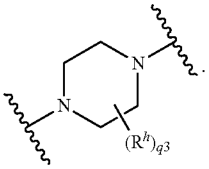 .

In some embodiments, each $R^h$ is, independently, halogen, optionally substituted $C_1$-$C_6$ alkyl, $OR^{i2}$, or $NR^{i3}R^{i4}$. In some embodiments, each $R^h$ is, independently, halogen, optionally substituted $C_1$-$C_6$ alkyl, or $NR^{i3}R^{i4}$.

In some embodiments, each $R^h$ is, independently, $^2$H, halogen, cyano, optionally substituted $C_1$-$C_6$ alkyl, $OR^{i2}$, or $NR^{i3}R^{i4}$. In some embodiments, two $R^h$ groups, together with the carbon atom to which each is attached, combine to form an optionally substituted $C_3$-$C_{10}$ carbocyclyl or optionally substituted $C_2$-$C_9$ heterocyclyl. In some embodiments, two $R^h$ groups, together with the carbon atoms to which each is attached, combine to form an optionally substituted $C_3$-$C_{10}$ carbocyclyl or optionally substituted $C_2$-$C_9$ heterocyclyl.

In some embodiments, each $R^h$ is, independently, H, $^2$H, F, methyl,

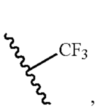 , 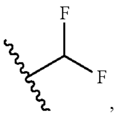 , 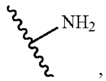 , 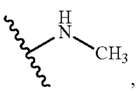 , or

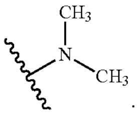 .

In some embodiments, each $R^h$ is, independently, F, methyl, or $NR^{i3}R^{i4}$.

In some embodiments, q1 is 0, 1, or 2. In some embodiments, q1 is 0. In some embodiments, q1 is 1. In some embodiments, q1 is 2.

In some embodiments, q2 is 0, 1, or 2. In some embodiments, q2 is 0. In some embodiments, q2 is 1. In some embodiments, q2 is 2.
In some embodiments, q3 is 0, 1, or 2. In some embodiments, q3 is 0. In some embodiments, q3 is 1. In some embodiments, q3 is 2.
In some embodiments, the $C_2$-$C_9$ heterocyclyl is
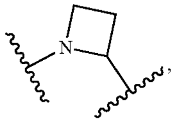
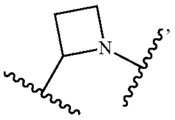
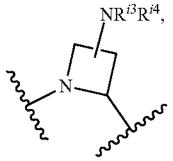
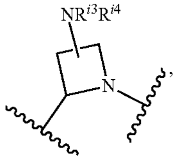
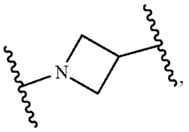
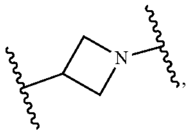
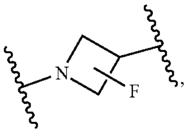
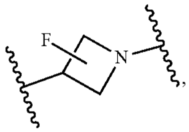
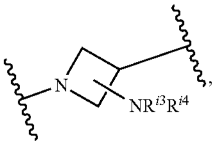
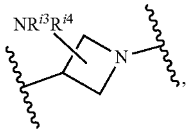
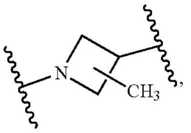
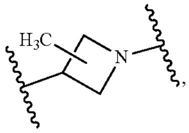
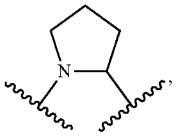
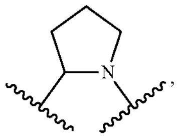
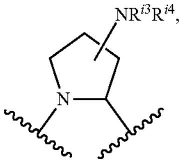
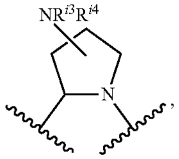
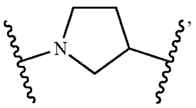
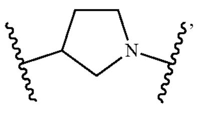
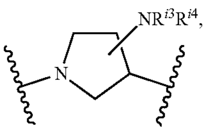
-continued
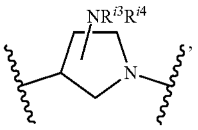
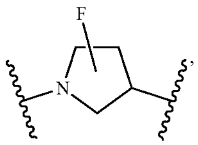
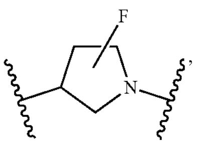
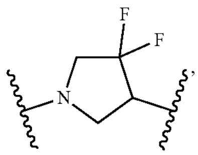
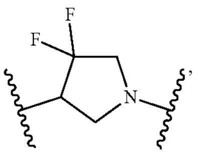
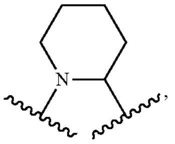
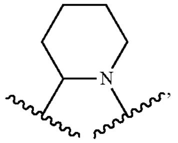
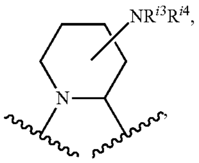
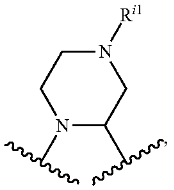
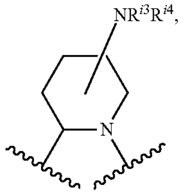
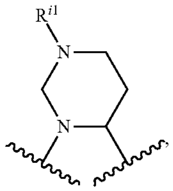
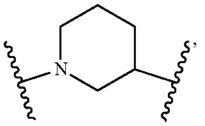
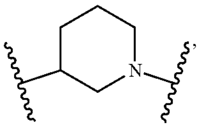
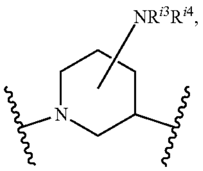
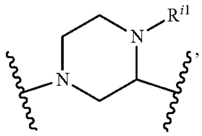
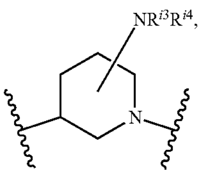

-continued
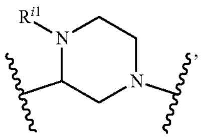
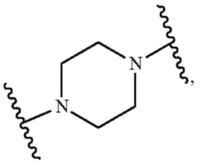
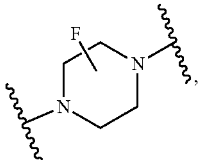
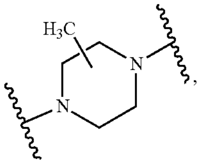
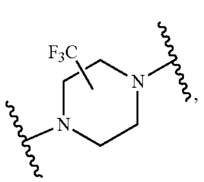
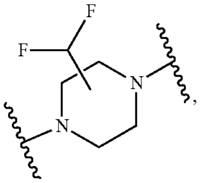
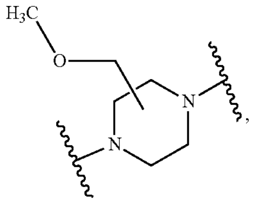
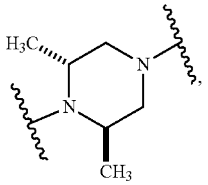
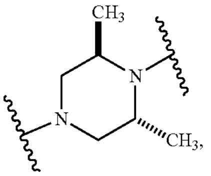
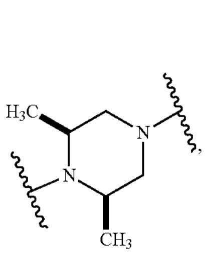
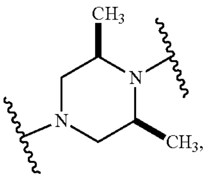
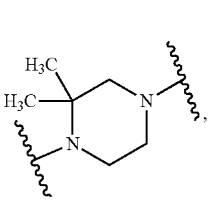
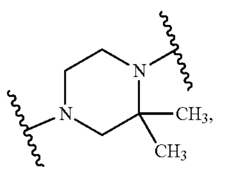
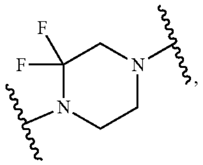
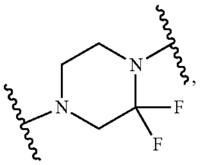
+
-continued
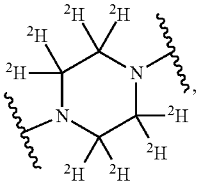
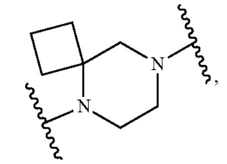
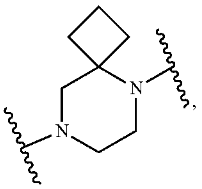
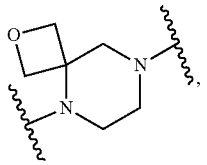
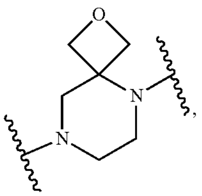
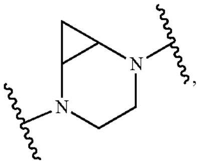
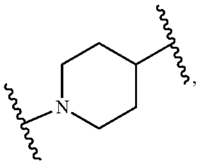
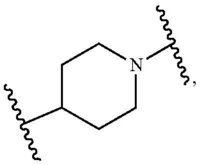
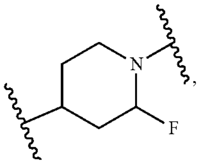
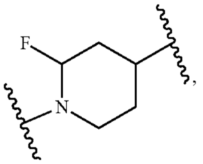
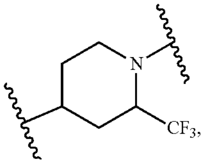
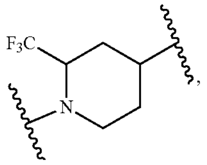
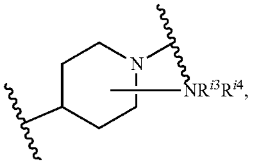
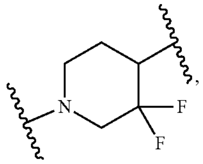
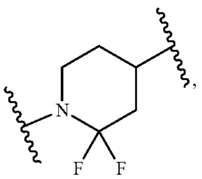
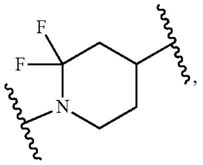
or
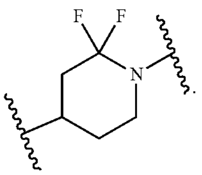

In some embodiments, the $C_2$-$C_9$ heterocyclyl is
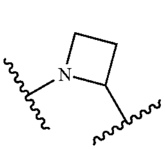, 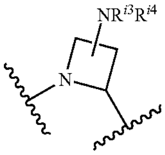, 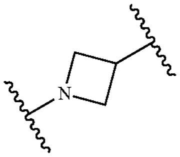, 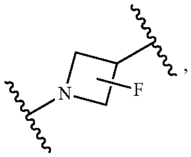, 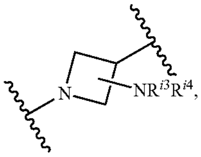, 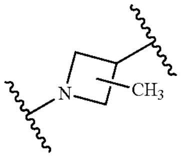, 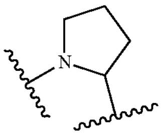, 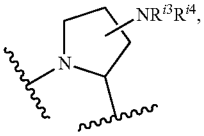, 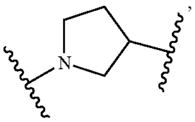, 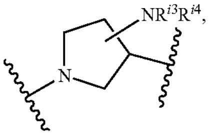, 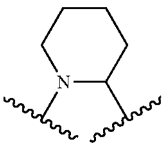, 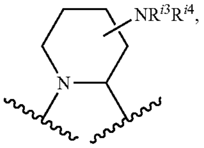, 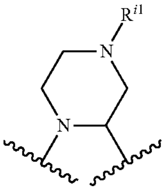, 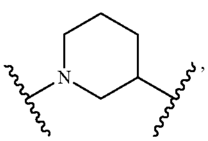, 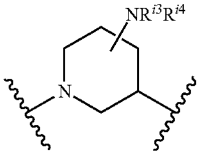, 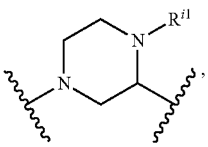, 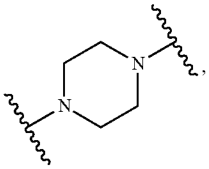, 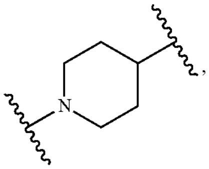, 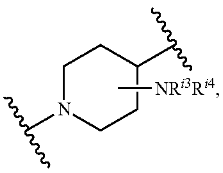, 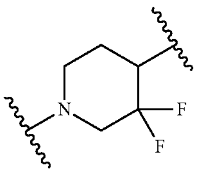,
-continued
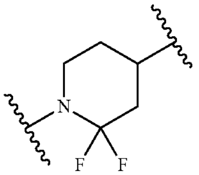, 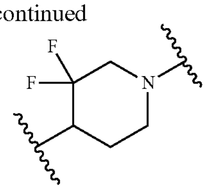, or 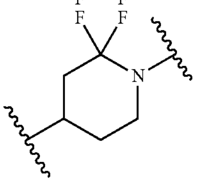.
In some embodiments, $F^1$ is
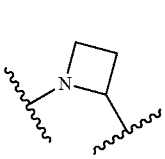, 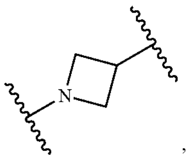, 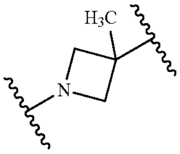, 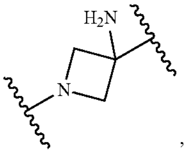, 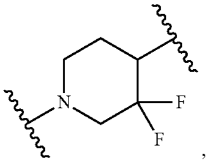, 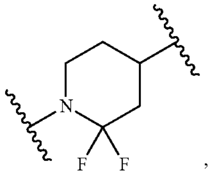, 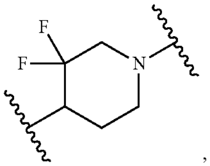, or 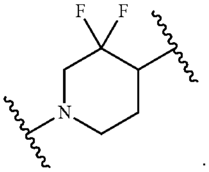.
In some embodiments, $F^1$ is
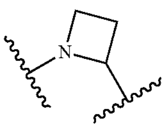, 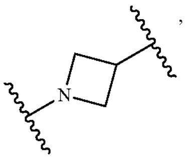, 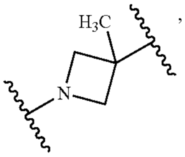, 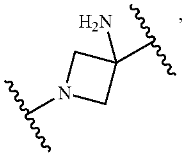, 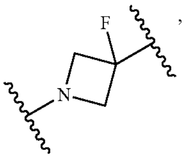, 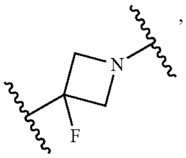, -continued

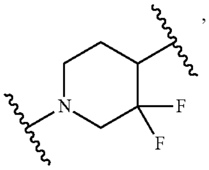

,

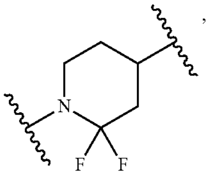

,

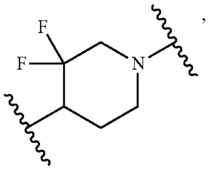

, or

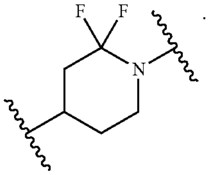

.

In some embodiments, $F^2$ is

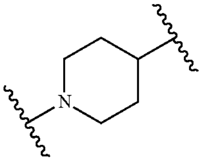

or

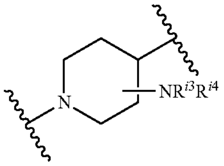

.

In some embodiments, $F^3$ is

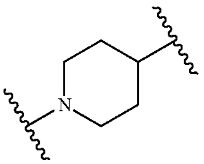

or

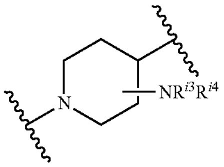

.

In some embodiments, $R^{i1}$ is H or methyl. In some embodiments, $R^{i2}$ is H or methyl. In some embodiments, $R^{i3}$ is H or methyl. In some embodiments, $R^{i4}$ is H or methyl.

In some embodiments, the $C_2$-$C_9$ heterocyclyl is

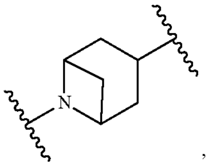

,

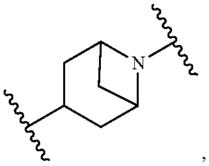

,

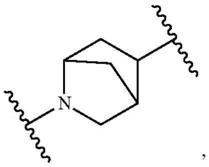

,

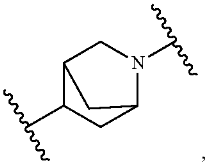

, or

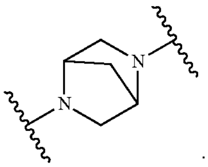

.

In some embodiments, the $C_2$-$C_9$ heterocyclyl is

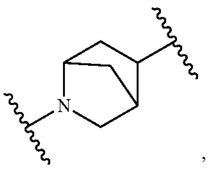

,

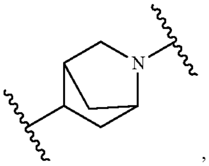

, or

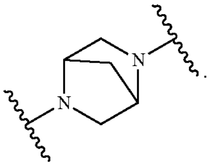

.

In some embodiments, the $C_2$-$C_9$ heterocyclyl is

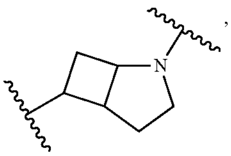

,

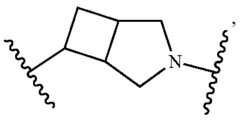

,

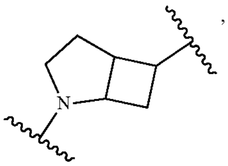

,

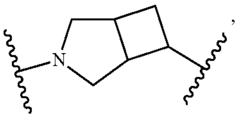

,

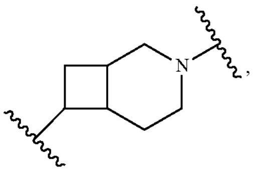

,

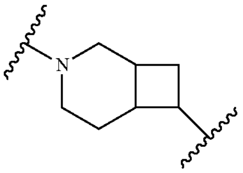

,

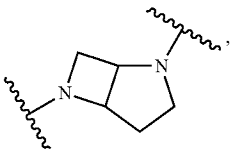

,

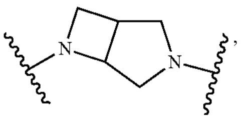

,

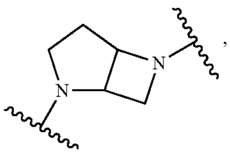

,

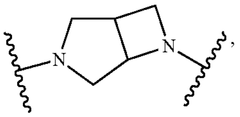

,

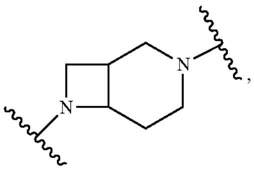

,

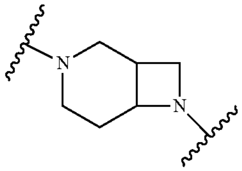

,

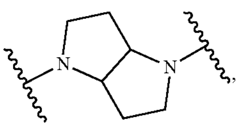

,

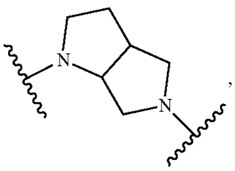

,

-continued
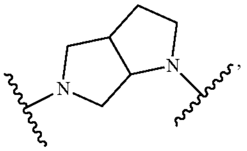,
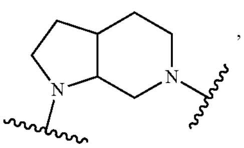,
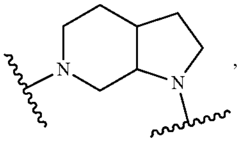,
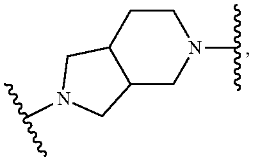,
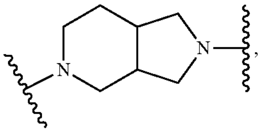, or
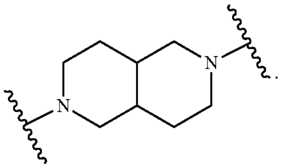.
In some embodiments, the $C_2$-$C_9$ heterocyclyl is
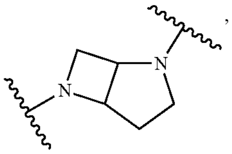,
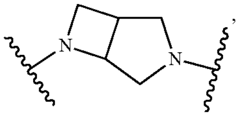,
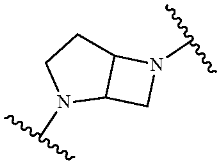,
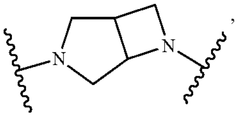,
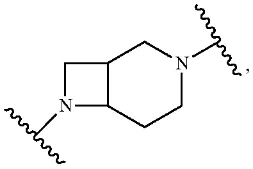,
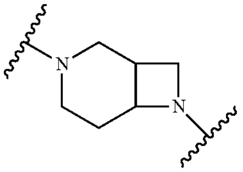,
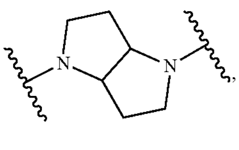,
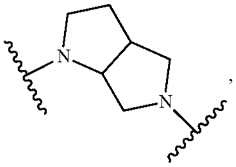,
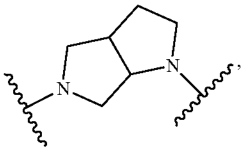,
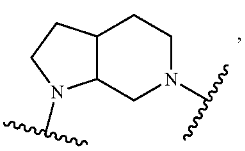,
-continued
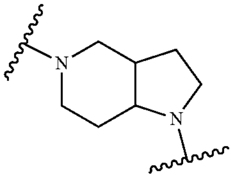,
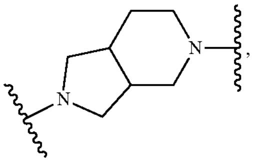,
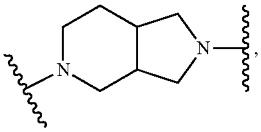, or
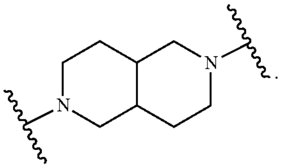.
In some embodiments, the $C_2$-$C_9$ heterocyclyl is
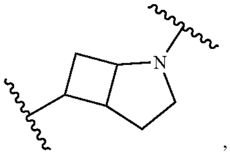,
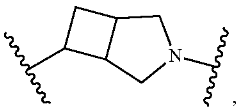,
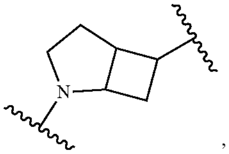,
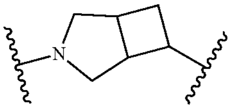,
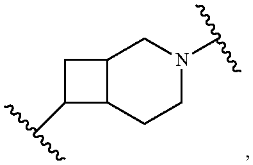, or
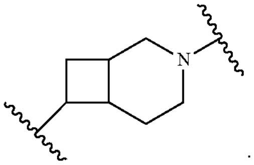.
In some embodiments, $F^1$ is
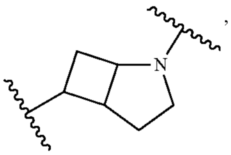,
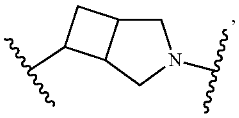,
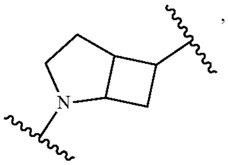,
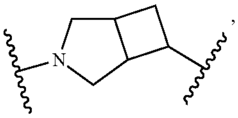, -continued
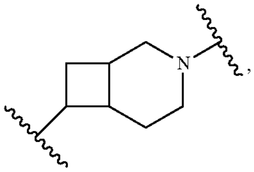, 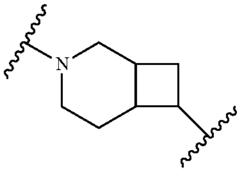,
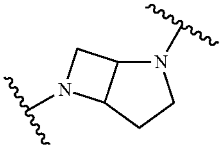, 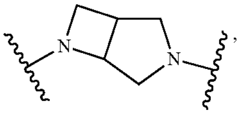,
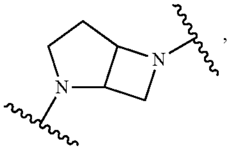, 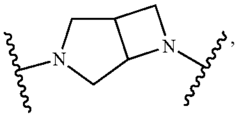,
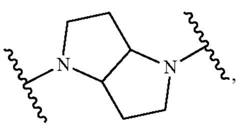, 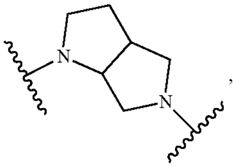,
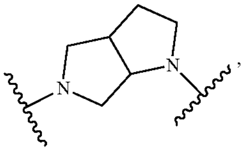, 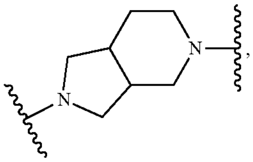,
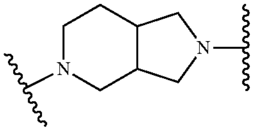, or
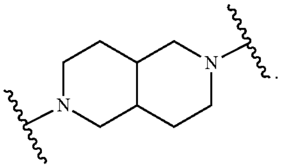.
In some embodiments, $F^1$ is
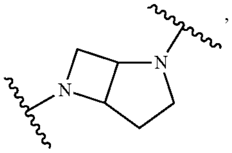, 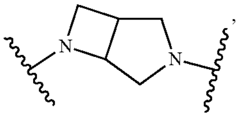,
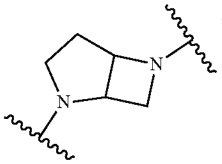, 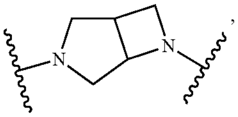,
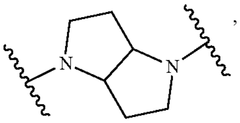, 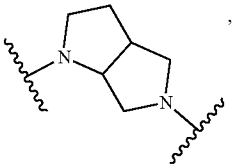,
-continued
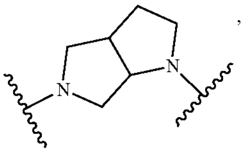, 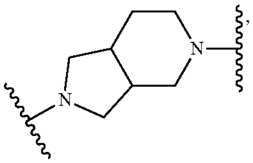,
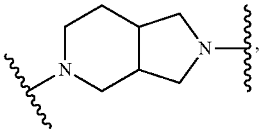, or
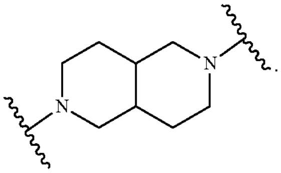.
In some embodiments, $F^1$ is
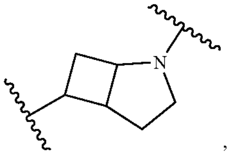, 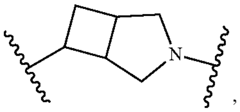,
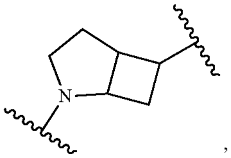, 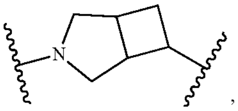,
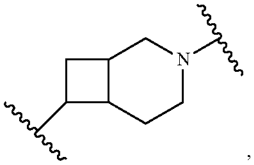, or
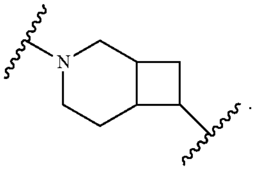.
In some embodiments, $F^2$ is
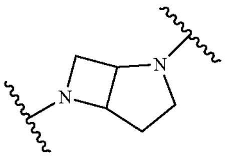, 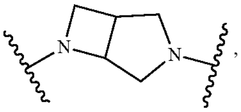,
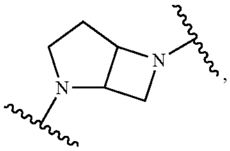, 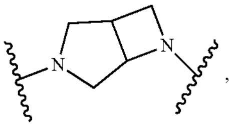, -continued
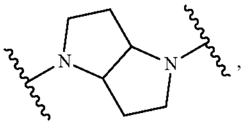
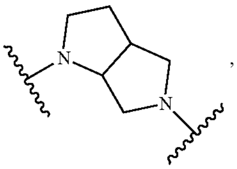
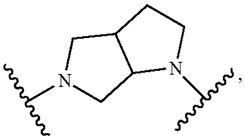
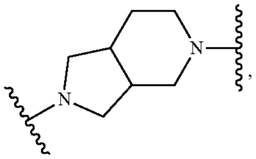
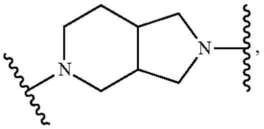
or
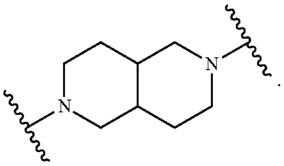
In some embodiments, the $C_2$-$C_9$ heterocyclyl is
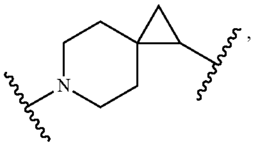
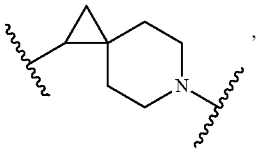
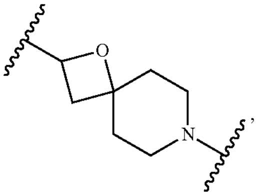
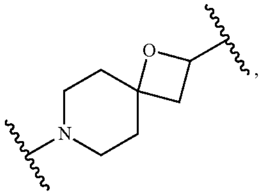
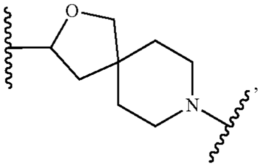
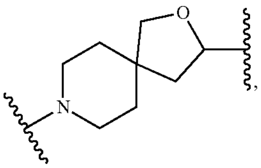
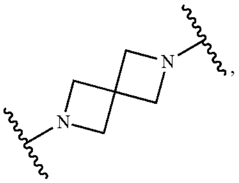
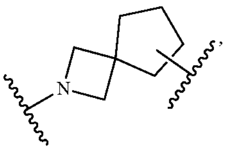
-continued
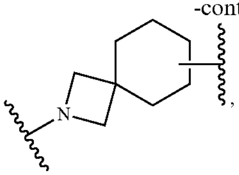
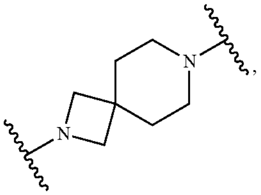
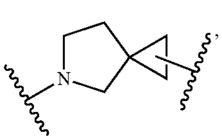
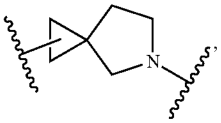
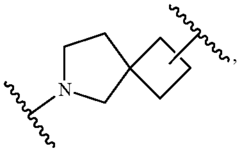
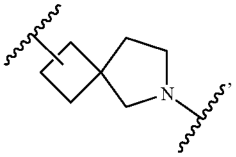
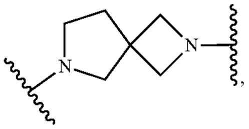
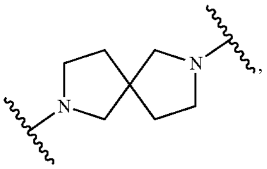
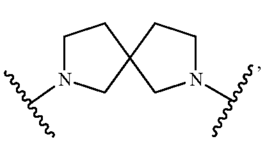
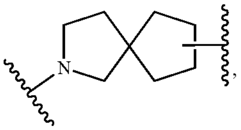
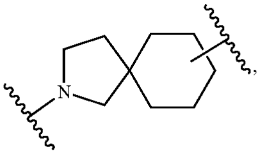
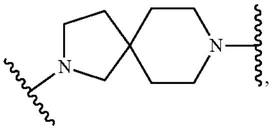
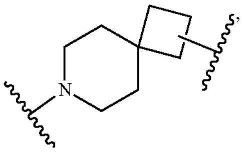
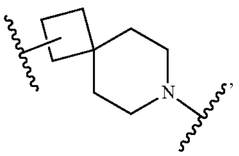
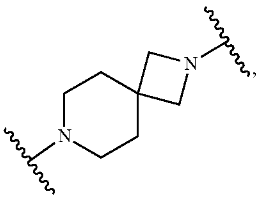
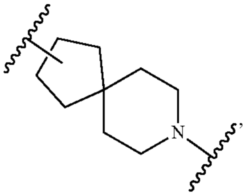
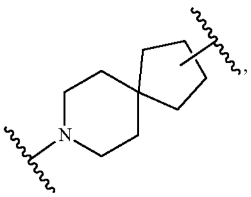
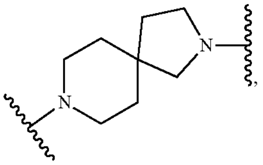

-continued
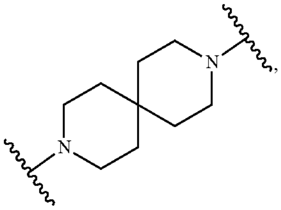,
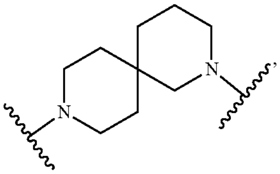,
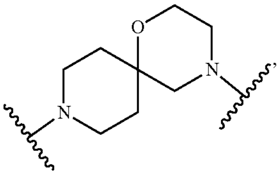, or
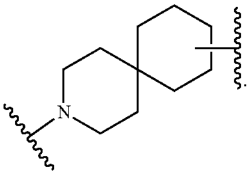.
In some embodiments, the $C_2$-$C_9$ heterocyclyl is
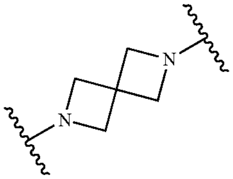,
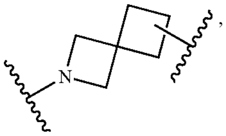,
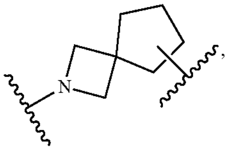,
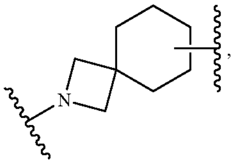,
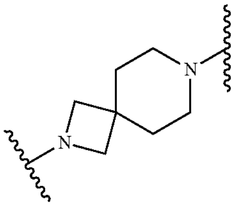,
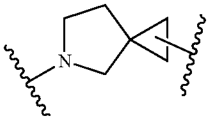,
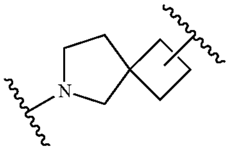,
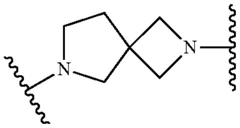,
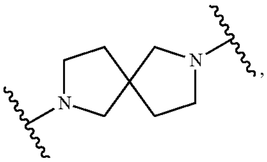,
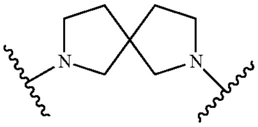,
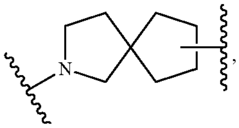,
-continued
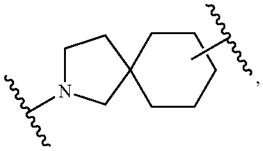,
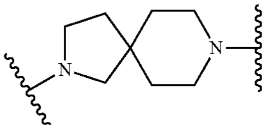,
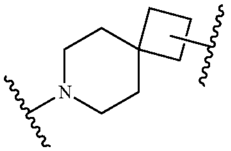,
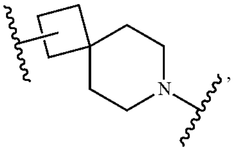,
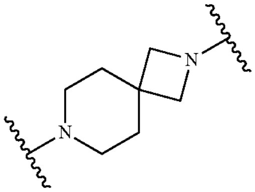,
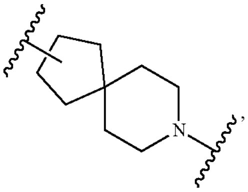,
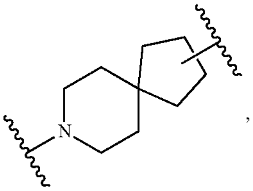,
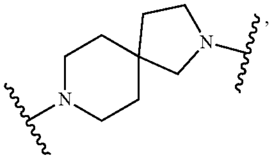,
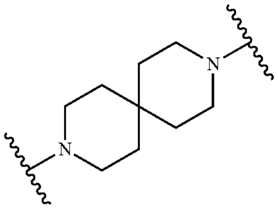,
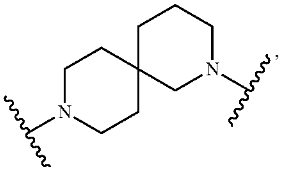,
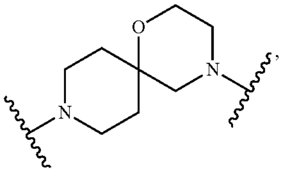, or
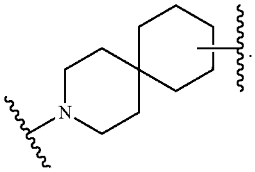.

In some embodiments, the $C_2$-$C_9$ heterocyclyl is
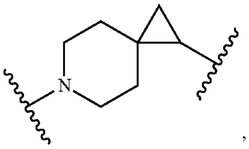
,
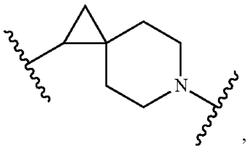
,
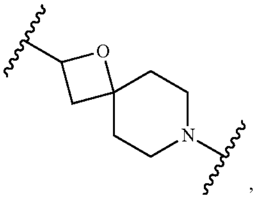
,
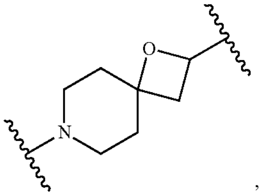
,
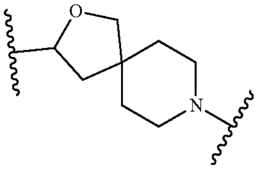
,
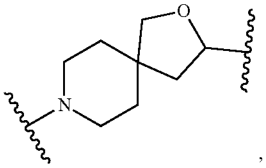
,
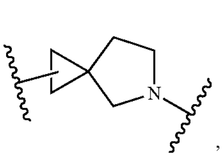
, or
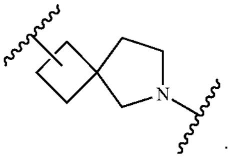
.
In some embodiments, $F^1$ is
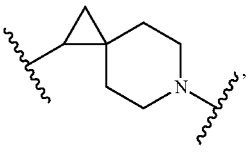
,
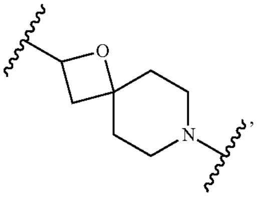
,
-continued
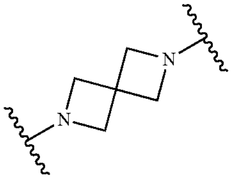
,
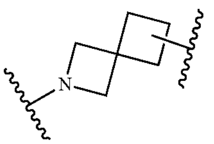
,
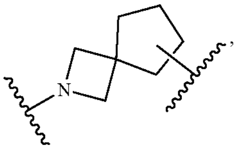
,
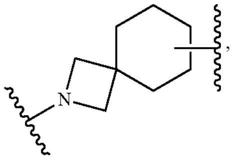
,
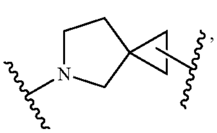
,
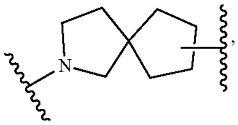
,
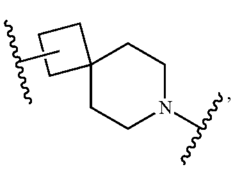
,
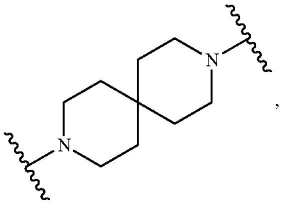
,
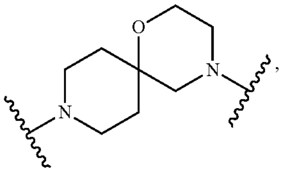
, or
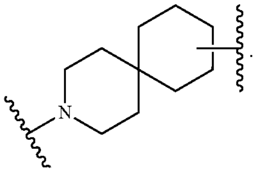
.
In some embodiments, $F^1$ is
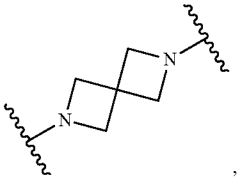
,
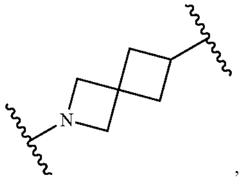
,
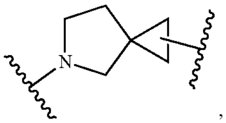
,
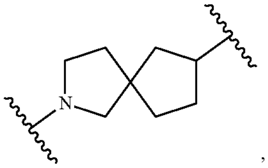
,
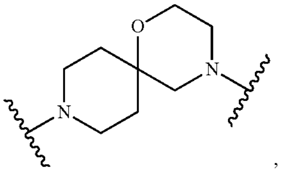
, or -continued
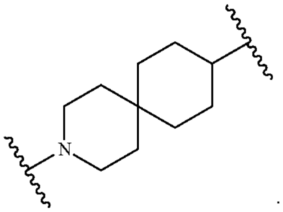
.
In some embodiments, $F^1$ is
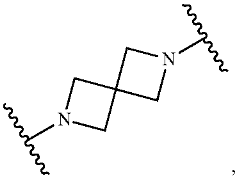
,
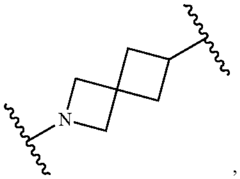
,
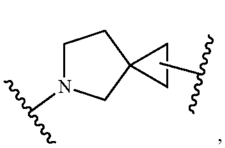
,
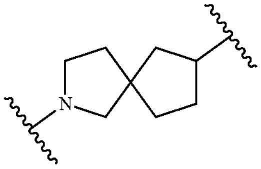
,
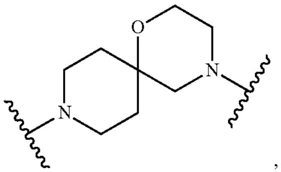
, or
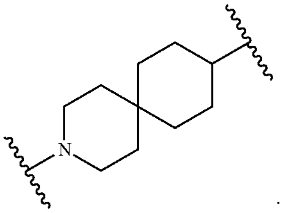
.
In some embodiments, $F^1$ is
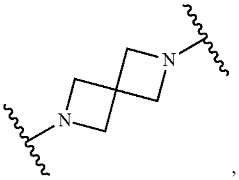
,
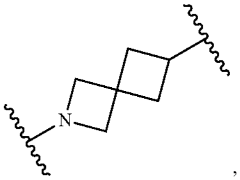
,
or
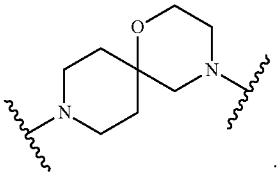
.
In some embodiments, $F^2$ is
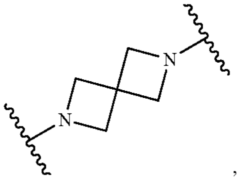
,
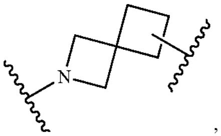
,
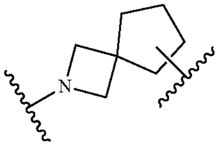
,
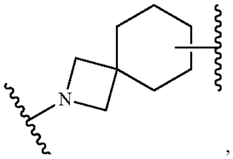
,
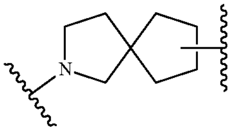
,
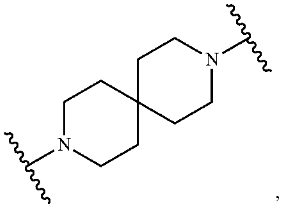
,
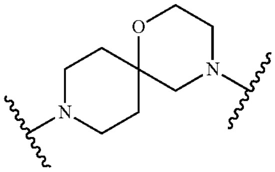
, or
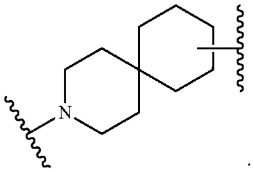
.
In some embodiments, $F^2$ is
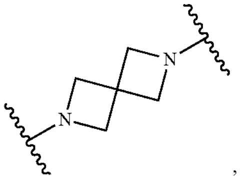
,
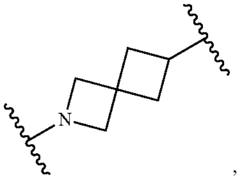
,
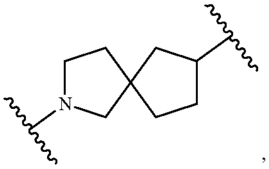
,
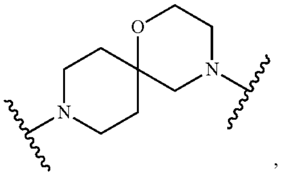
, or -continued

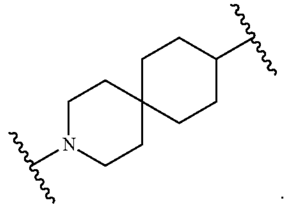

In some embodiments, $F^2$ is

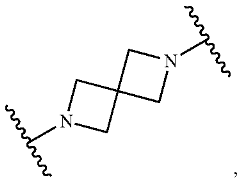,
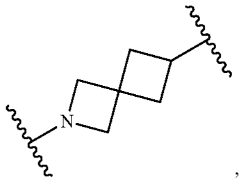,
or
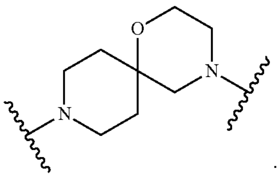.

In some embodiments, each of $F^1$, $F^2$, or $F^3$ is, independently, optionally substituted $C_6$-$C_{10}$ aryl.

In some embodiments, the $C_6$-$C_{10}$ aryl is

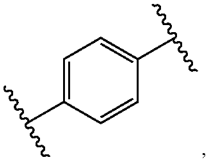,
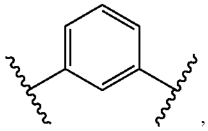, or
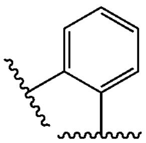.

In some embodiments, each of $F^1$, $F^2$, or $F^3$ is, independently, optionally substituted $C_2$-$C_9$ heteroaryl.

In some embodiments, the $C_2$-$C_9$ heteroaryl is

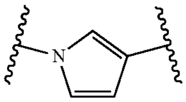, 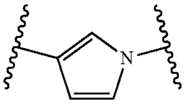,
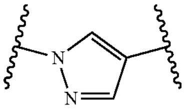, 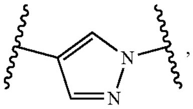,
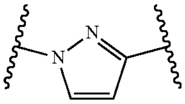, 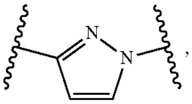,

-continued

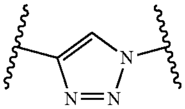, 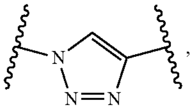,
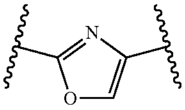, 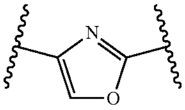,
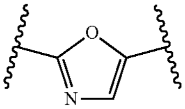, 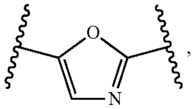,
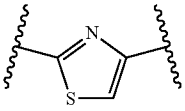, 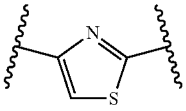,
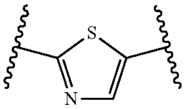, 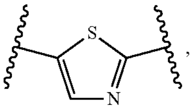,
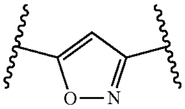, 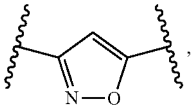,
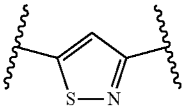, 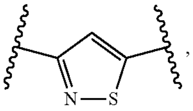,
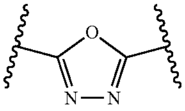, 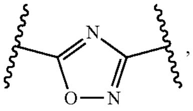,
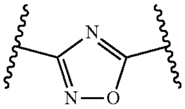, 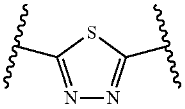,
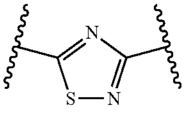, or 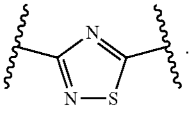.

In some embodiments, $F^2$ is

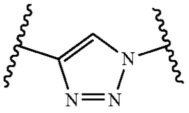 or 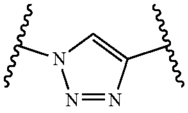.

In some embodiments, $F^2$ is

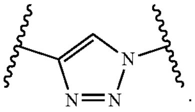 [SMILES: *c1cn(*)nn1].

In some embodiments, $C^3$ is
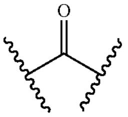
or
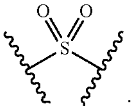
.
In some embodiments, $C^3$ is
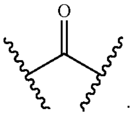 [SMILES: *C(*)=O]
.
In some embodiments, m is 1. In some embodiments, p is 1.
In some embodiments, the linker has the structure of
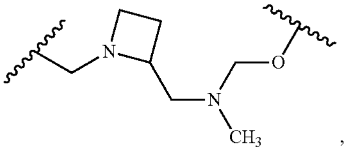
,
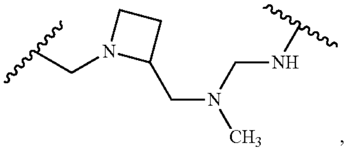
,
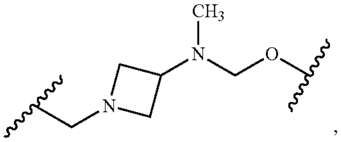
,
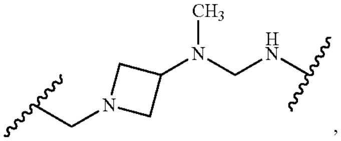
,
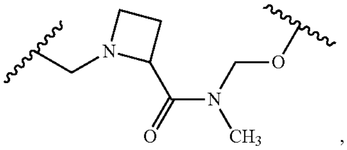
,
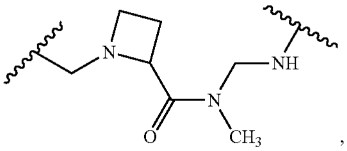
,
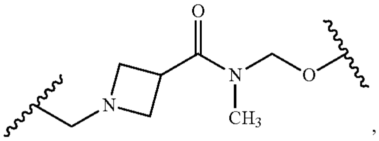
,
-continued
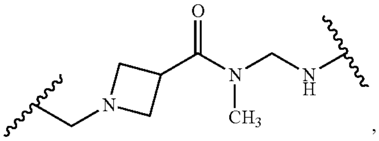
,
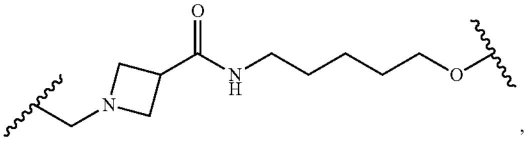
,
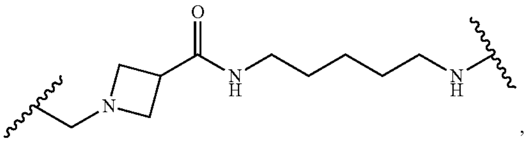
,
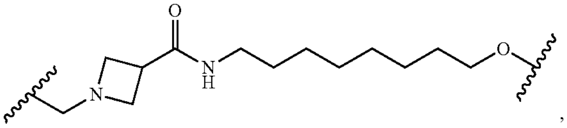
,
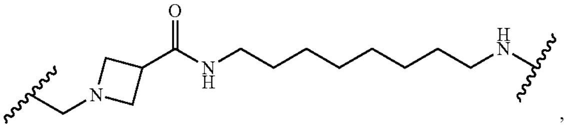
,
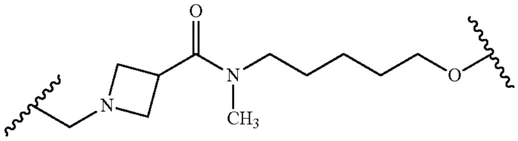
,
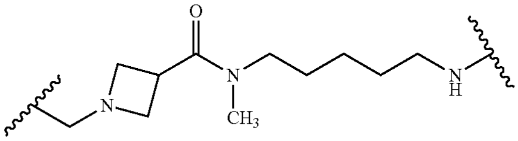
,
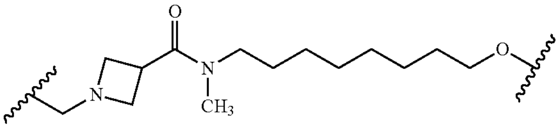
,
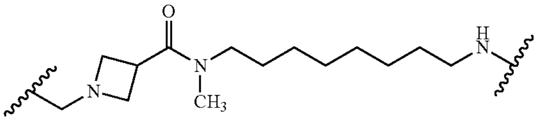
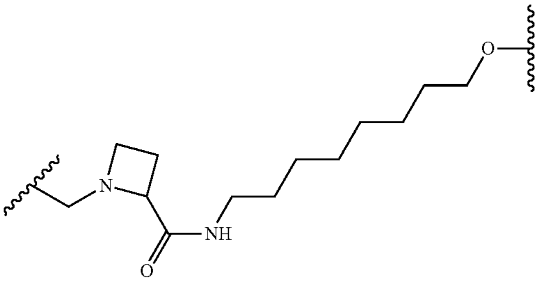
, -continued
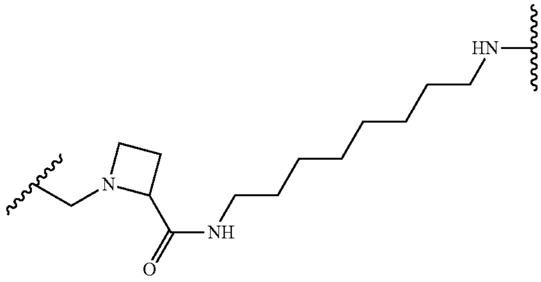
,
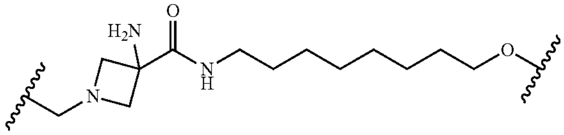
,
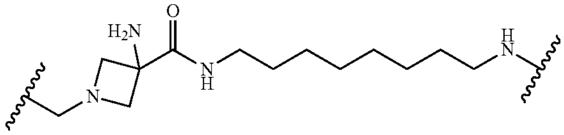
,
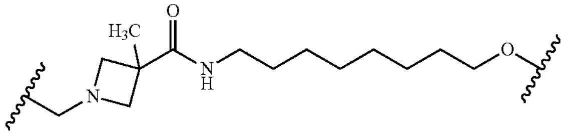
,
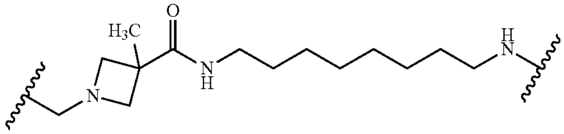
,
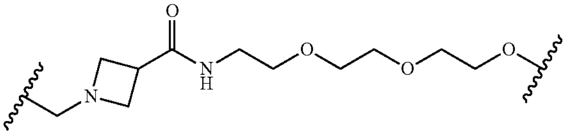
,
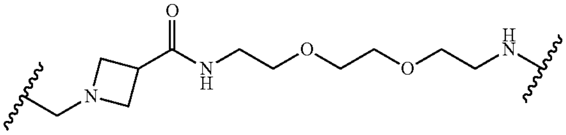
,
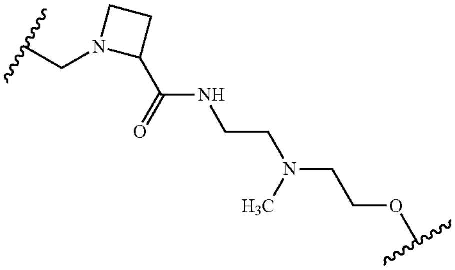
,
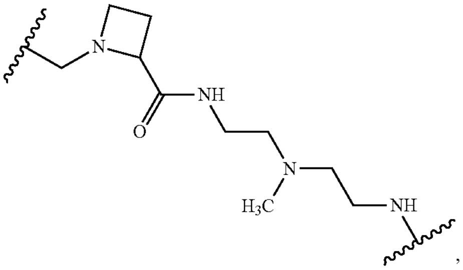
,
-continued
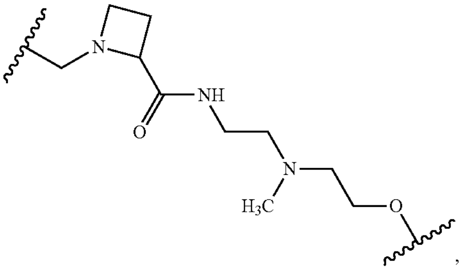
,
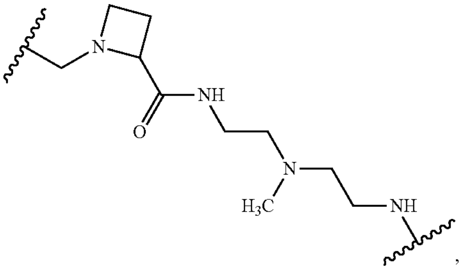
,
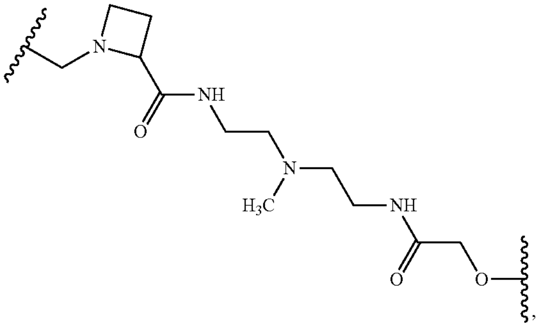
,
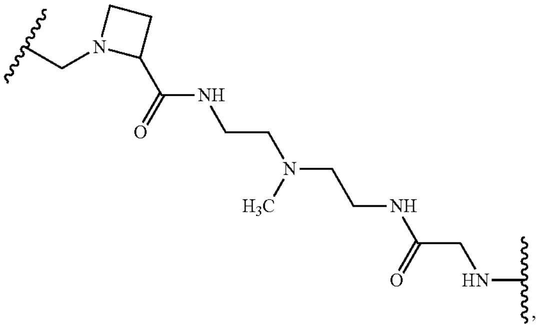
,
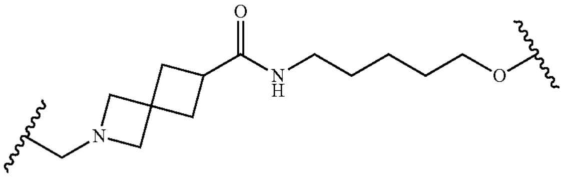
,
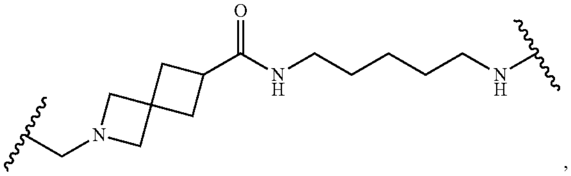
,
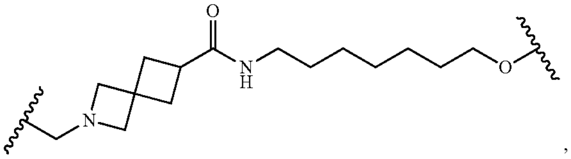
, -continued
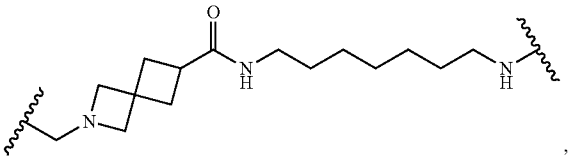
,
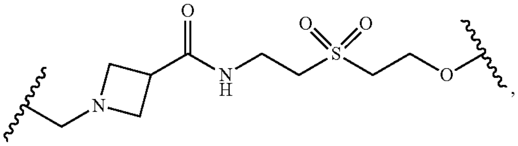
,
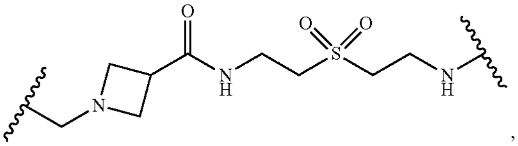
,
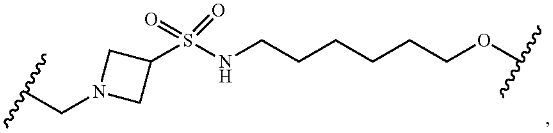
,
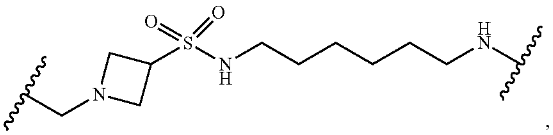
,
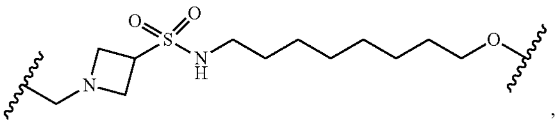
,
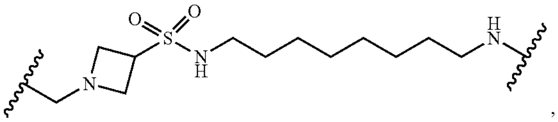
,
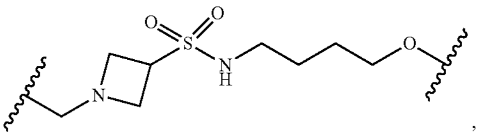
,
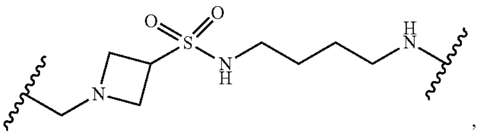
,
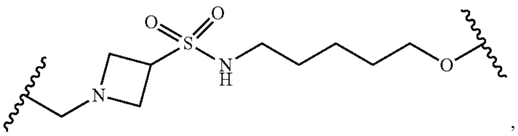
,
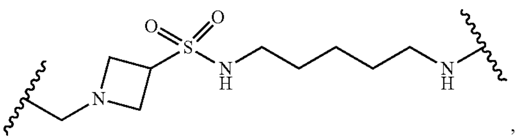
,
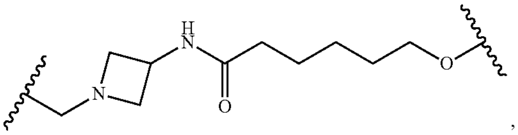
,
-continued
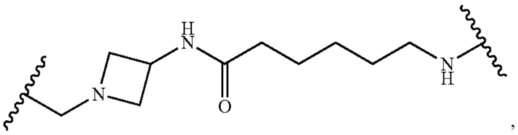
,
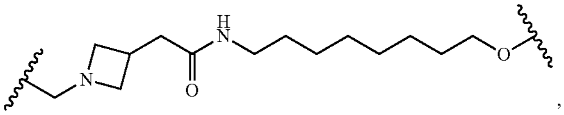
,
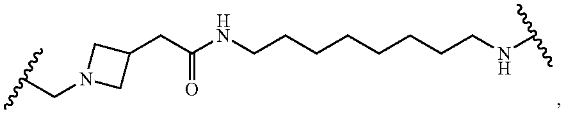
,
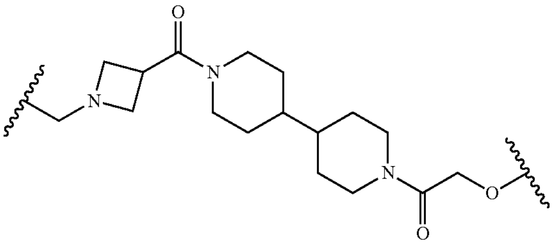
,
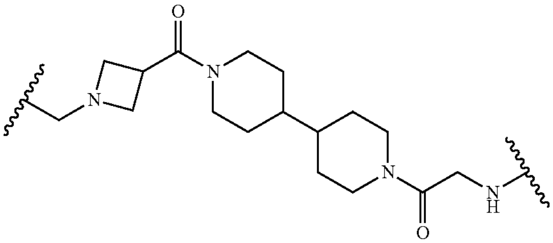
,
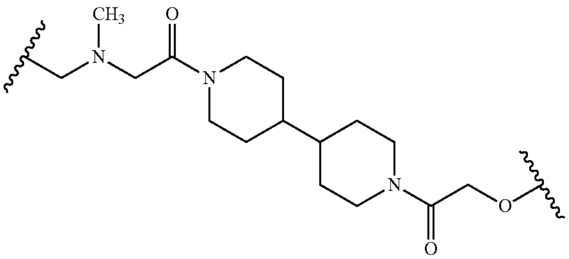
,
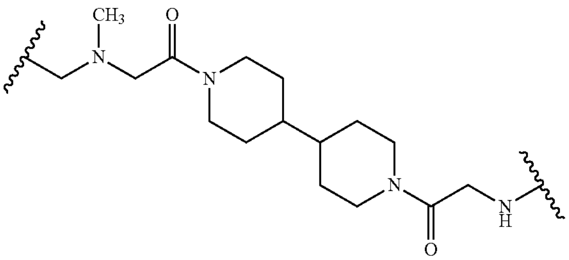
,
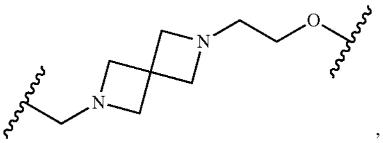
,
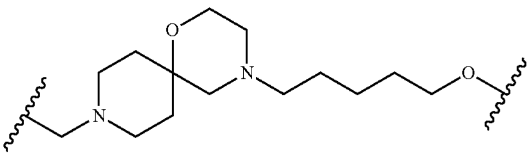
, -continued
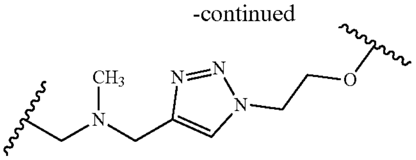
,
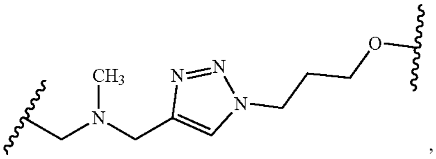
,
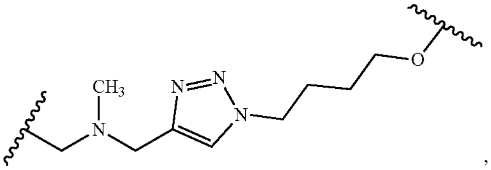
,
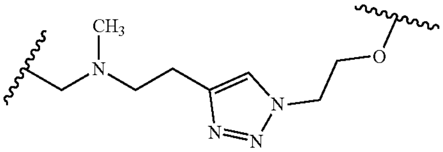
,
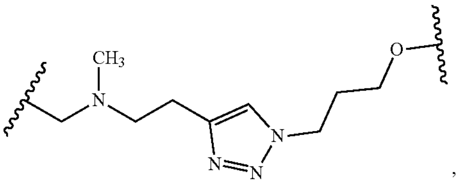
,
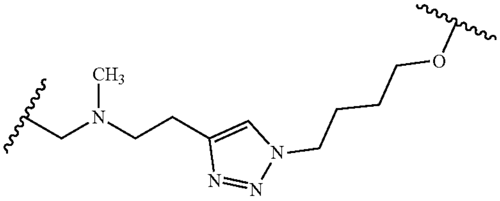
,
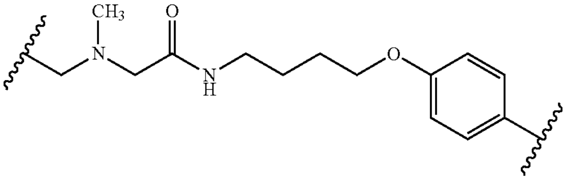
,
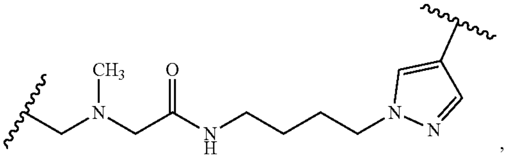
,
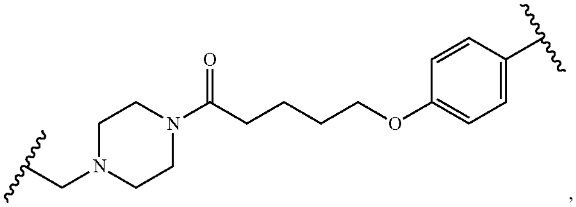
,
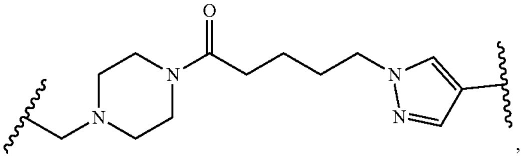
,
-continued
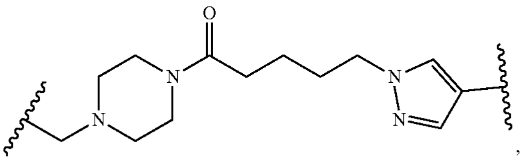
,
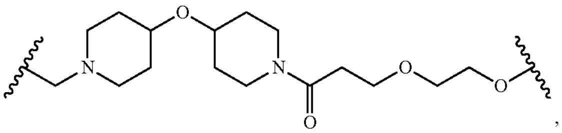
,
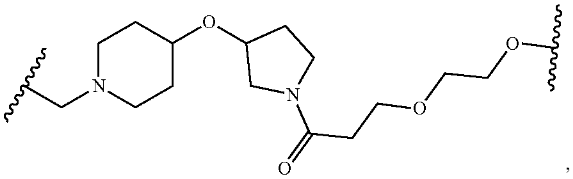
,
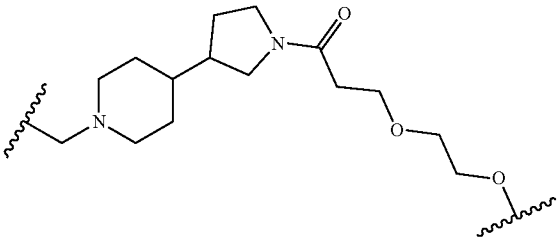
,
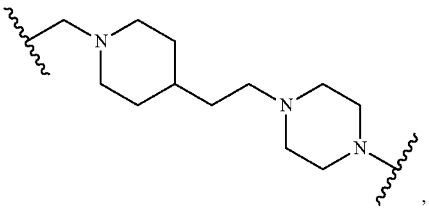
, or
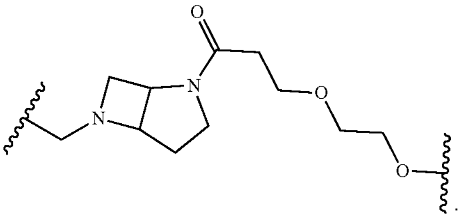
.
In some embodiments, the linker has the structure of
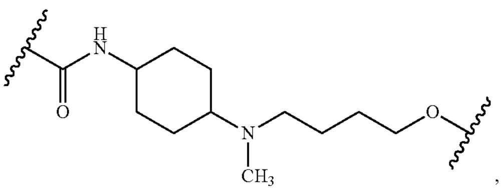
,
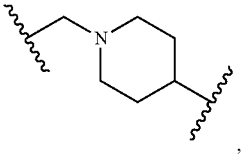
,
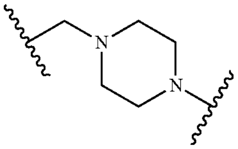
, -continued
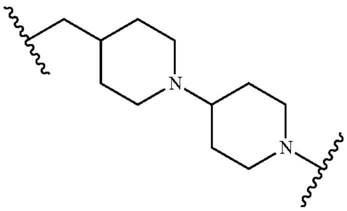
,
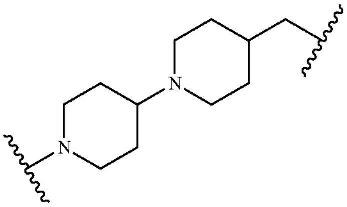
,
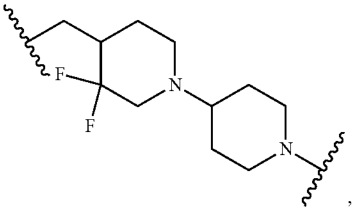
,
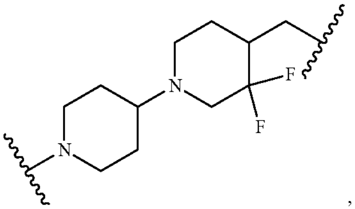
,
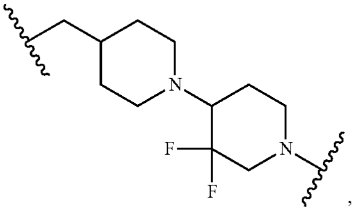
,
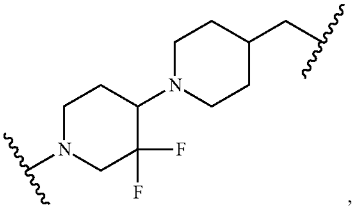
,
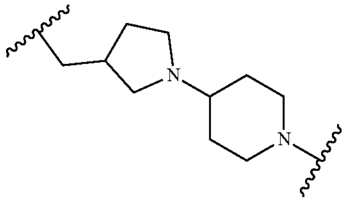
,
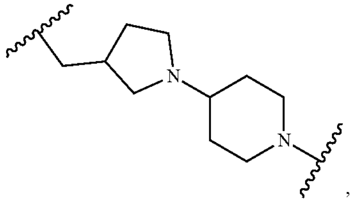
,
-continued
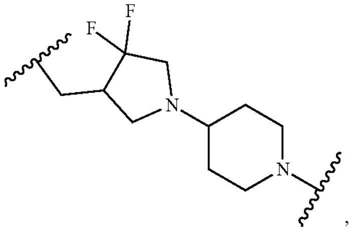
,
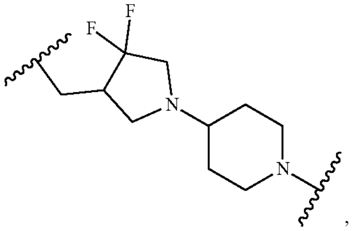
,
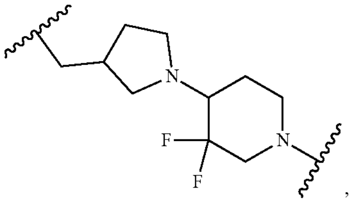
,
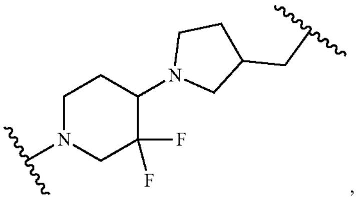
,
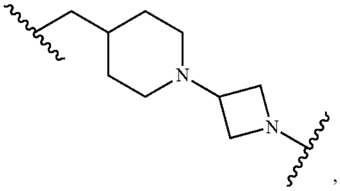
,
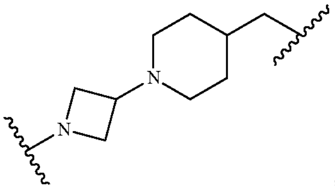
,
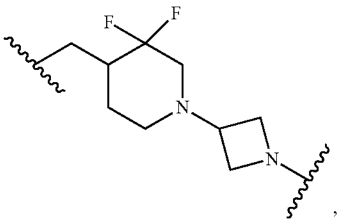
,
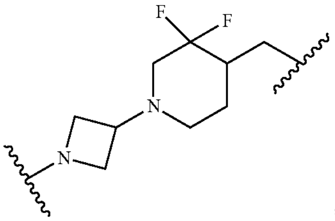
, -continued
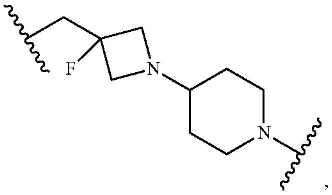
,
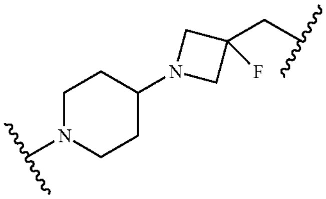
,
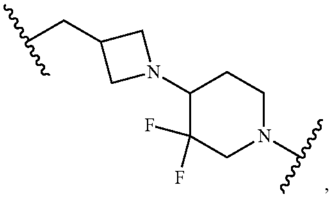
,
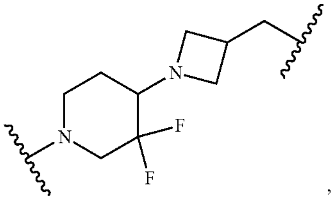
,
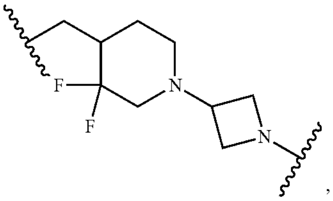
,
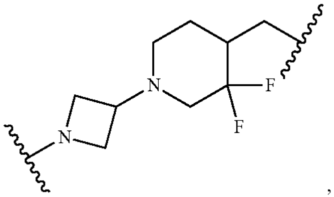
,
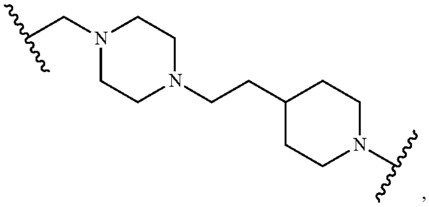
,
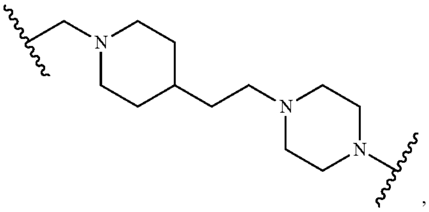
,
-continued
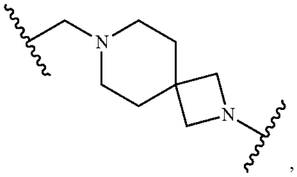
,
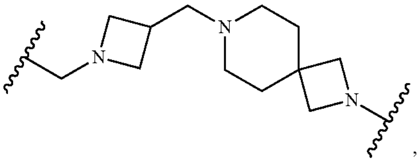
,
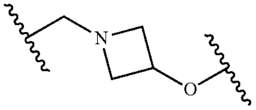
,
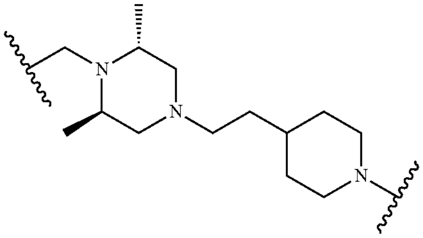
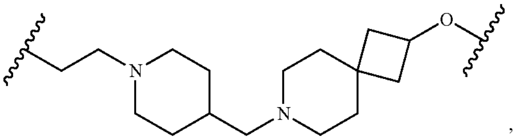
,
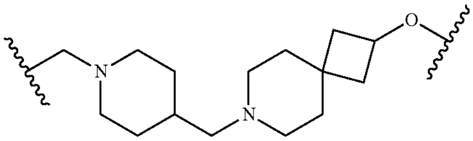
,
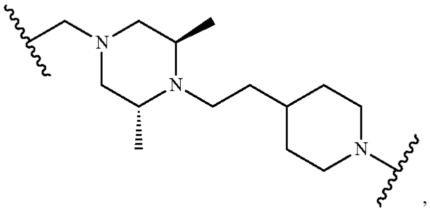
,
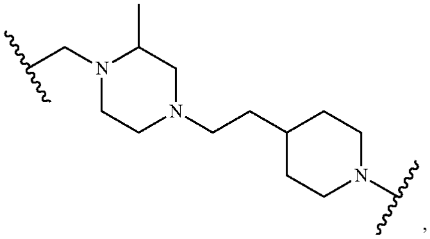
,
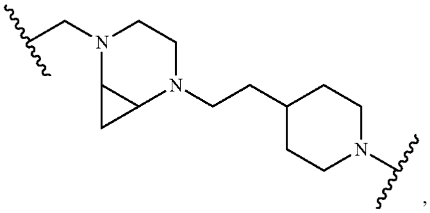
, -continued
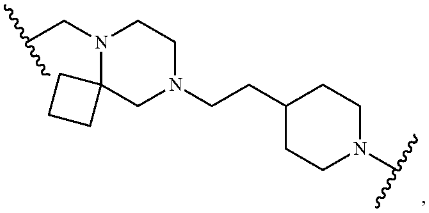
,
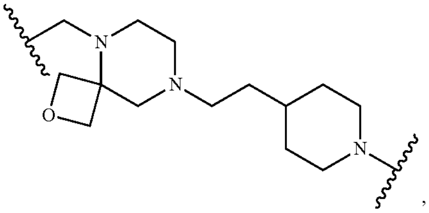
,
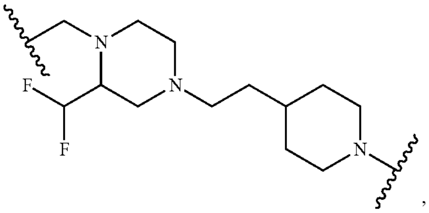
,
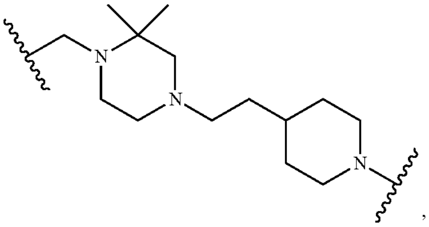
,
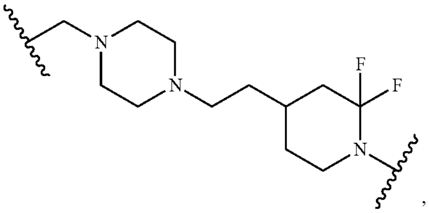
,
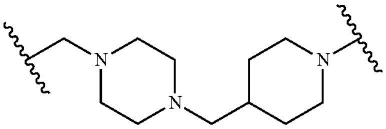
,
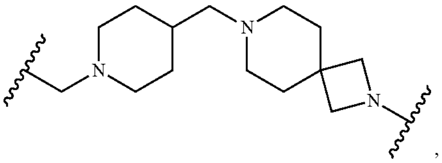
,
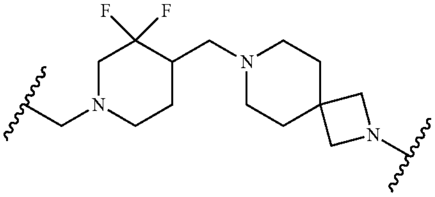
-continued
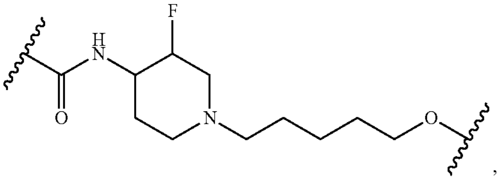
,
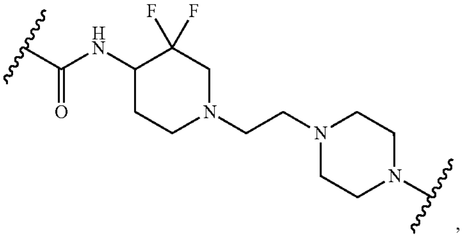
,
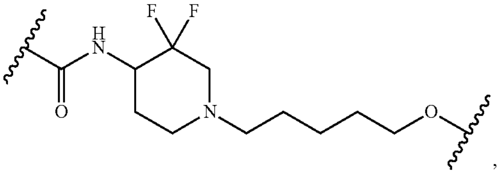
,
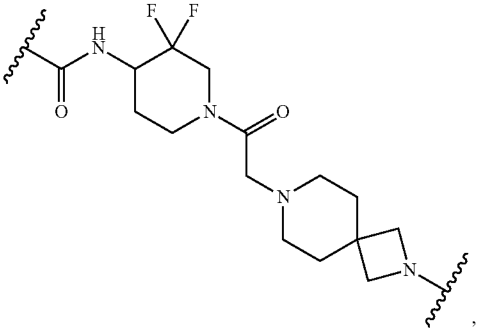
,
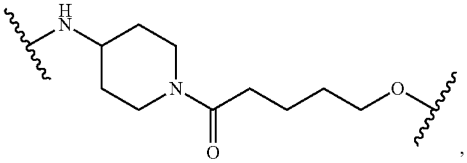
,
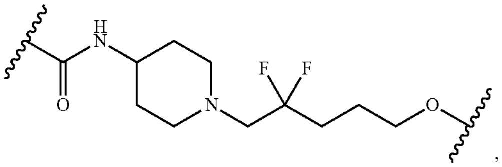
,
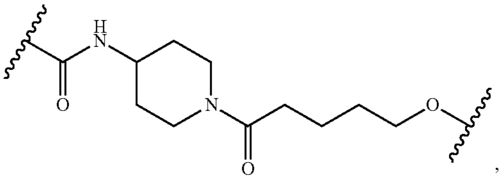
,
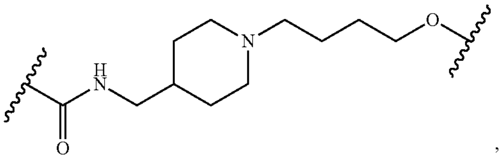
, -continued
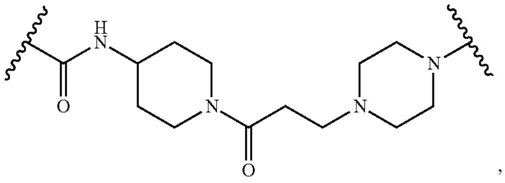
,
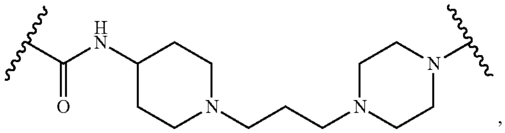
,
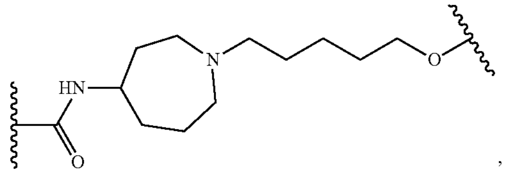
,
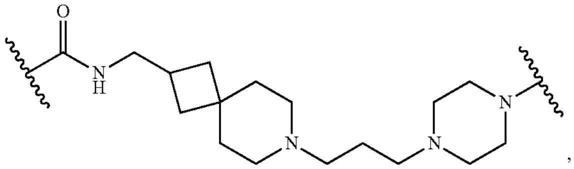
,
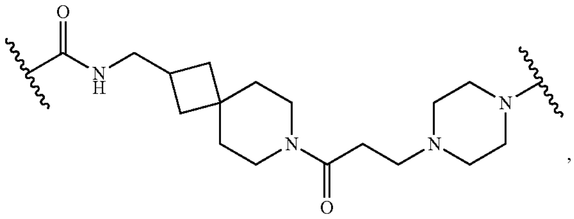
,
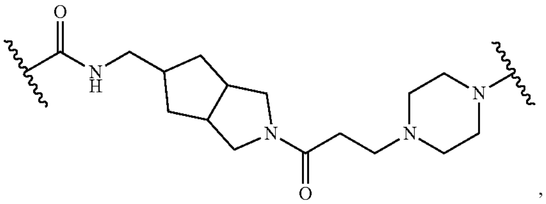
,
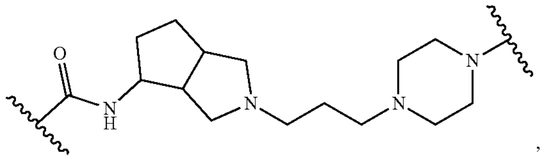
,
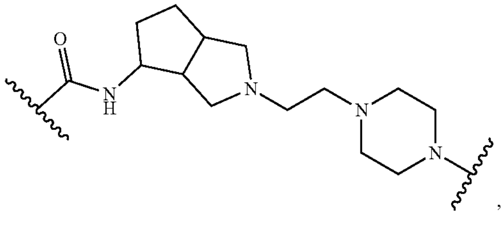
,
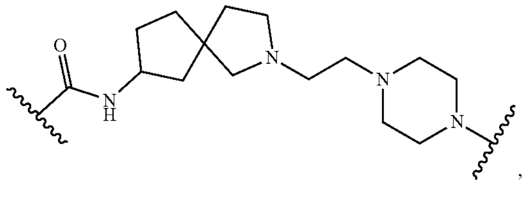
,
-continued
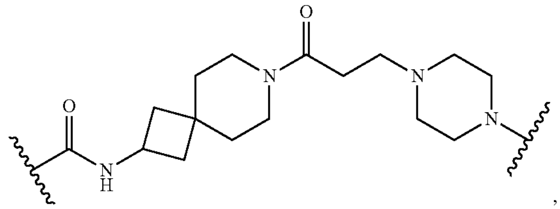
,
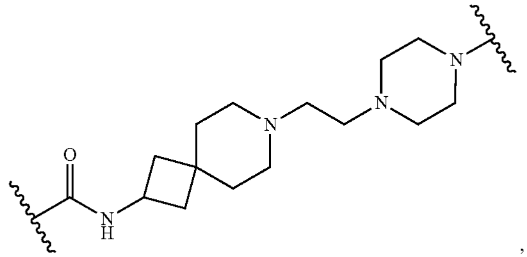
,
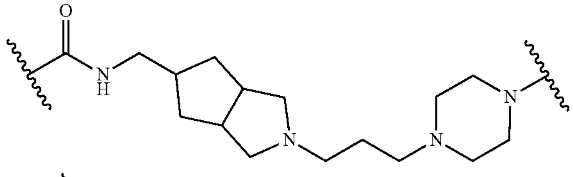
,
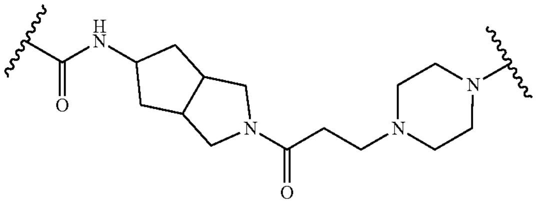
,
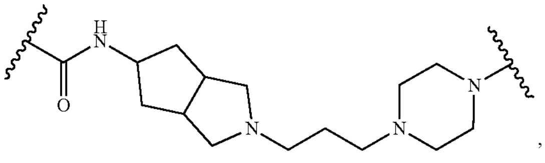
,
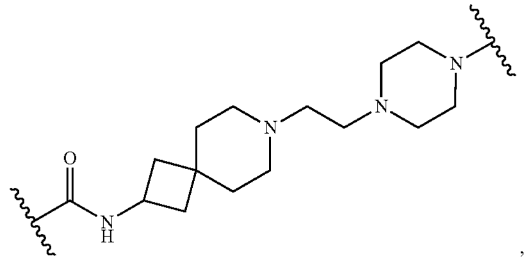
,
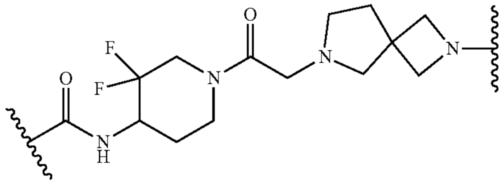
,
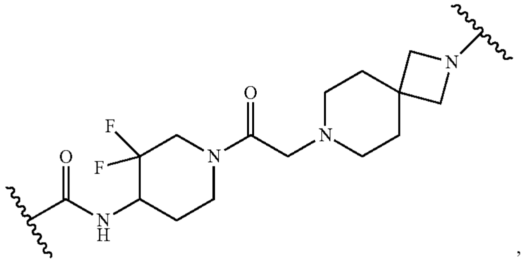
, -continued
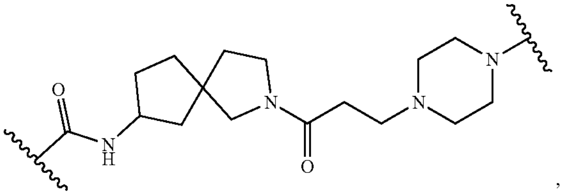
,
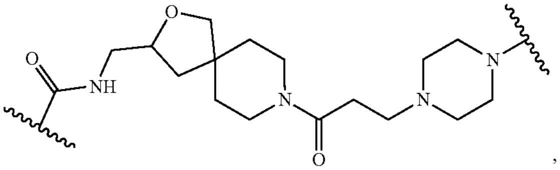
,
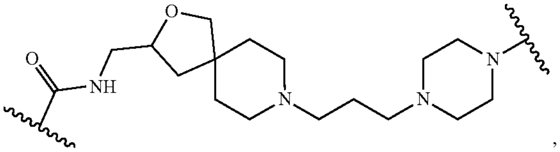
,
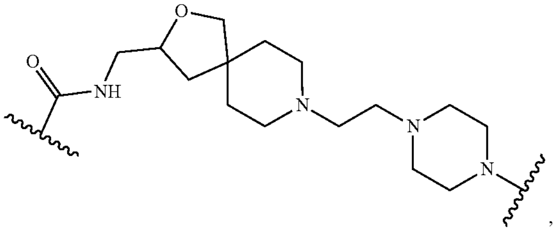
,
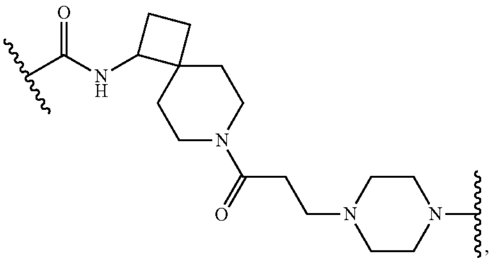
,
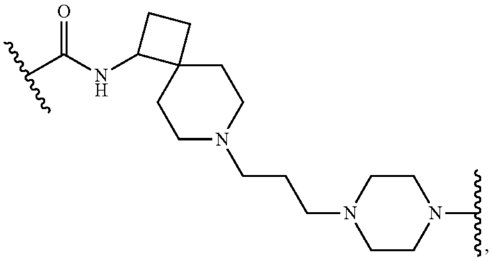
,
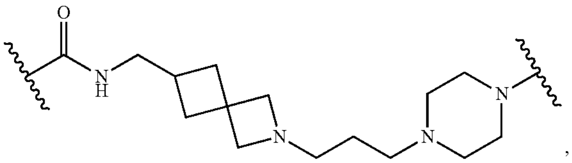
,
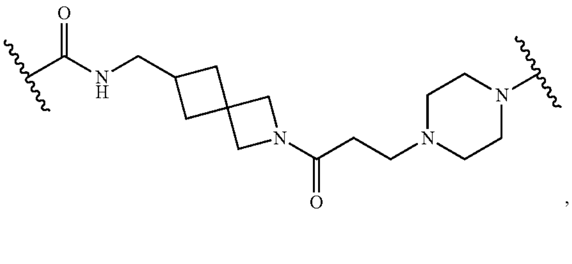
,
-continued
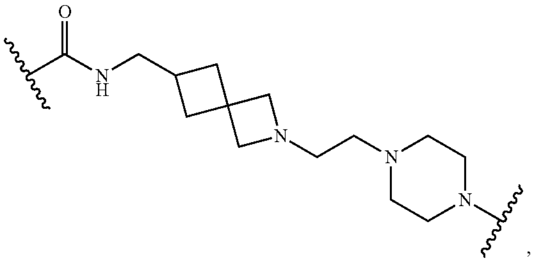
,
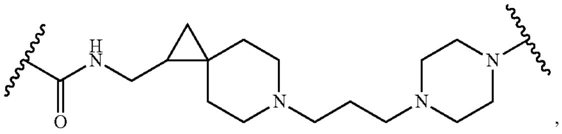
,
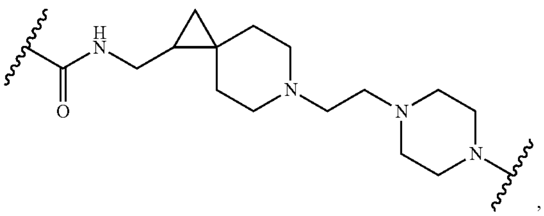
,
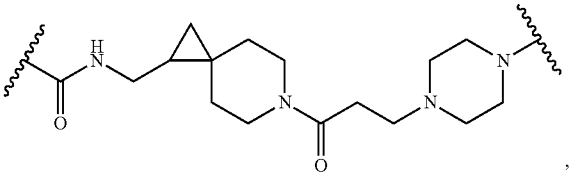
,
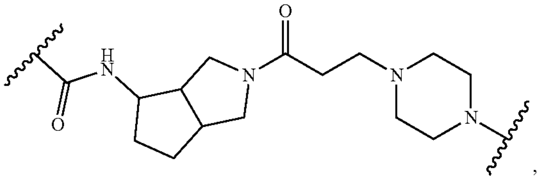
,
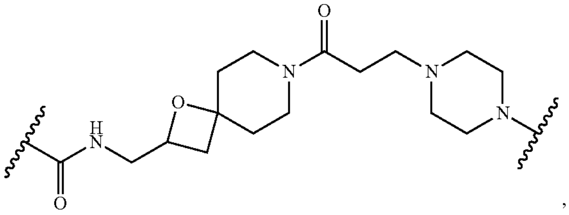
,
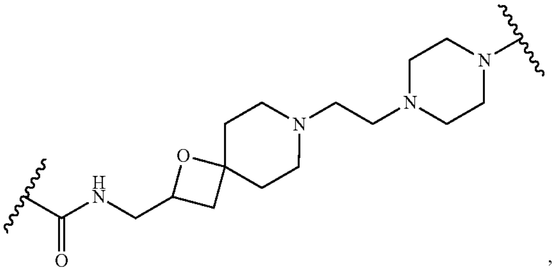
,
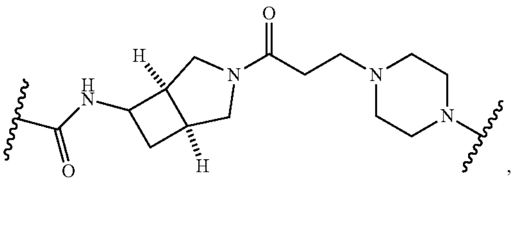
, -continued
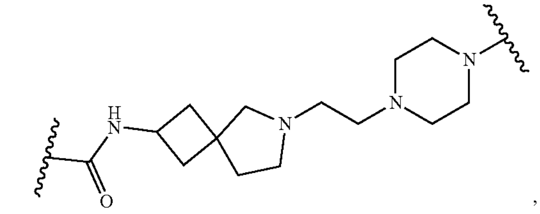
,
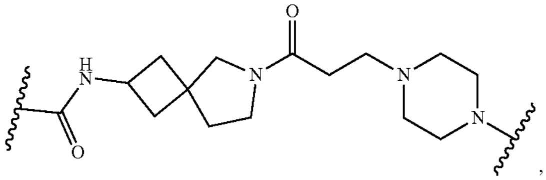
,
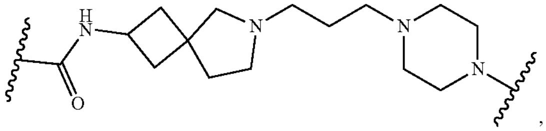
,
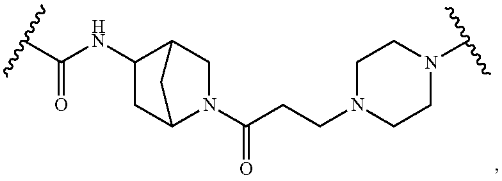
,
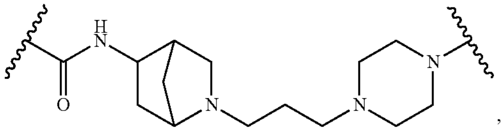
,
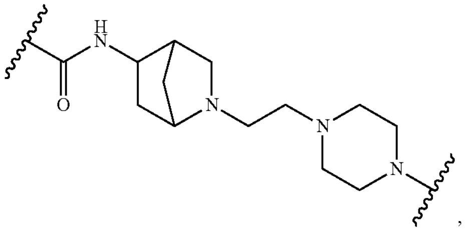
,
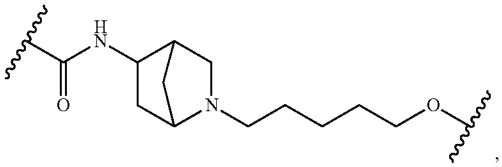
,
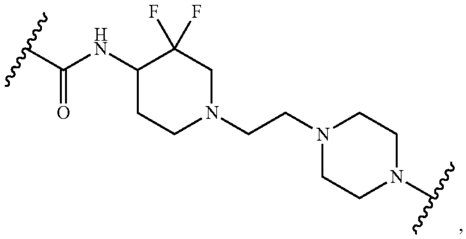
,
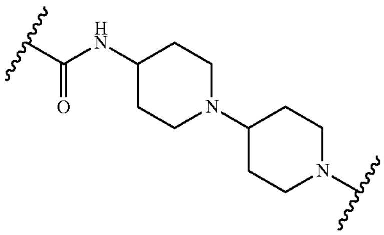
,
-continued
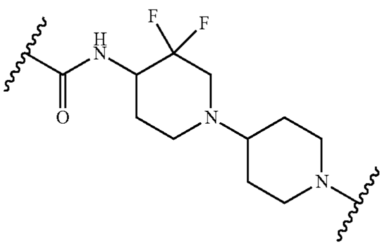
,
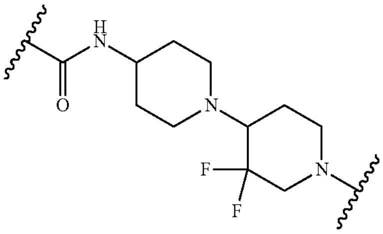
,
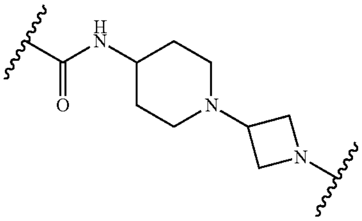
,
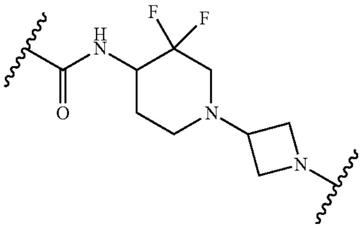
,
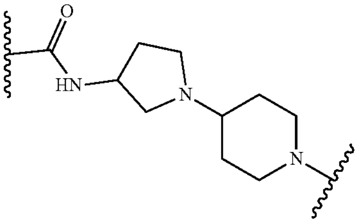
,
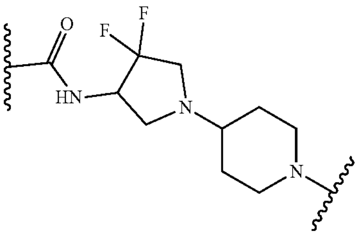
,
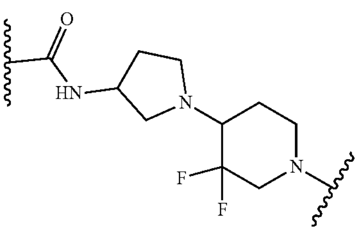
, -continued

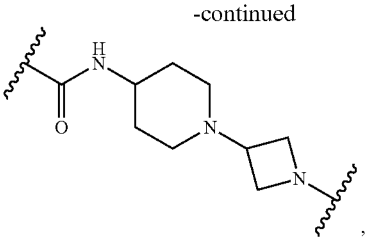

,

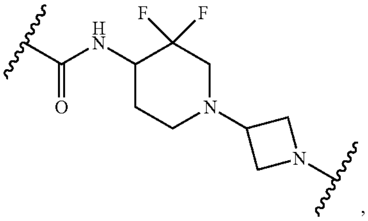

,

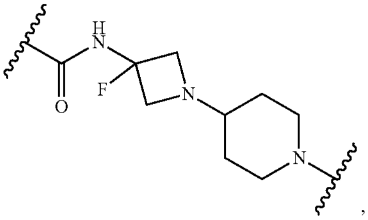

,

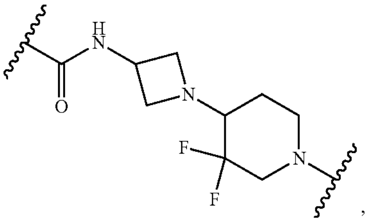

, or

-continued

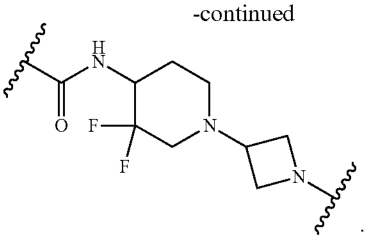

.

In some embodiments, the linker has the structure of

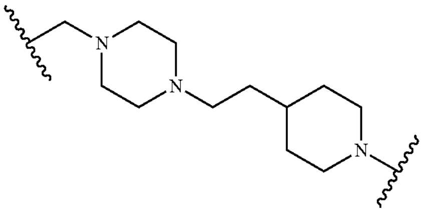

or

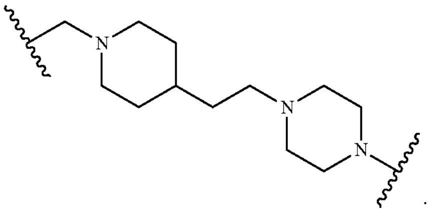

.

In some embodiments, the compound has the structure of any one of compounds D1-D11 in Table 1, or a pharmaceutically acceptable salt thereof.

In an aspect, the disclosure features a compound having the structure of any one of compounds D1-D11 in Table 1, or a pharmaceutically acceptable salt thereof.

TABLE 1

| Compounds D1-D11 of the Disclosure | |
|---|---|
| Compound No. | Structure |
| D1 | 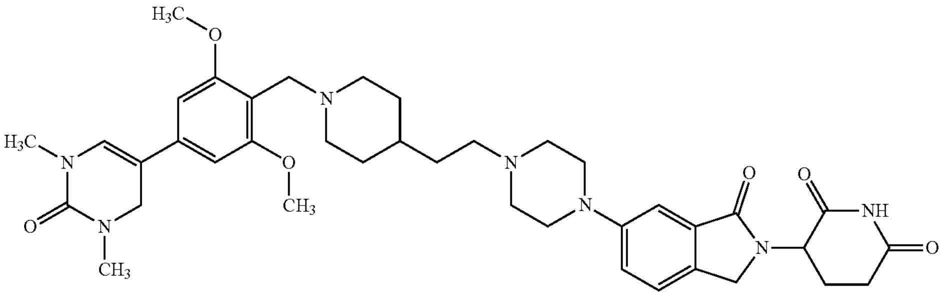 [SMILES: COc1cc(C2=CN(C)C(=O)N(C)C2)cc(OC)c1CN1CCC(CCN2CCN(c3ccc4c(c3)C(=O)N(C3CCC(=O)NC3=O)C4)CC2)CC1] |

TABLE 1-continued
| Compounds D1-D11 of the Disclosure | |
|---|---|
| Compound No. | Structure |
| D2 | 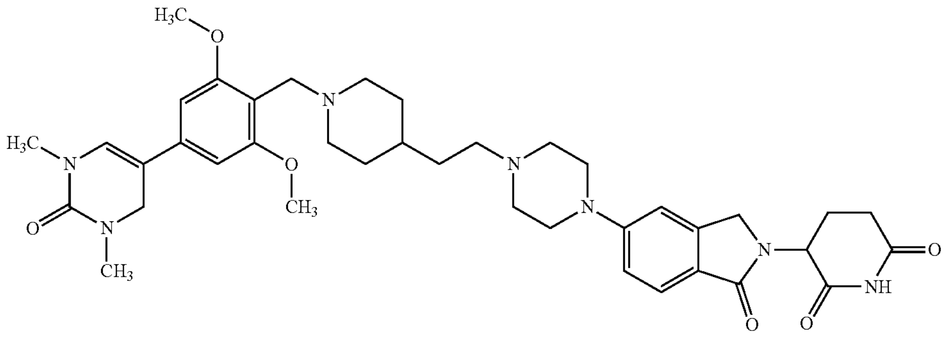 [SMILES: COc1cc(C2=CN(C)C(=O)N(C)C2)cc(OC)c1CN1CCC(CCN2CCN(c3ccc4c(c3)CN(C3CCC(=O)NC3=O)C4=O)CC2)CC1] |
| D3 | 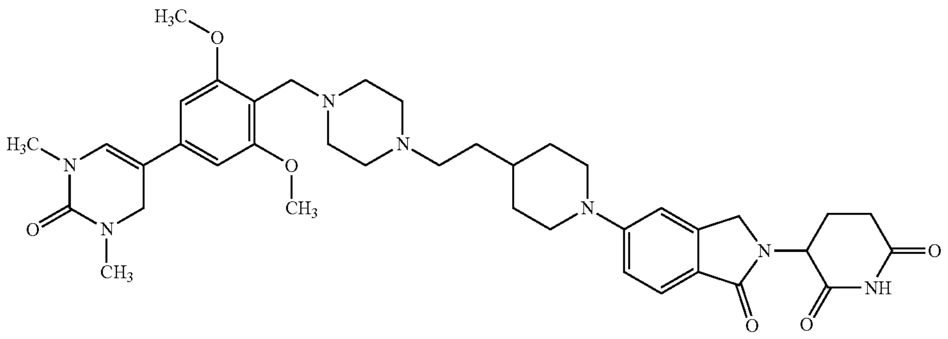 [SMILES: COc1cc(C2=CN(C)C(=O)N(C)C2)cc(OC)c1CN1CCN(CCC2CCN(c3ccc4c(c3)CN(C3CCC(=O)NC3=O)C4=O)CC2)CC1] |
| D4 | 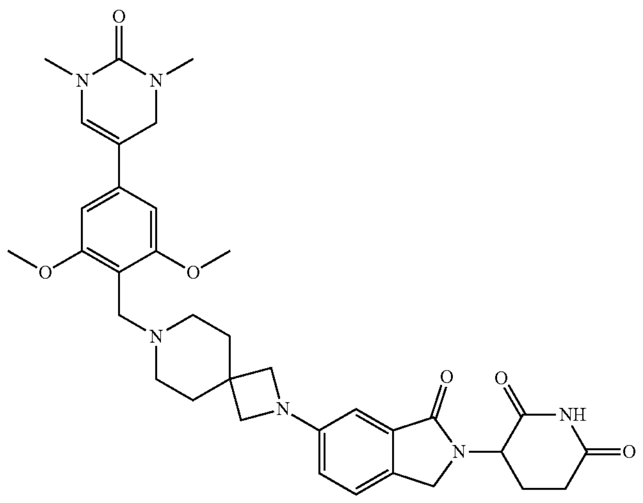 [SMILES: COc1cc(C2=CN(C)C(=O)N(C)C2)cc(OC)c1CN1CCC2(CC1)CN(c1ccc3c(c1)C(=O)N(C1CCC(=O)NC1=O)C3)C2] |

TABLE 1-continued
| Compounds D1-D11 of the Disclosure | |
|---|---|
| Compound No. | Structure |
| D5 | 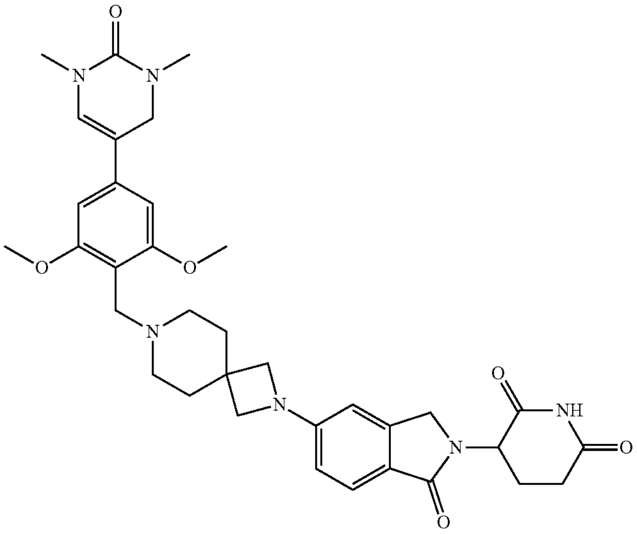 [SMILES: COc1cc(C2=CN(C)C(=O)N(C)C2)cc(OC)c1CN1CCC2(CC1)CN(c1ccc3c(c1)CN(C1CCC(=O)NC1=O)C3=O)C2] |
| D6 | 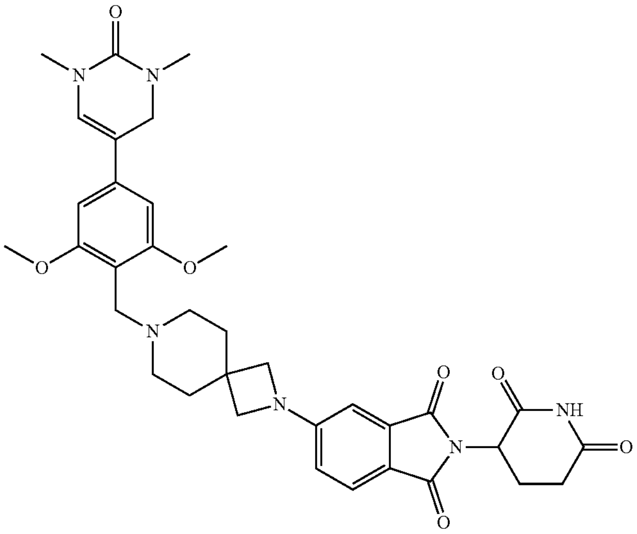 [SMILES: COc1cc(C2=CN(C)C(=O)N(C)C2)cc(OC)c1CN1CCC2(CC1)CN(c1ccc3c(c1)C(=O)N(C1CCC(=O)NC1=O)C3=O)C2] |

TABLE 1-continued
| Compounds D1-D11 of the Disclosure | |
|---|---|
| Compound No. | Structure |
| D7 | 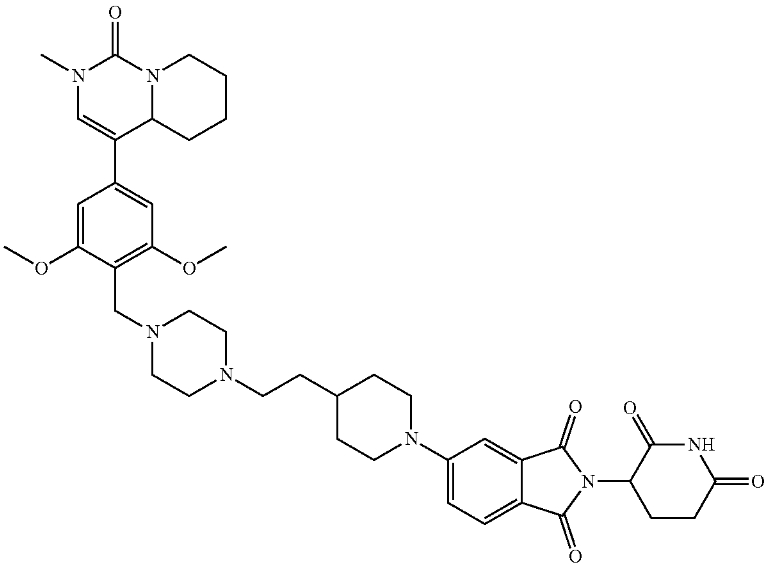 [SMILES: COc1cc(C2=CN(C)C(=O)N3CCCCC23)cc(OC)c1CN1CCN(CCC2CCN(c3ccc4c(c3)C(=O)N(C3CCC(=O)NC3=O)C4=O)CC2)CC1] |
| D8 | 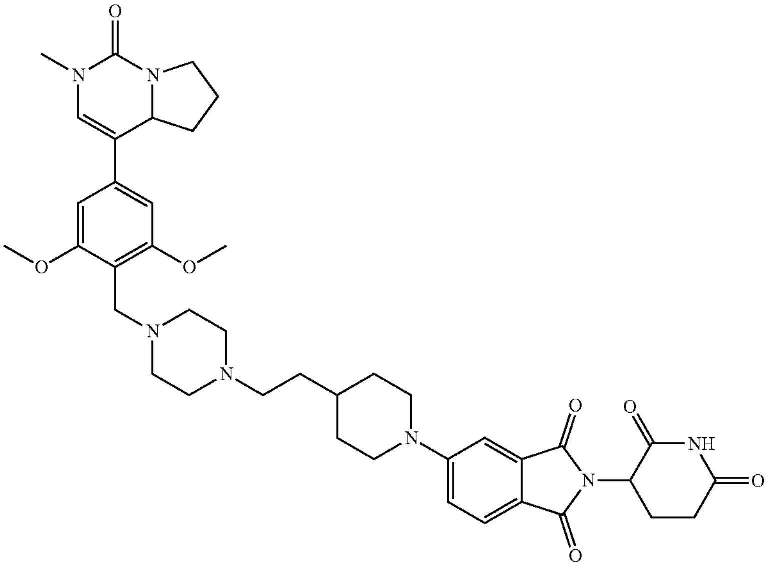 [SMILES: COc1cc(C2=CN(C)C(=O)N3CCCC23)cc(OC)c1CN1CCN(CCC2CCN(c3ccc4c(c3)C(=O)N(C3CCC(=O)NC3=O)C4=O)CC2)CC1] |

TABLE 1-continued
| Compounds D1-D11 of the Disclosure | |
|---|---|
| Compound No. | Structure |
| D9 | 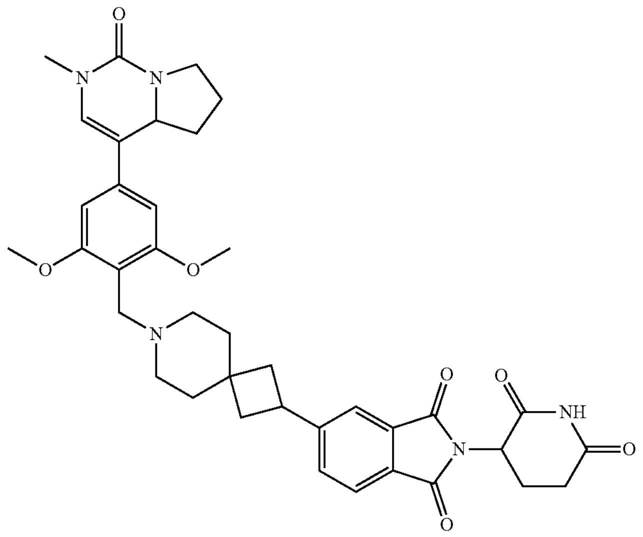 [SMILES: COc1cc(C2=CN(C)C(=O)N3CCCC23)cc(OC)c1CN1CCC2(CC1)CC(c1ccc3c(c1)C(=O)N(C1CCC(=O)NC1=O)C3=O)C2] |
| D10 | 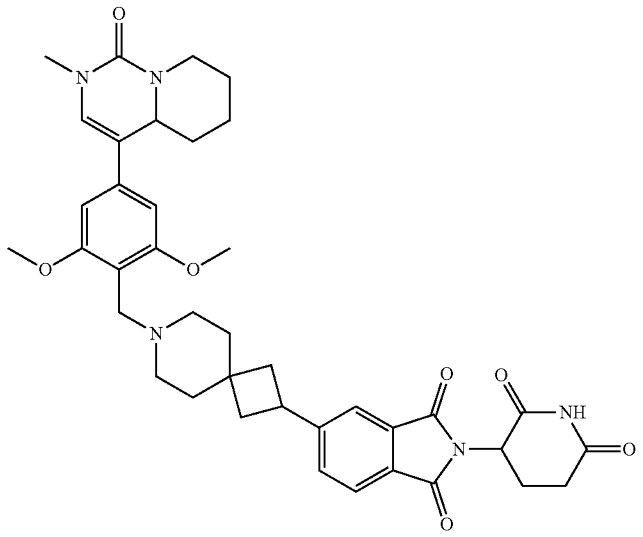 [SMILES: COc1cc(C2=CN(C)C(=O)N3CCCCC23)cc(OC)c1CN1CCC2(CC1)CC(c1ccc3c(c1)C(=O)N(C1CCC(=O)NC1=O)C3=O)C2] |

TABLE 1-continued

| Compounds D1-D11 of the Disclosure | |
|---|---|
| Compound No. | Structure |
| D11 | 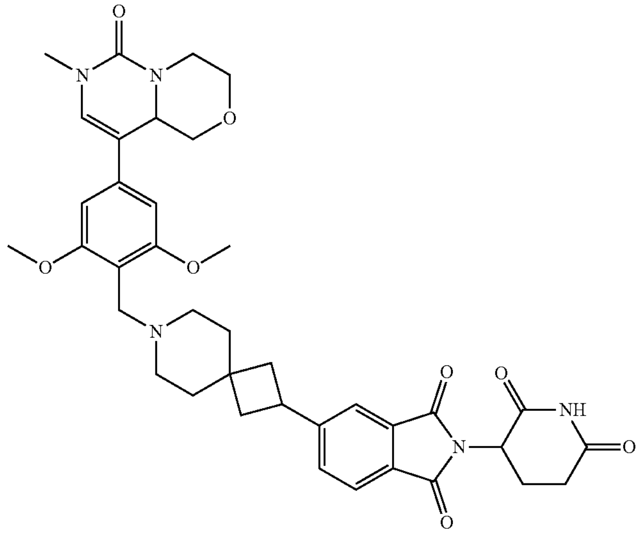 [SMILES: COc1cc(C2=CN(C)C(=O)N3CCOCC23)cc(OC)c1CN1CCC2(CC1)CC(c1ccc3c(c1)C(=O)N(C1CCC(=O)NC1=O)C3=O)C2] |

In another aspect, the disclosure features a pharmaceutical composition including any of the foregoing compounds, or pharmaceutically acceptable salts thereof, and a pharmaceutically acceptable excipient.

In an aspect, the disclosure features a method of inhibiting the level and/or activity of BRD9 in a cell, the method involving contacting the cell with an effective amount of any of the foregoing compounds, or pharmaceutically acceptable salts thereof, or a pharmaceutical composition thereof.

In another aspect, the disclosure features a method of reducing the level and/or activity of BRD9 in a cell, the method involving contacting the cell with an effective amount of any of the foregoing compounds, or pharmaceutically acceptable salts thereof, or a pharmaceutical composition thereof.

In some embodiments, the cell is a cancer cell.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In an aspect, the disclosure features a method of treating a BAF complex-related disorder in a subject in need thereof, the method involving administering to the subject an effective amount of any of the foregoing compounds, or pharmaceutically acceptable salts thereof, or a pharmaceutical composition thereof. In some embodiments, the BAF complex-related disorder is cancer. In some embodiments, the BAF complex-related disorder is infection.

In another aspect, the disclosure features a method of treating an SS18-SSX fusion protein-related disorder in a subject in need thereof, the method involving administering to the subject an effective amount of any of the foregoing compounds, or pharmaceutically acceptable salts thereof, or a pharmaceutical composition thereof. In some embodiments, the SS18-SSX fusion protein-related disorder is cancer. In some embodiments, the SS18-SSX fusion protein-related disorder is infection. In some embodiments of any of the foregoing methods, the SS18-SSX fusion protein is a SS18-SSX1 fusion protein, a SS18-SSX2 fusion protein, or a SS18-SSX4 fusion protein.

In yet another aspect, the disclosure features a method of treating a BRD9-related disorder in a subject in need thereof, the method involving administering to the subject an effective amount of any of the foregoing compounds, or pharmaceutically acceptable salts thereof, or a pharmaceutical composition thereof. In some embodiments, the BRD9-related disorder is cancer. In some embodiments, the BRD9-related disorder is infection.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In some embodiments, the infection is viral infection (e.g., an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)); Flaviviridae family (e.g. hepatitis C virus (HCV)); Adenoviridae family (e.g. Human Adenovirus); Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus); Papillomaviridae family (e.g. Human Papillomavirus (HPV, HPV E1)); Parvoviridae family (e.g. Parvovirus B19); Polyomaviridae family (e.g. JC virus and BK virus); Paramyxoviridae family (e.g. Measles virus); or Togaviridae family (e.g. Rubella virus)). In some embodiments, the disorder is Coffin Siris, Neurofibromatosis (e.g., NF-1, NF-2, or Schwannomatosis), or Multiple Meningioma. In an aspect, the disclosure features a method of treating a cancer in a subject in need thereof, the method including administering to the subject an effective amount of any of the foregoing compounds, or pharmaceutically acceptable salts thereof, or any of the foregoing pharmaceutical compositions.

In some embodiments, the cancer is squamous cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, a sarcoma (e.g., a soft tissue sarcoma, synovial sarcoma, Ewing's sarcoma, osteosarcoma, rhabdomyosarcoma, adult fibrosarcoma, alveolar soft-part sarcoma, angiosarcoma, clear cell sarcoma, desmoplastic small round cell tumor, epithelioid sarcoma, fibromyxoid sarcoma, gastrointestinal stromal tumor, Kaposi sarcoma, liposarcoma, leiomyosarcoma, malignant mesenchymoma malignant peripheral nerve sheath tumors, myxofibrosarcoma, low-grade rhabdomyosarcoma), non-small cell lung cancer (e.g., squamous or adenocarcinoma), stomach cancer, or breast cancer. In some embodiments, the cancer is a malignant, rhabdoid tumor, a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is a sarcoma (e.g., synovial sarcoma or Ewing's sarcoma), non-small cell lung cancer (e.g., squamous or adenocarcinoma), stomach cancer, or breast cancer. In some embodiments, the cancer is sarcoma (e.g., synovial sarcoma or Ewing's sarcoma). In some embodiments, the sarcoma is synovial sarcoma.

In another aspect, the disclosure features a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g. Human Papillomavirus (HPV, HPV E1)), Parvoviridae family (e.g. Parvovirus B19), Polyomaviridae family (e.g. JC virus and BK virus), Paramyxoviridae family (e.g. Measles virus), Togaviridae family (e.g. Rubella virus).

In another embodiment of any of the foregoing methods, the method further includes administering to the subject an additional anticancer therapy (e.g., chemotherapeutic or cytotoxic agent or radiotherapy).

In particular embodiments, the additional anticancer therapy is: a chemotherapeutic or cytotoxic agent (e.g., doxorubicin or ifosfamide), a differentiation-inducing agent (e.g., retinoic acid, vitamin D, cytokines), a hormonal agent, an immunological agent, or an anti-angiogenic agent. Chemotherapeutic and cytotoxic agents include, but are not limited to, alkylating agents, cytotoxic antibiotics, antimetabolites, vinca alkaloids, etoposides, and others (e.g., paclitaxel, taxol, docetaxel, taxotere, cis-platinum). A list of additional compounds having anticancer activity can be found in L. Brunton, B. Chabner and B. Knollman (eds). Goodman and Gilman's The Pharmacological Basis of Therapeutics, Twelfth Edition, 2011, McGraw Hill Companies, New York, N.Y.

In particular embodiments, the compound of the invention and the additional anticancer therapy and any of the foregoing compounds or pharmaceutical compositions are administered within 28 days of each other (e.g., within 21, 14, 10, 7, 5, 4, 3, 2, or 1 days) or within 24 hours (e.g., 12, 6, 3, 2, or 1 hours; or concomitantly) each in an amount that together are effective to treat the subject.

Chemical Terms

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the compounds described herein can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged cyclyl," as used herein, refers to a bridged polycyclic group of 5 to 20 atoms, containing from 1 to 3 bridges. Bridged cyclyl includes bridged carbocyclyl (e.g., norbornyl) and bridged heterocyclyl (e.g., 1,4-diazabicyclo[2.2.2]octane).

The term "cyano," as used herein, represents a —CN group.

The term "carbocyclyl," as used herein, refers to a non-aromatic $C_3$-$C_{12}$ monocyclic or polycyclic (e.g., bicyclic or tricyclic) structure in which the rings are formed by carbon atoms. Carbocyclyl structures include cycloalkyl groups and unsaturated carbocyclyl radicals. Polycyclic carbocyclyl includes spirocyclic carbocyclyl, bridged carbocyclyl, and fused carbocyclyl.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic monocyclic or polycyclic structure of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a monocyclic or polycyclic (e.g., bicyclic or tricyclic) structure having 3 to 12 atoms having at least one ring containing 1, 2, 3, or 4 ring atoms selected from N, O or S, wherein no ring is aromatic. Polycyclic heterocyclyl includes spirocyclic heterocyclyl, bridged heterocyclyl, and fused heterocyclyl. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $—NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxyl), aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds described herein can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on 25 opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure.

Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term “a” may be understood to mean “at least one”; (ii) the term “or” may be understood to mean “and/or”; and (iii) the terms “including” and “including” may be understood to encompass itemized components or steps whether presented by themselves or together with one or more additional components or steps.

As used herein, the terms “about” and “approximately” refer to a value that is within 10% above or below the value being described. For example, the term “about 5 nM” indicates a range of from 4.5 to 5.5 nM.

As used herein, the term “administration” refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term “adult soft tissue sarcoma” refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi’s sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

As used herein, the term “BAF complex” refers to the BRG1- or HRBM-associated factors complex in a human cell.

As used herein, the term “BAF complex-related disorder” refers to a disorder that is caused or affected by the level and/or activity of a BAF complex.

As used herein, the terms “GBAF complex” and “GBAF” refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term “cancer” refers to a condition caused by the proliferation of malignant neoplastic cells, such as tumors, neoplasms, carcinomas, sarcomas, leukemias, and lymphomas.

As used herein, the term “BRD9” refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence of which is set forth in SEQ ID NO: 1. The term “BRD9” also refers to natural variants of the wild-type BRD9 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9, which is set forth in SEQ ID NO: 2.

As used herein, the term “BRD9-related disorder” refers to a disorder that is caused or affected by the level and/or activity of BRD9. The term “cancer” refers to a condition caused by the proliferation of malignant neoplastic cells, such as tumors, neoplasms, carcinomas, sarcomas, leukemias, and lymphomas.

As used herein, a “combination therapy” or “administered in combination” means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the term "degrader" refers to a small molecule compound including a degradation moiety, wherein the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

As used herein, the terms "effective amount," "therapeutically effective amount," and "a "sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein or mRNA in a sample.

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the term "SS18-SSX fusion protein-related disorder" refers to a disorder that is caused or affected by the level and/or activity of SS18-SSX fusion protein.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
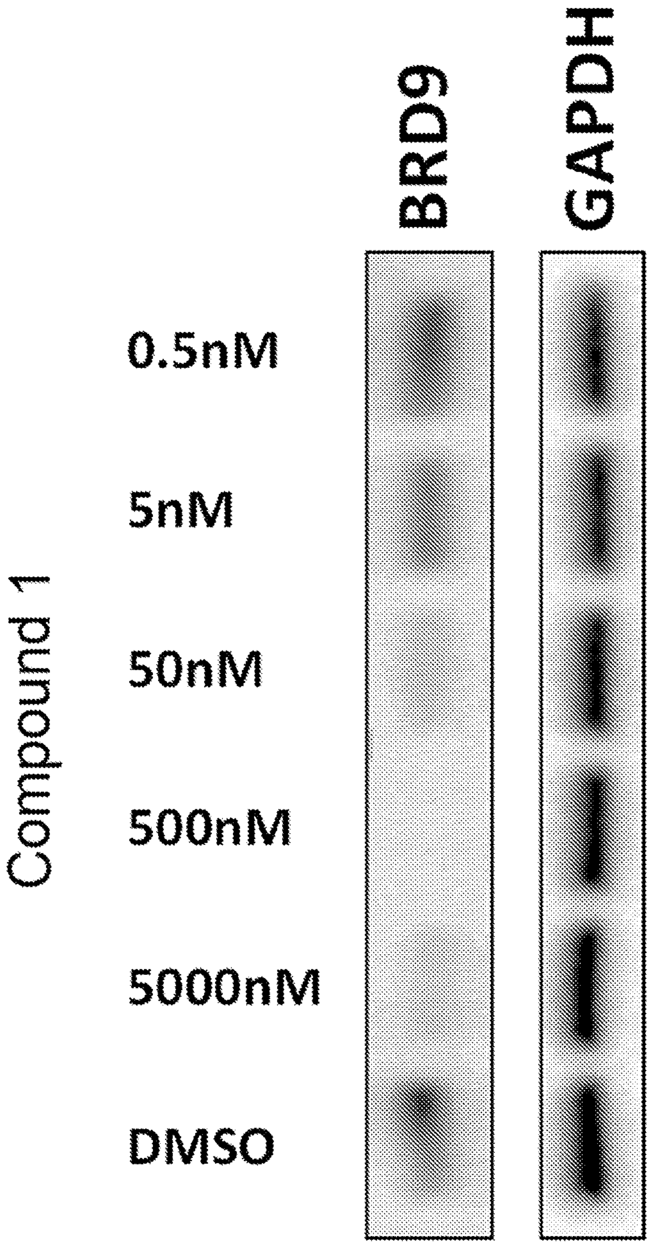
FIG. 1 is an image illustrating dose dependent depletion of BRD9 levels in a synovial sarcoma cell line (SYO1) in the presence of a BRD9 degrader.

The present disclosure features compositions and methods useful for the treatment of BAF-related disorders (e.g., cancer and infection). The disclosure further features compositions and methods useful for inhibition of the level and/or activity of BRD9, e.g., for the treatment of disorders such as cancer (e.g., sarcoma) and infection (e.g., viral infection), e.g., in a subject in need thereof.

Compounds

Compounds described herein reduce the level of an activity related to BRD9, or a related downstream effect, or reduce the level of BRD9 in a cell or subject. Exemplary compounds described herein have the structure according to Formula I:

A-L-B Formula I, wherein

B is a degradation moiety,

L is a linker, and

A has the structure of Formula II:

Formula II

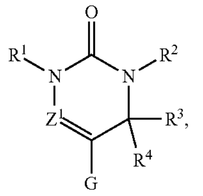

wherein $R^1$ is, independently, H, optionally substituted $C_1$-$C_6$ alkyl, optionally substituted $C_1$-$C_6$ heteroalkyl, or optionally substituted $C_3$-$C_{10}$ carbocyclyl;

$Z^1$ is $CR^5$ or N;

$R^2$ is, independently, H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted sulfone, or optionally substituted sulfonamide, or $R^2$ and $R^3$ together with the atoms to which each is attached, form an optionally substituted $C_2$-$C_9$ heterocyclyl;

$R^3$ and $R^4$ are, independently, H, halogen, hydroxyl, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, thiol, optionally substituted sulfone, or optionally substituted amino, and/or $R^2$ and $R^3$ together with the atoms to which each is attached, form an optionally substituted $C_2$-$C_9$ heterocyclyl;

$R^5$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and G is

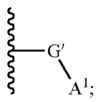

G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and $A^1$ is a bond between A and the linker, or a pharmaceutically acceptable salt thereof.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., *Agnew, Chem. Intl. Ed Engl.* 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Oncol.* 18:233a (1999), and Douillard et al., *Lancet* 355(9209):1041-1047 (2000).

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-1-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Example 1. BRD9 Degrader Depletes BRD9 Protein

The following example demonstrates the depletion of the BRD9 protein in synovial sarcoma cells treated with a BRD9 degrader.

Procedure: Cells were treated with DMSO or the BRD9 degrader, Compound 1 (also known as dBRD9, see Remillard et al, *Angew. Chem. Int. Ed. Engl.* 56(21):5738-5743 (2017); see structure of compound 1 below), for indicated doses and timepoints.

(Compound 1)

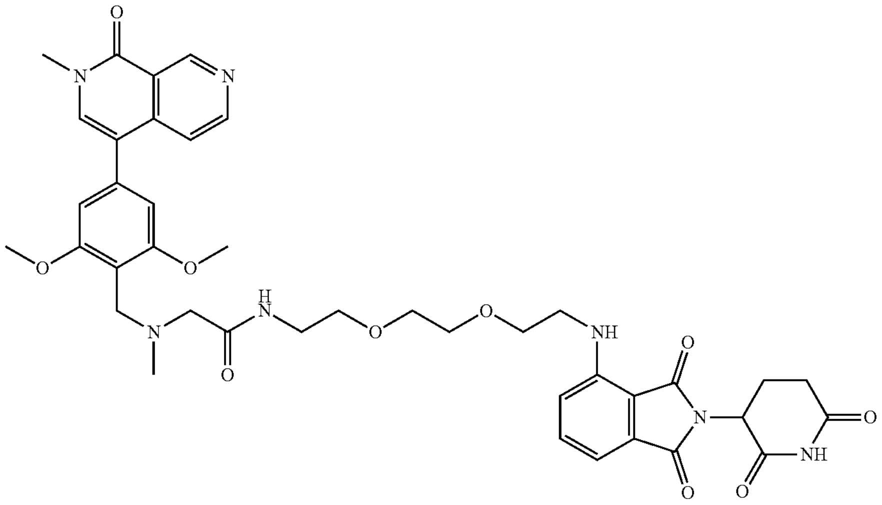

dBRD9

Figure 2:
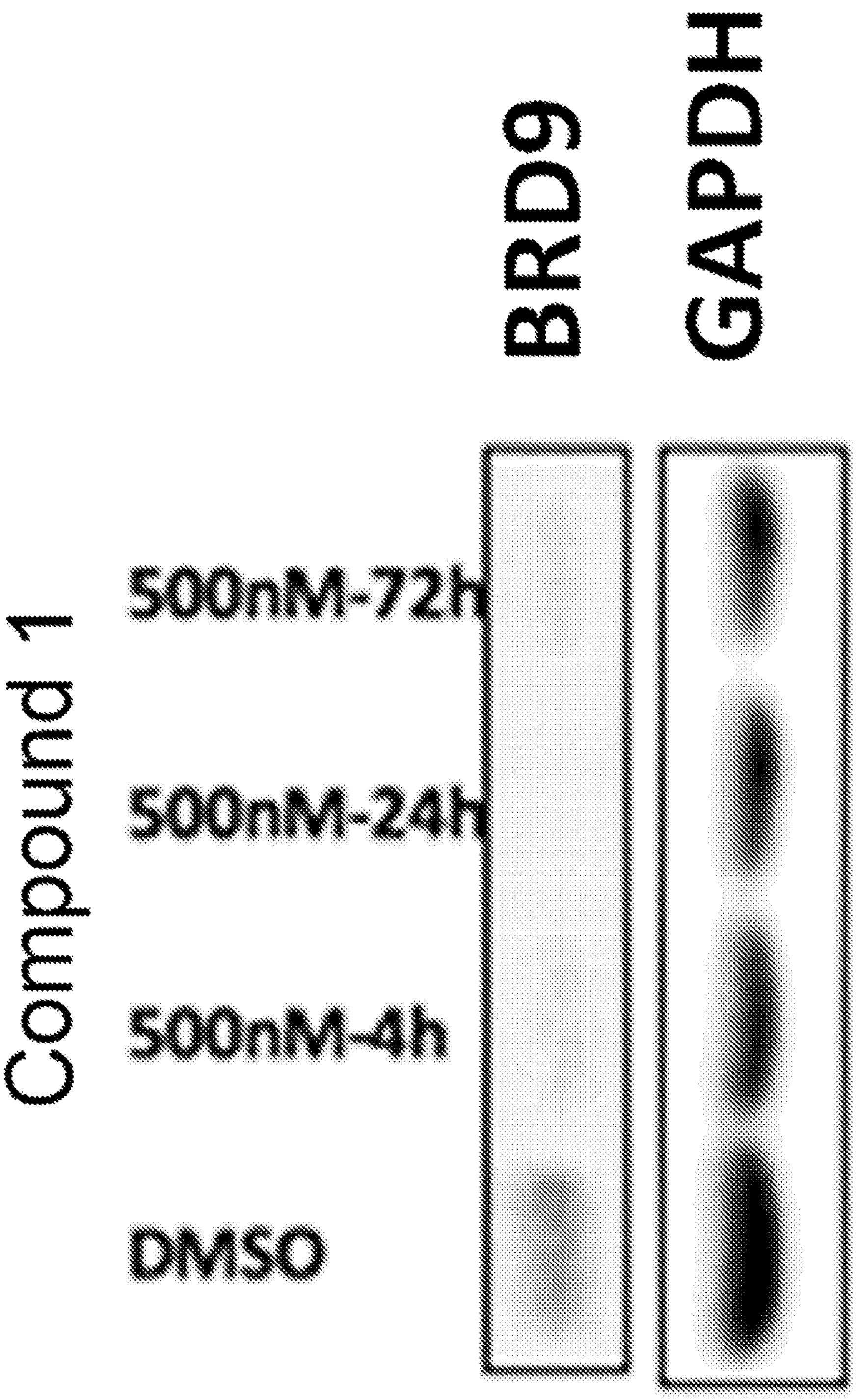
FIG. 2 is an image illustrating sustained suppression of BRD9 levels in a synovial sarcoma cell line (SYO1) in the presence of a BRD9 degrader over 72 hours.
Figure 3:
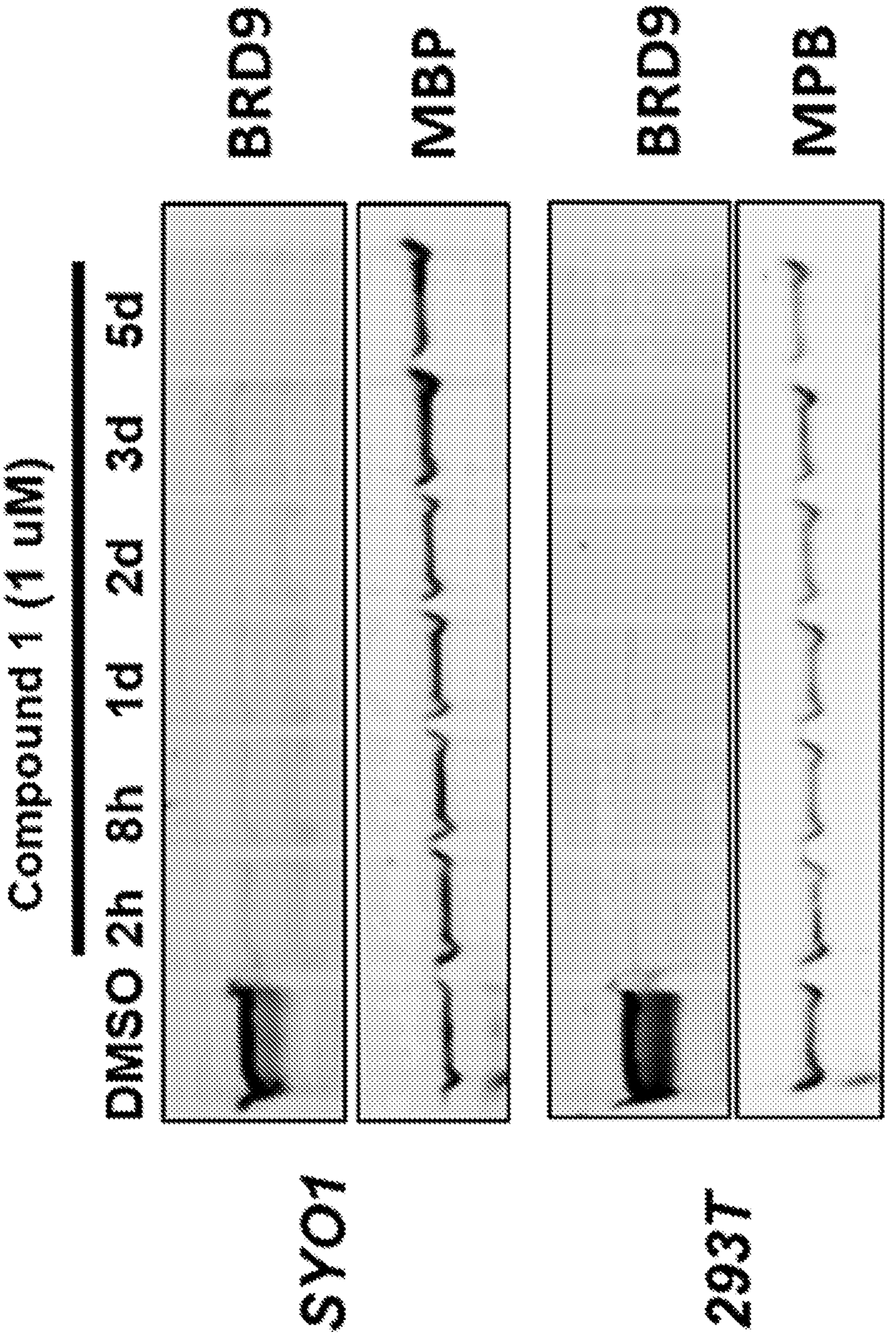
FIG. 3 is an image illustrating sustained suppression of BRD9 levels in two cell lines (293T and SYO1) in the presence of a BRD9 degrader over 5 days.

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 min, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C. Membranes were washed three times for 10 min and incubated with anti-mouse or anti-rabbit antibodies conjugated with either horseradish peroxidase (HRP, FIGS. 1-2) or IRDye (FIG. 3, 1:20,000, LI-COR) for at least 1 h. Blots were washed with TBST three times and developed with either the ECL system according to the manufacturer's protocols (FIGS. 1-2) or scanned on an Odyssey CLx Imaging system (FIG. 3).

Results: Treatment of SYO1 synovial sarcoma cells with the BRD9 degrader Compound 1 results in dose dependent (FIG. 1) and time dependent (FIG. 2) depletion of BRD9 in the cells. Further, as shown in FIG. 3, the depletion of BRD9 by Compound 1 is replicated in a non-synovial sarcoma cell line (293T) and may be sustained for at least 5 days.

Example 2. Inhibition of Growth of Synovial Cell Lines by BRD9 Inhibitors and BRD9 Degraders The following example demonstrates that BRD9 degraders and inhibitors selectively inhibit growth of synovial sarcoma cells.

Figure 5:
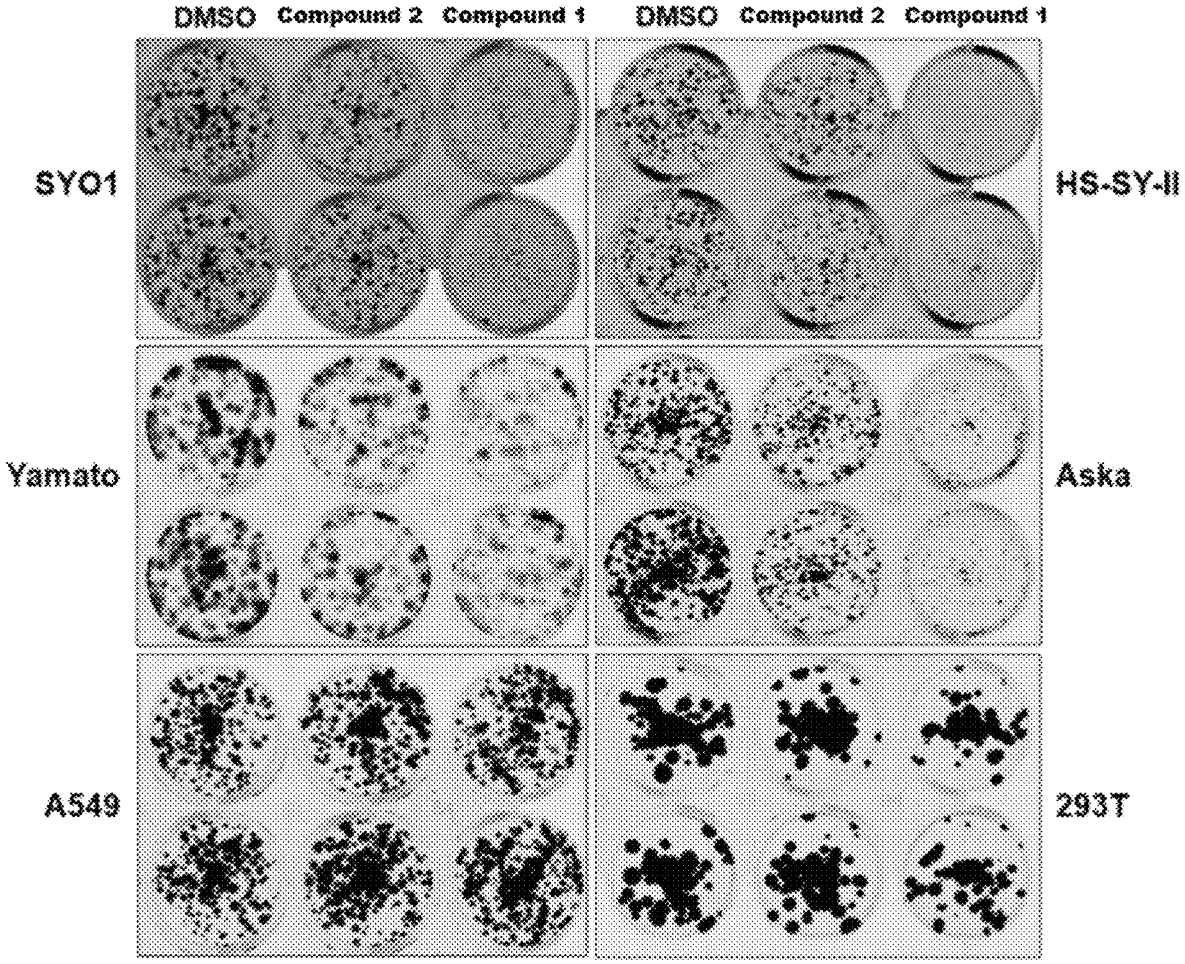
FIG. 5 is an image illustrating the effect on cell growth of six cell lines (SYO1, Yamato, A549, HS-SY-II, ASKA, and 293T) in the presence of a BRD9 degrader and a BRD9 inhibitor.

Procedures:

Cells were treated with DMSO or the BRD9 degrader, Compound 1, at indicated concentrations, and proliferation was monitored from day 7 to day 14 by measuring confluency overtime using an IncuCyte live cell analysis system (FIG. 5). Growth medium and compounds were refreshed every 3-4 days.

Cells were seeded into 12-well plates and treated with DMSO, 1 μM BRD9 inhibitor, Compound 2 (also known as BI-7273, see Martin et al, *J Med Chem.* 59(10):4462-4475 (2016); see structure of compound 2 below), or 1 μM BRD9 degrader, Compound 1.

(Compound 2)

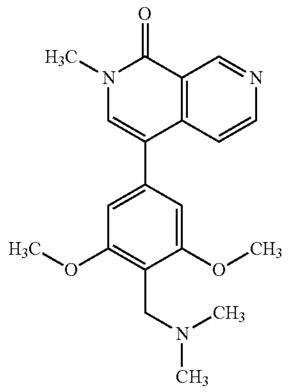

BI-7273

Figure 6:
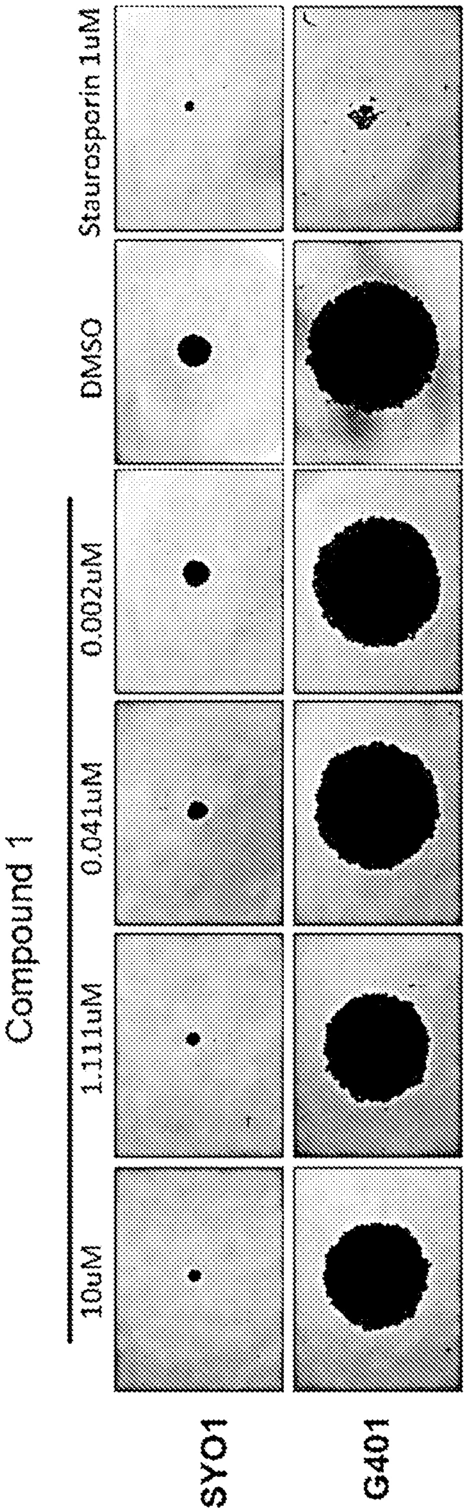
FIG. 6 is an image illustrating the effect on cell growth of two cell lines (SYO1 and G401) in the presence of a BRD9 degrader.

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1 L) for 30 min followed by 3× washes with water and drying the plates for at least 24 h at room temperature. Subsequently plates were scanned on an Odyssey CLx Imaging system (FIG. 6).

Cells were seeded into 96-well ultra-low cluster plate (Costar, #7007) in 200 μL complete media and treated at day 2 with DMSO, Staurosporin, or BRD9 degrader, Compound 1, at indicated doses (FIG. 3C). Media and compounds were changed every 5 d and cell colonies were imaged at day 14.

Figure 4:
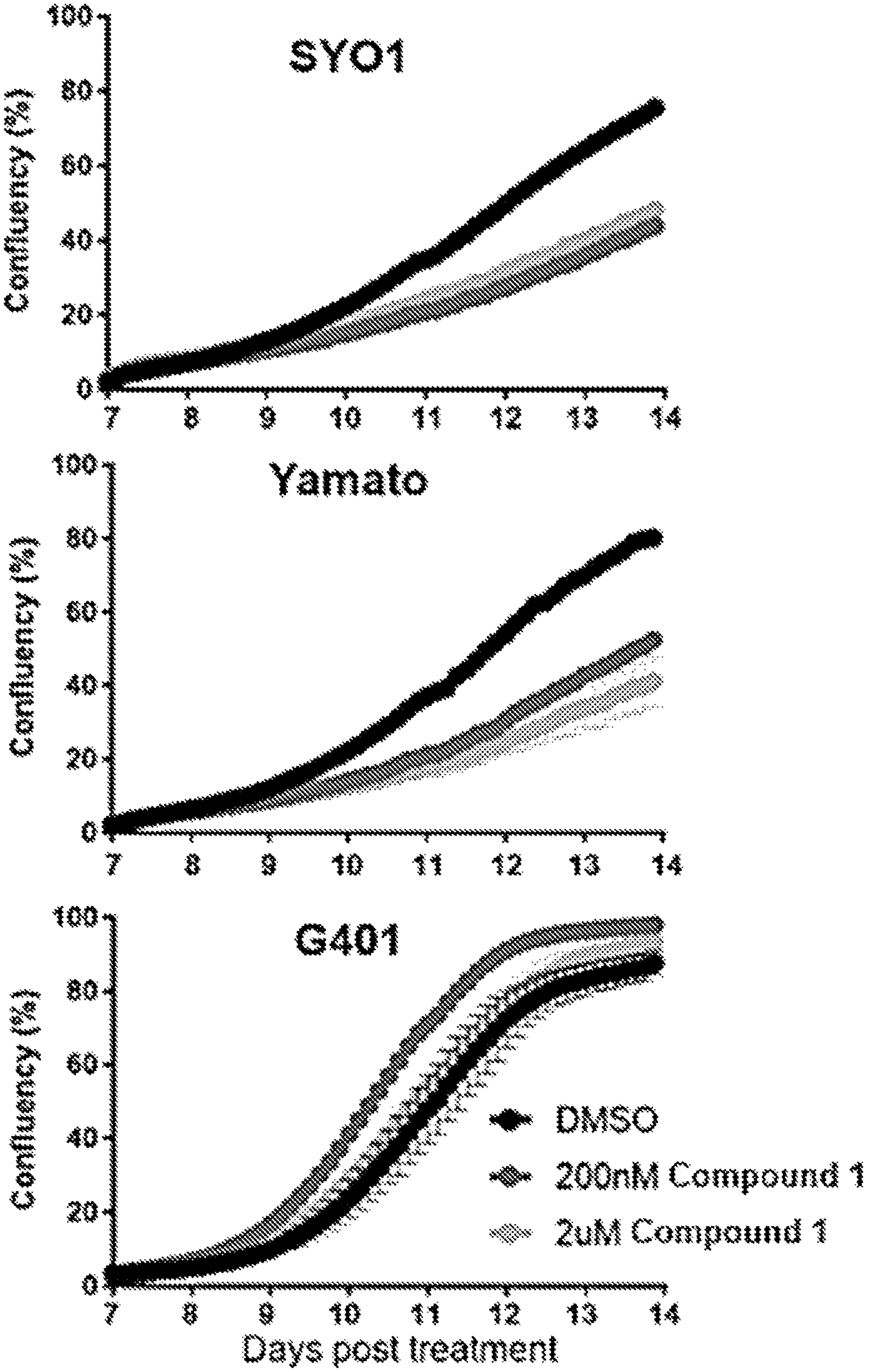
FIG. 4 is an image illustrating sustained suppression of BRD9 levels in three synovial sarcoma cell lines (293T, SYO1, and Yamato) in the presence of a BRD9 degrader over 7 days compared to the levels in cells treated with CRISPR reagents.

Results: As shown in FIGS. 4, 5, and 6, treatment of synovial sarcoma cell lines (SYO1, Yamato, HS-SY-II, and ASKA) with a BRD9 inhibitor, Compound 2, or a BRD9 degrader, Compound 1, results in inhibition of the growth of the cells, but does not result in inhibition of the growth of non-synovial control cancer cell lines (293T, A549, G401).

Example 3. Selective Inhibition of Growth of Synovial Cell Lines by BRD9 Degraders and BRD9 Binders The following example demonstrates that BRD9 degraders and binders selectively inhibit growth of synovial sarcoma cells.

Procedure: Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 μL of 0.005% (w/v) crystal violet solution in 25% (v/v) methanol for at least 1 hour at room temperature. Subsequently plates were scanned on an Odyssey CLx Imaging system.

Figure 7:
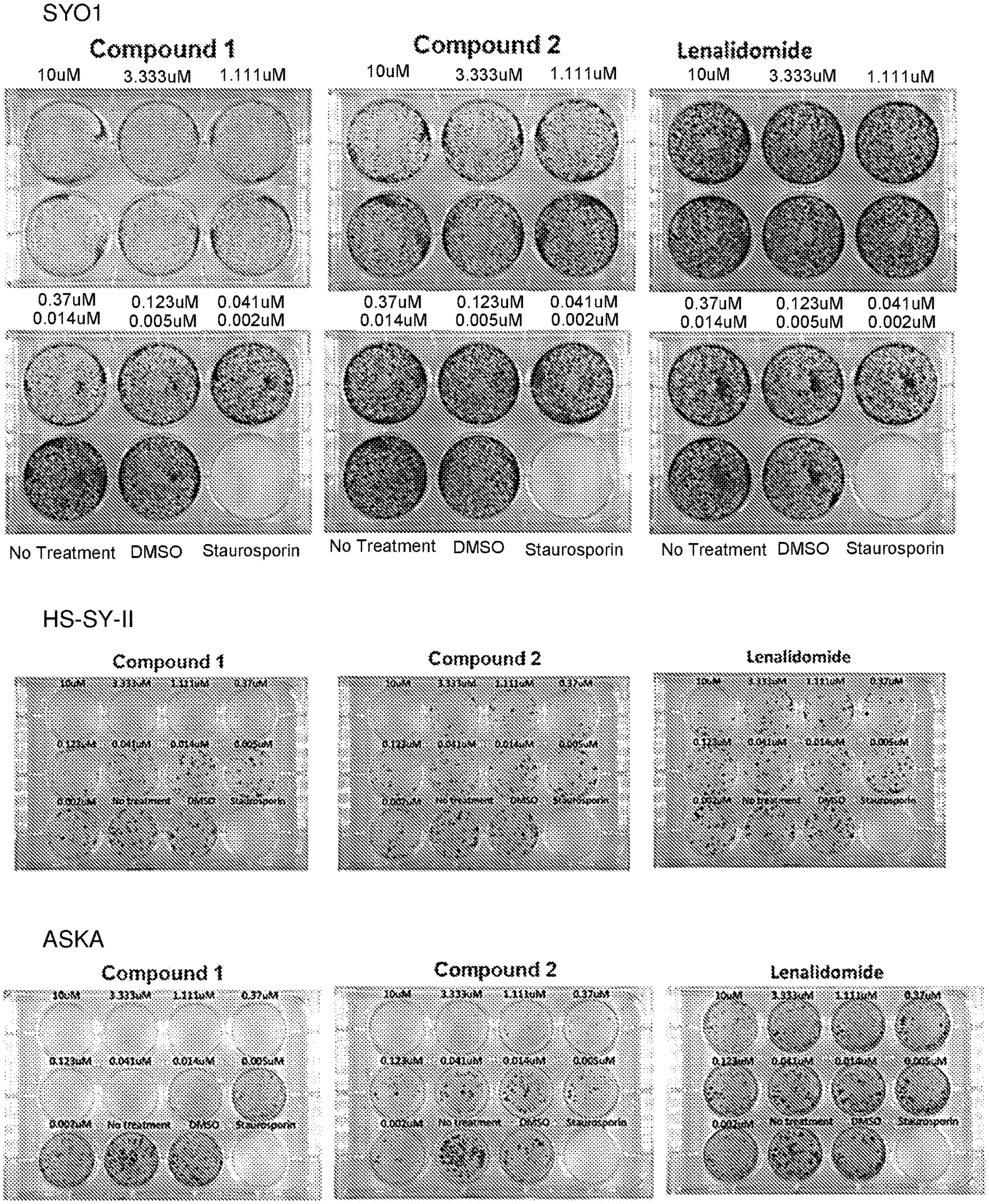
FIG. 7 is an image illustrating the effect on cell growth of three synovial sarcoma cell lines (SYO1, HS-SY-II, and ASKA) in the presence of a BRD9 degrader, BRD9 binder and E3 ligase binder.
Figure 8:
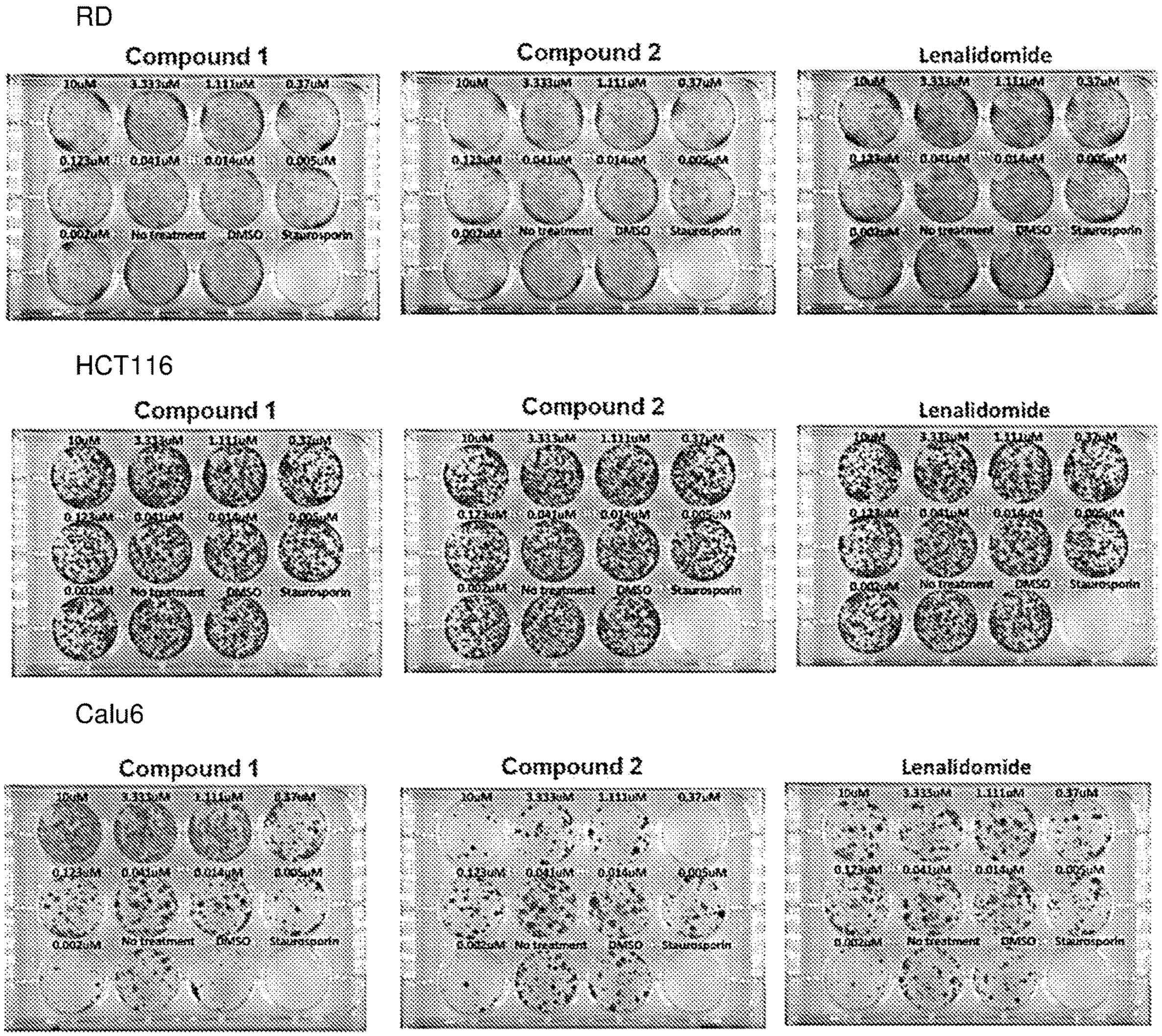
FIG. 8 is an image illustrating the effect on cell growth of three non-synovial sarcoma cell lines (RD, HCT116, and Calu6) in the presence of a BRD9 degrader, BRD9 binder and E3 ligase binder.
Figure 9:
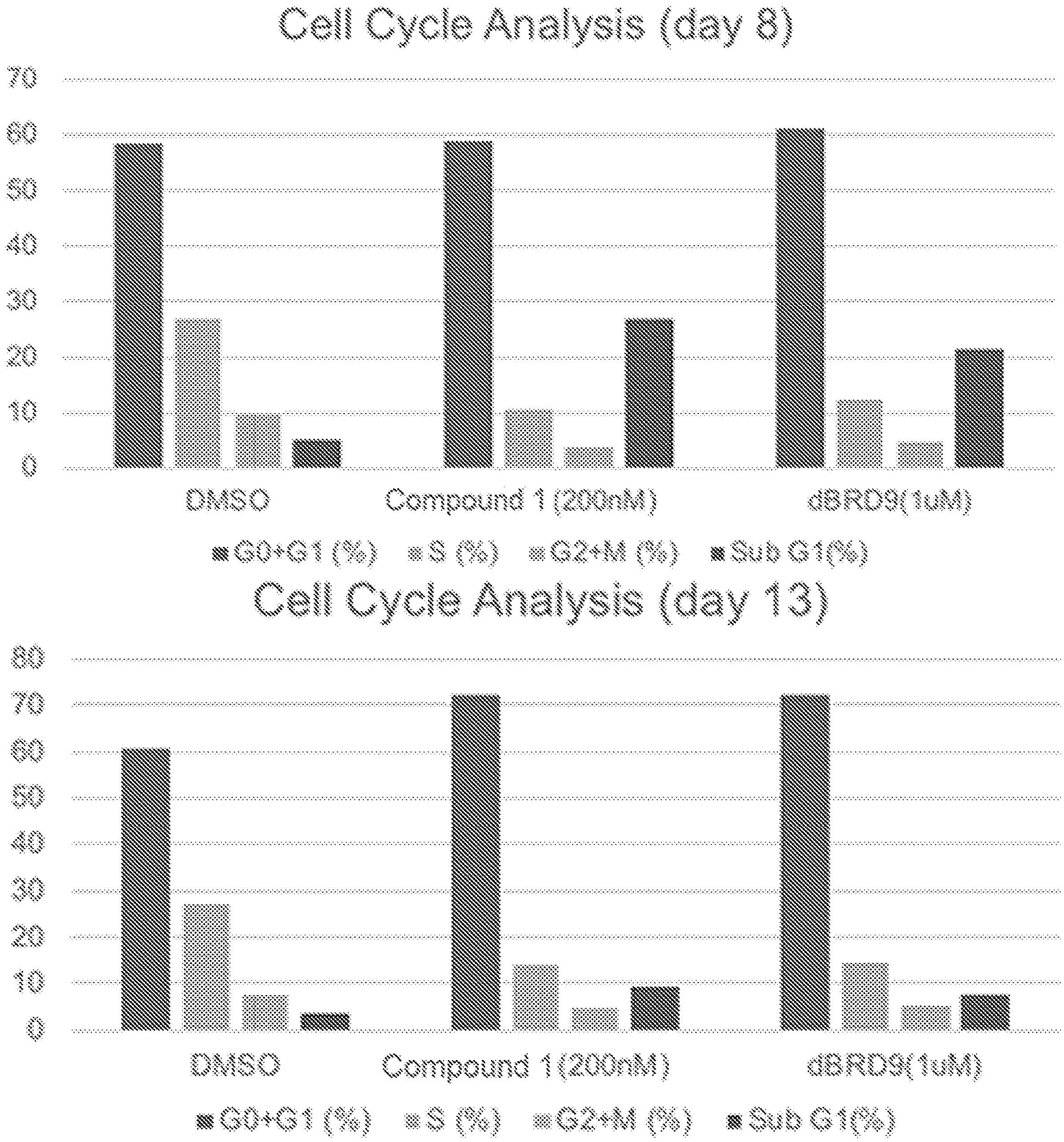
FIG. 9 is a graph illustrating the percentage of SYO1 in various cell cycle phases following treatment with DMSO, Compound 1 at 200 nM, or Compound 1 at 1 μM for 8 or 13 days.
Figure 10:
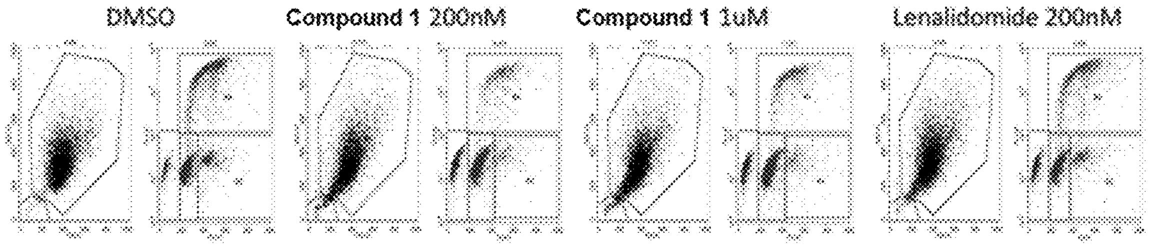
FIG. 10 is a series of contour plots illustrating the percentage of SYO1 cells in various cell cycle phases following treatment with DMSO, Compound 1 at 200 nM, Compound 1 at 1 μM, or lenalidomide at 200 nM for 8 days. Numerical values corresponding to each contour plot are found in the table below.
Figure 11:
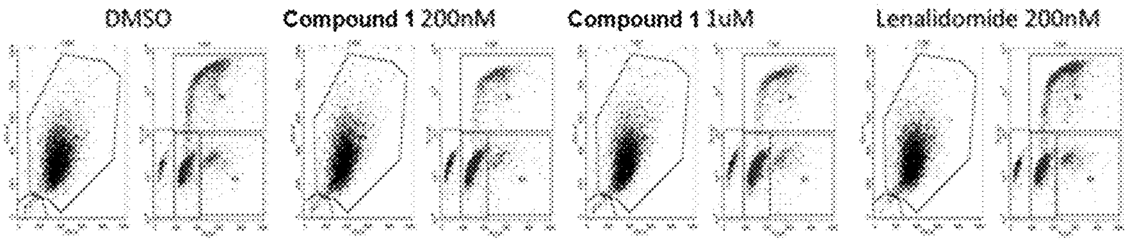
FIG. 11 is a series of contour plots illustrating the percentage of SYO1 cells in various cell cycle phases following treatment with DMSO, Compound 1 at 200 nM, Compound 1 at 1 μM, or lenalidomide at 200 nM for 13 days. Numerical values corresponding to each contour plot are found in the table below.
Figure 12:
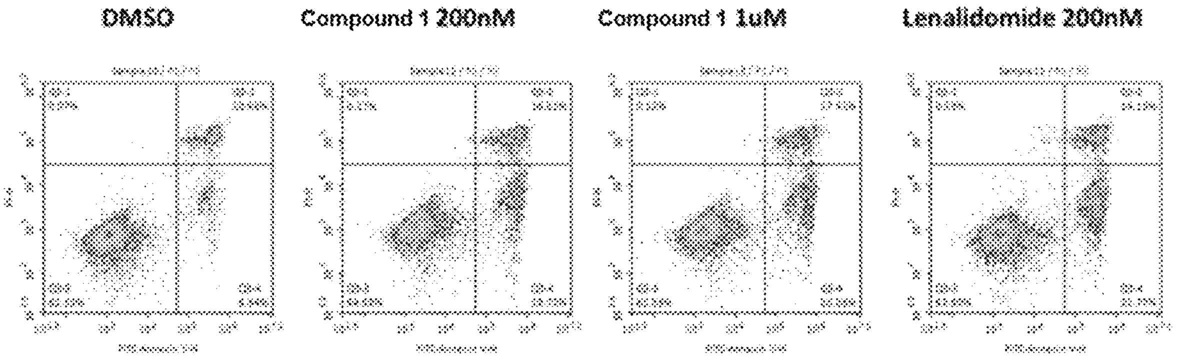
FIG. 12 is a series of contour plots illustrating the percentage of early- and late-apoptotic SYO1 cells following treatment with DMSO, Compound 1 at 200 nM, Compound 1 at 1 μM, or lenalidomide at 200 nM for 8 days. Numerical values corresponding to each contour plot are found in the table below.

Results: As shown in FIGS. 7 and 8, treatment of synovial sarcoma cell lines (SYO1, HS-SY-II, and ASKA) with Compound 1 or Compound 2 resulted in inhibition of the growth of the cells but did not result in inhibition of the growth of non-synovial control cancer cell lines (RD, HCT116, and Calu6). Overall, Compound 1 showed most significant growth inhibition in all synovial cell lines.

Example 4. Inhibition of Cell Growth in Synovial Sarcoma Cells

The following example shows that BRD9 degraders inhibit cell growth and induce apoptosis in synovial sarcoma cells.

Procedure: SYO1 cells were treated for 8 or 13 days with DMSO, a BRD9 degrader (Compound 1) at 200 nM or 1 μM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma A9210). Assays were performed according to the manufacturer's protocol.

Results: As shown in FIGS. 9-12, treatment with Compound 1 for 8 or 13 days resulted in reduced numbers of cells in the S-phase of the cell cycle as compared to DMSO and lenalidomide. Treatment with Compound 1 for 8 days also resulted in increased numbers of early- and late-apoptotic cells as compared to DMSO controls.

Example 5. Composition for SS18-SSX1-BAF

The following example shows the identification of BRD9 as a component of SS18-SSX containing BAF complexes.

Procedure: A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 13:
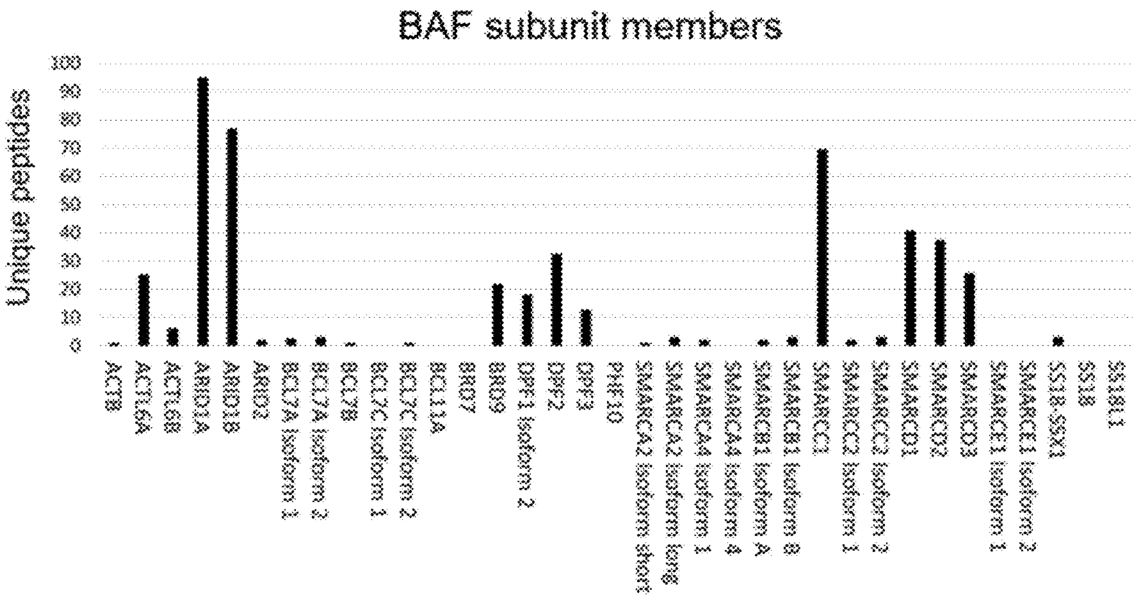
FIG. 13 is a graph illustrating the proteins present in BAF complexes including the SS18-SSX fusion protein.

Results: As shown in FIG. 13, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 6. Preparation of 3-(6-[4-[2-(1-[[4-(1,3-dimethyl-2-oxo-4H-pyrimidin-5-yl)-2,6-dimethoxy-phenyl]methyl]piperidin-4-yl)ethyl]piperazin-1-yl]-1-oxo-3H-isoindol-2-yl)piperidine-2,6-dione (Compound D1)

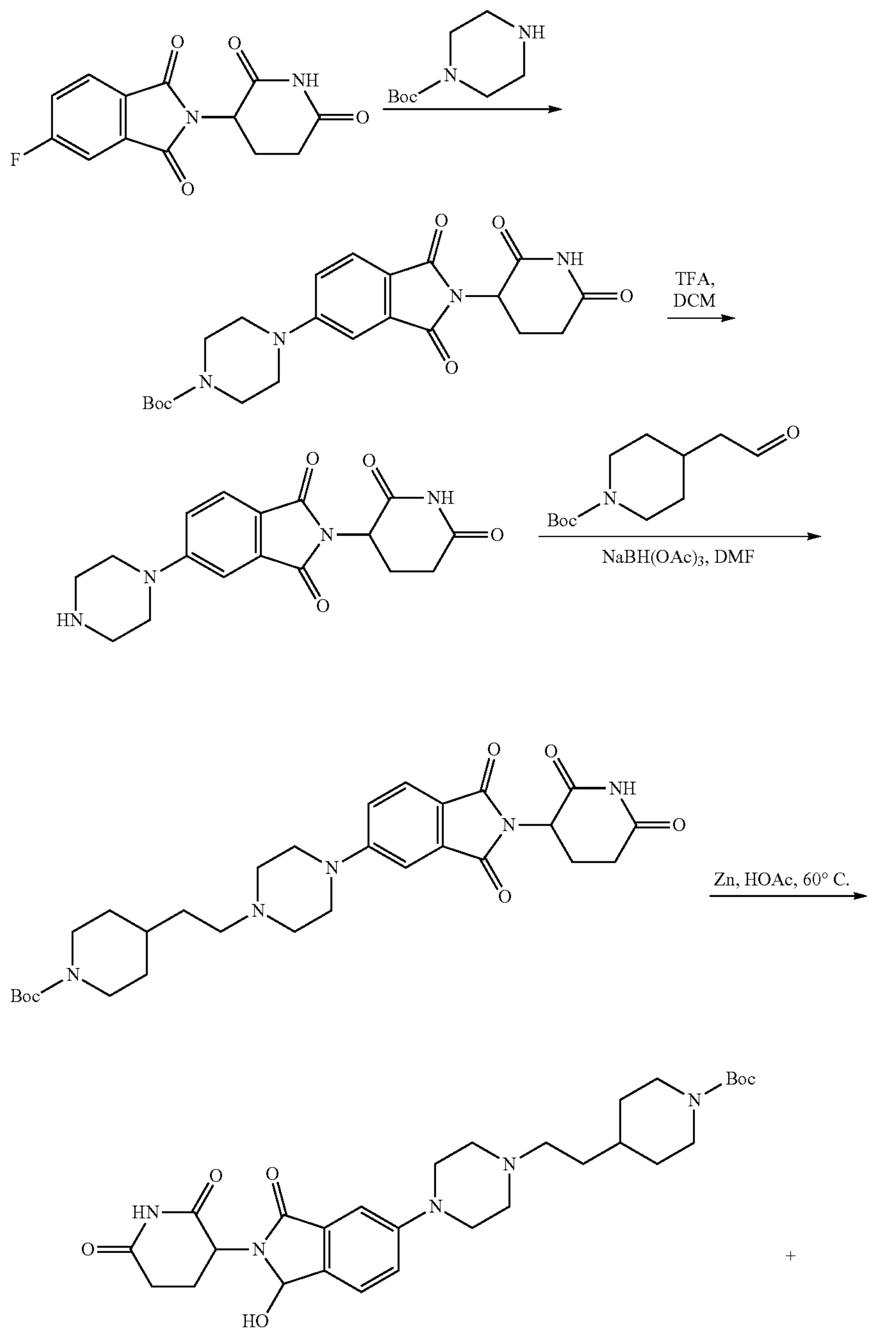

-continued

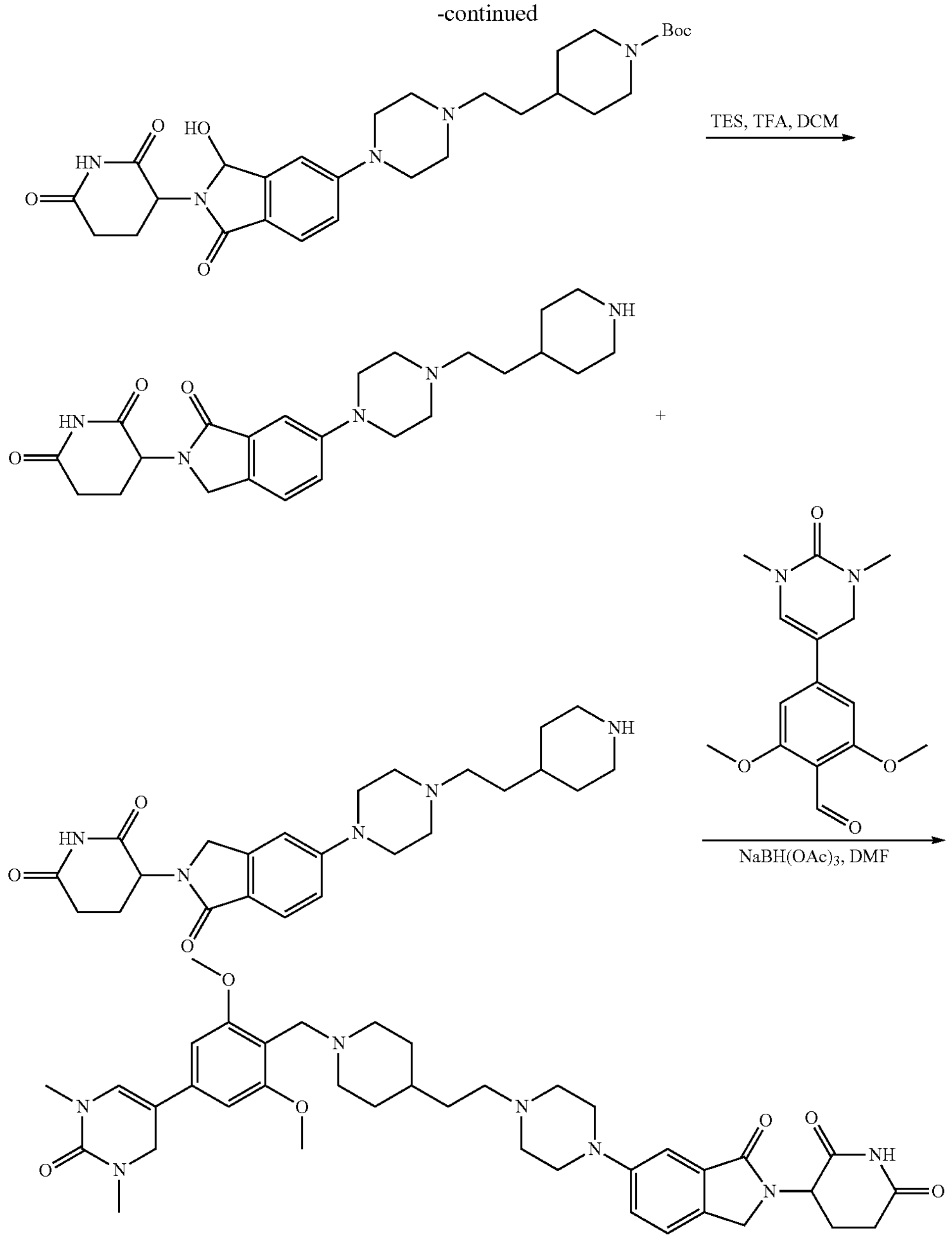

Step 1: Preparation of Tert-butyl 4-[2-(2,6-dioxopiperidin-3-yl)-1,3-dioxoisoindol-5-yl]piperazine-1-carboxylate

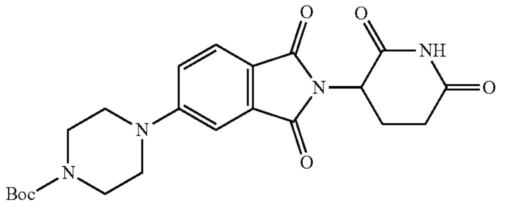 [SMILES: CC(C)(C)OC(=O)N1CCN(c2ccc3c(c2)C(=O)N(C2CCC(=O)NC2=O)C3=O)CC1]

To a stirred solution of 2-(2,6-dioxopiperidin-3-yl)-5-fluoroisoindole-1,3-dione (3.00 g, 10.861 mmol, 1.00 equivalent) and tert-butyl piperazine-1-carboxylate (2.02 g, 10.861 mmol, 1.00 equivalent) in NMP (30.00 mL) was added DIPEA (4.21 g, 32.574 mmol, 3.00 equivalent). The resulting mixture was stirred for 2 hours at 90° C. under nitrogen atmosphere. The resulting mixture was diluted with water (100 ml). The aqueous layer was extracted with EtOAc (3x30 mL). The organic layers were combined and concentrated under reduced pressure. The residue was purified by reverse flash chromatography with the following conditions: column, C18 silica gel; mobile phase, MeCN in water, 5% to 90% gradient in 30 minutes; detector, UV 254 nm. This resulted in tert-butyl 4-[2-(2,6-dioxopiperidin-3-yl)-1,3-dioxoisoindol-5-yl]piperazine-1-carboxylate (1.6 g, 33.29%) as a yellow solid. LCMS (ESI) m/z: [M+Na]+=465.

Step 2: Preparation of 2-(2,6-dioxopiperidin-3-yl)-5-(piperazin-1-yl)isoindole-1,3-dione

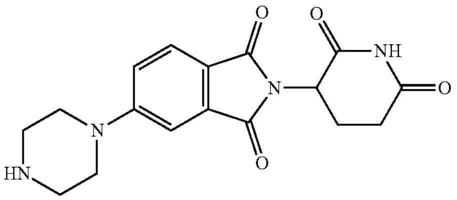 [SMILES: O=C1CCC(N2C(=O)c3ccc(N4CCNCC4)cc3C2=O)C(=O)N1]

To a stirred solution of tert-butyl 4-[2-(2,6-dioxopiperidin-3-yl)-1,3-dioxoisoindol-5-yl]piperazine-1-carboxylate (2.10 g, 4.746 mmol, 1.00 equivalent) in DCM (32.00 mL) was added TFA (8.00 mL). The resulting mixture was stirred for 2 hours at room temperature. The resulting mixture was concentrated under vacuum to afford 2-(2,6-dioxopiperidin-3-yl)-5-(piperazin-1-yl)isoindole-1,3-dione (2.6 g, 160.02%) as a yellow solid, which was used directly without further purification. LCMS (ESI) m/z: [M+H]+=343.

Step 3: Preparation of Tert-butyl 4-(2-[4-[2-(2,6-dioxopiperidin-3-yl)-1,3-dioxoisoindol-5-yl]piperazin-1-yl]ethyl)piperidine-1-carboxylate

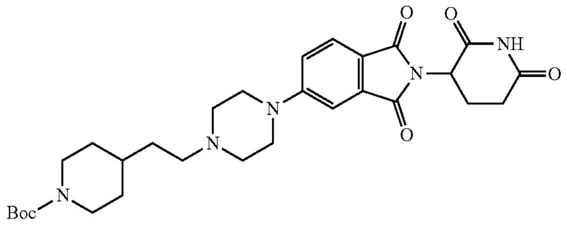 [SMILES: CC(C)(C)OC(=O)N1CCC(CCN2CCN(c3ccc4c(c3)C(=O)N(C3CCC(=O)NC3=O)C4=O)CC2)CC1]

To a stirred solution of 2-(2,6-dioxopiperidin-3-yl)-5-(piperazin-1-yl)isoindole-1,3-dione (2.00 g, 5.842 mmol, 1.00 equivalent) in DMF (25.00 mL) was added tert-butyl 4-(2-oxoethyl)piperidine-1-carboxylate (1.33 g, 5.842 mmol, 1.00 equivalent) under nitrogen atmosphere. The resulting mixture was stirred for 16 h at room temperature under nitrogen atmosphere. To the above mixture was added $NaBH(OAc)_3$ (2.48 g, 11.684 mmol, 2.00 equivalent). The resulting mixture was stirred for additional 2 hours at room temperature. The resulting mixture was diluted with water (70 mL). The aqueous layer was extracted with EtOAc (4×30 mL). The organic layers were concentrated under vacuum. The residue was purified by silica gel column chromatography, eluted with DCM:MeOH (50:1 to 10:1) to afford tert-butyl 4-(2-[4-[2-(2,6-dioxopiperidin-3-yl)-1,3-dioxoisoindol-5-yl]piperazin-1-yl]ethyl)piperidine-1-carboxylate (3 g, 92.75%) as a yellow oil. LCMS (ESI) m/z: [M+H]+=554.

Step 4: Preparation of Tert-butyl 4-(2-[4-[2-(2,6-dioxopiperidin-3-yl)-1-hydroxy-3-oxo-1H-isoindol-5-yl]piperazin-1-yl]ethyl)piperidine-1-carboxylate and tert-butyl 4-(2-[4-[2-(2,6-dioxopiperidin-3-yl)-3-hydroxy-1-oxo-3H-isoindol-5-yl]piperazin-1-yl]ethyl)piperidine-1-carboxylate

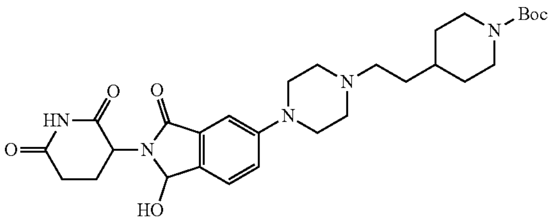

+

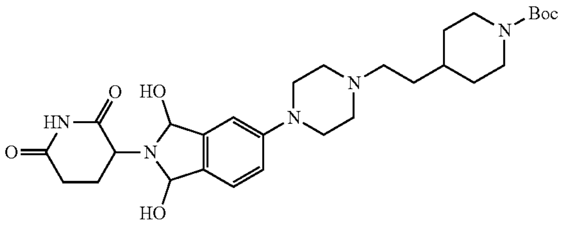

To a solution of tert-butyl 4-(2-[4-[2-(2,6-dioxopiperidin-3-yl)-1,3-dioxoisoindol-5-yl]piperazin-1-yl]ethyl)piperidine-1-carboxylate (500.00 mg, 0.903 mmol, 1.00 equivalent) in HOAc (8.00 mL, 0.133 mmol, 0.15 equivalent) was added Zn (590.70 mg, 9.031 mmol, 10 equivalent). The mixture solution was stirred for 3 hours at 60° C. The mixture was allowed to cool down to room temperature. The precipitated solids were collected by filtration and washed with EtOAc (3×5 mL). The mixture was concentrated under reduced pressure. The residue was purified by reverse flash chromatography with the following conditions: (column, C18 silica gel; mobile phase, FA in water, 0% to 30% gradient in 30 minutes; detector, UV 254 nm) to afford tert-butyl 4-(2-[4-[2-(2,6-dioxopiperidin-3-yl)-1-hydroxy-3-oxo-1H-isoindol-5-yl]piperazin-1-yl]ethyl)piperidine-1-carboxylate and tert-butyl 4-(2-[4-[2-(2,6-dioxopiperidin-3-yl)-3-hydroxy-1-oxo-3H-isoindol-5-yl]piperazin-1-yl]ethyl)piperidine-1-carboxylate as a brown solid. LCMS (ESI) m/z: [M+H]+=556.

Step 5: Preparation of 3-(1-oxo-6-[4-[2-(piperidin-4-yl)ethyl]piperazin-1-yl]-3H-isoindol-2-yl)piperidine-2,6-dione and 3-(1-oxo-5-[4-[2-(piperidin-4-yl)ethyl]piperazin-1-yl]-3H-isoindol-2-yl)piperidine-2,6-dione

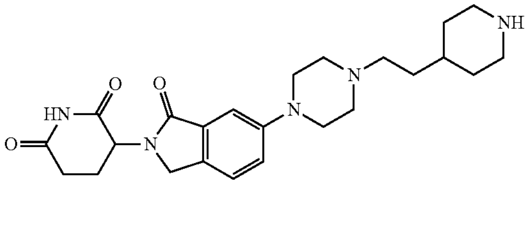

+

-continued

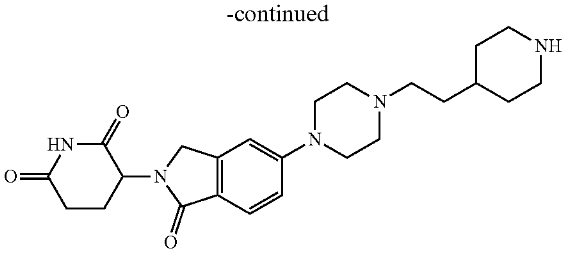

To a stirred solution of tert-butyl 4-(2-[4-[2-(2,6-dioxopiperidin-3-yl)-1-hydroxy-3-oxo-1H-isoindol-5-yl]piperazin-1-yl]ethyl)piperidine-1-carboxylate and tert-butyl 4-(2-[4-[2-(2,6-dioxopiperidin-3-yl)-3-hydroxy-1-oxo-3H-isoindol-5-yl]piperazin-1-yl]ethyl)piperidine-1-carboxylate (700.00 mg) in DCM (5.00 mL) was added TES (1.00 mL) and TFA (1.00 mL) at room temperature. The resulting mixture was stirred for overnight at room temperature. The mixture was purified by Prep-HPLC with the following conditions (Column: XSelect CSH Prep C18 OBD Column, 5 μm, 19*150 mm; Mobile Phase A: Water (0.05% TFA), Mobile Phase B: ACN; Flow rate: 25 mL/min; Gradient: 1 B to 9 B in 15 minutes; 254/220 nm; $R_{T1}$: 10.23) to afford 3-(1-oxo-6-[4-[2-(piperidin-4-yl)ethyl]piperazin-1-yl]-3H-isoindol-2-yl)piperidine-2,6-dione (144 mg) as a brown oil and 3-(1-oxo-5-[4-[2-(piperidin-4-yl)ethyl]piperazin-1-yl]-3H-isoindol-2-yl)piperidine-2,6-dione (187 mg) as a brown oil. LCMS (ESI) m/z: [M+H]+=440.

Step 6: Preparation of 3-(6-[4-[2-(1-[[4-(1,3-dimethyl-2-oxo-4H-pyrimidin-5-yl)-2,6-dimethoxyphenyl]methyl]piperidin-4-yl)ethyl]piperazin-1-yl]-1-oxo-3H-isoindol-2-yl)piperidine-2,6-dione (Compound D1)

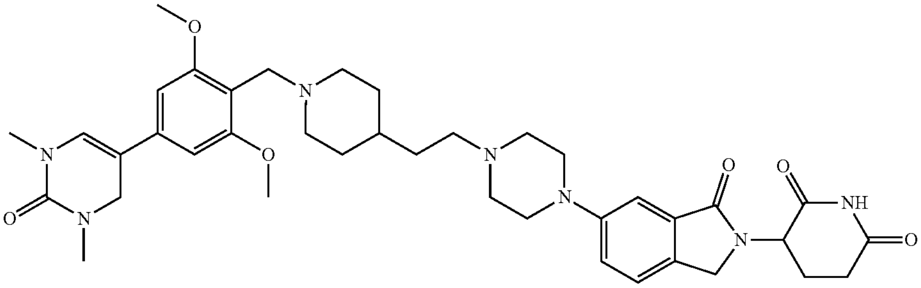 [SMILES: COc1cc(C2=CN(C)C(=O)N(C)C2)cc(OC)c1CN1CCC(CCN2CCN(c3ccc4c(c3)C(=O)N(C3CCC(=O)NC3=O)C4)CC2)CC1]

To a stirred solution of 3-(1-oxo-6-[4-[2-(piperidin-4-yl)ethyl]piperazin-1-yl]-3H-isoindol-2-yl)piperidine-2,6-dione (100.00 mg, 0.228 mmol, 1.00 equivalent) and 4-(1,3-dimethyl-2-oxo-4H-pyrimidin-5-yl)-2,6-dimethoxybenzaldehyde (66.05 mg, 0.228 mmol, 1 equivalent) in DMF (3 mL) was added $NaBH(OAc)_3$ (144.65 mg, 0.683 mmol, 3 equivalent) in portions at room temperature under air atmosphere. The resulting mixture was stirred for overnight at room temperature under air atmosphere. The crude product (150 mg) was purified by Prep-HPLC with the following conditions (Column: Xcelect CSH F-pheny OBD Column, 19*250 mm, 5 μm; Mobile Phase A: Water (0.05% TFA), Mobile Phase B: ACN; Flow rate: 25 mL/min; Gradient: 11 B to 24 B in 15 minutes; 254/220 nm; $R_{T1}$: 13.02) to afford 3-(6-[4-[2-(1-[[4-(1,3-dimethyl-2-oxo-4H-pyrimidin-5-yl)-2,6-dimethoxyphenyl]methyl]piperidin-4-yl)ethyl]piperazin-1-yl]-1-oxo-3H-isoindol-2-yl)piperidine-2,6-dione (44 mg, 21.67%) as a light yellow solid. $^1H$ NMR (400 MHz, DMSO-d6) δ 10.99 (s, 1H), 7.51 (dd, J=8.5, 4.8 Hz, 1H), 7.39-7.26 (m, 2H), 7.17 (s, 1H), 6.67 (s, 2H), 5.11 (dd, J=13.2, 5.0 Hz, 1H), 4.41-4.34 (m, 1H), 4.29 (s, 2H), 4.26 (d, J=3.1 Hz, 1H), 4.22 (s, 1H), 4.14 (d, J=4.4 Hz, 2H), 3.98 (s, 1H), 3.95 (s, 1H), 3.88 (d, J=3.7 Hz, 6H), 3.83 (s, 1H), 3.60 (d, J=12.2 Hz, 2H), 3.37 (d, J=12.2 Hz, 2H), 3.17 (s, 5H), 3.09 (s, 3H), 3.03 (d, J=12.0 Hz, 1H), 2.96 (d, J=4.0 Hz, 1H), 2.93 (s, 1H), 2.91 (s, 3H), 2.61 (d, J=17.5 Hz, 1H), 2.47-2.33 (m, 1H), 2.05-1.95 (m, 1H), 1.84 (d, J=13.5 Hz, 2H), 1.62 (d, J=10.2 Hz, 2H), 1.45 (t, J=12.3 Hz, 2H). LCMS (ESI) m/z: [M+H]+=714.45.

Example 7. Preparation of 3-(5-[4-[2-(1-[[4-(1,3-dimethyl-2-oxo-4H-pyrimidin-5-yl)-2,6-dimethoxy-phenyl]methyl]piperidin-4-yl)ethyl]piperazin-1-yl]-1-oxo-3H-isoindol-2-yl)piperidine-2,6-dione (Compound D2)

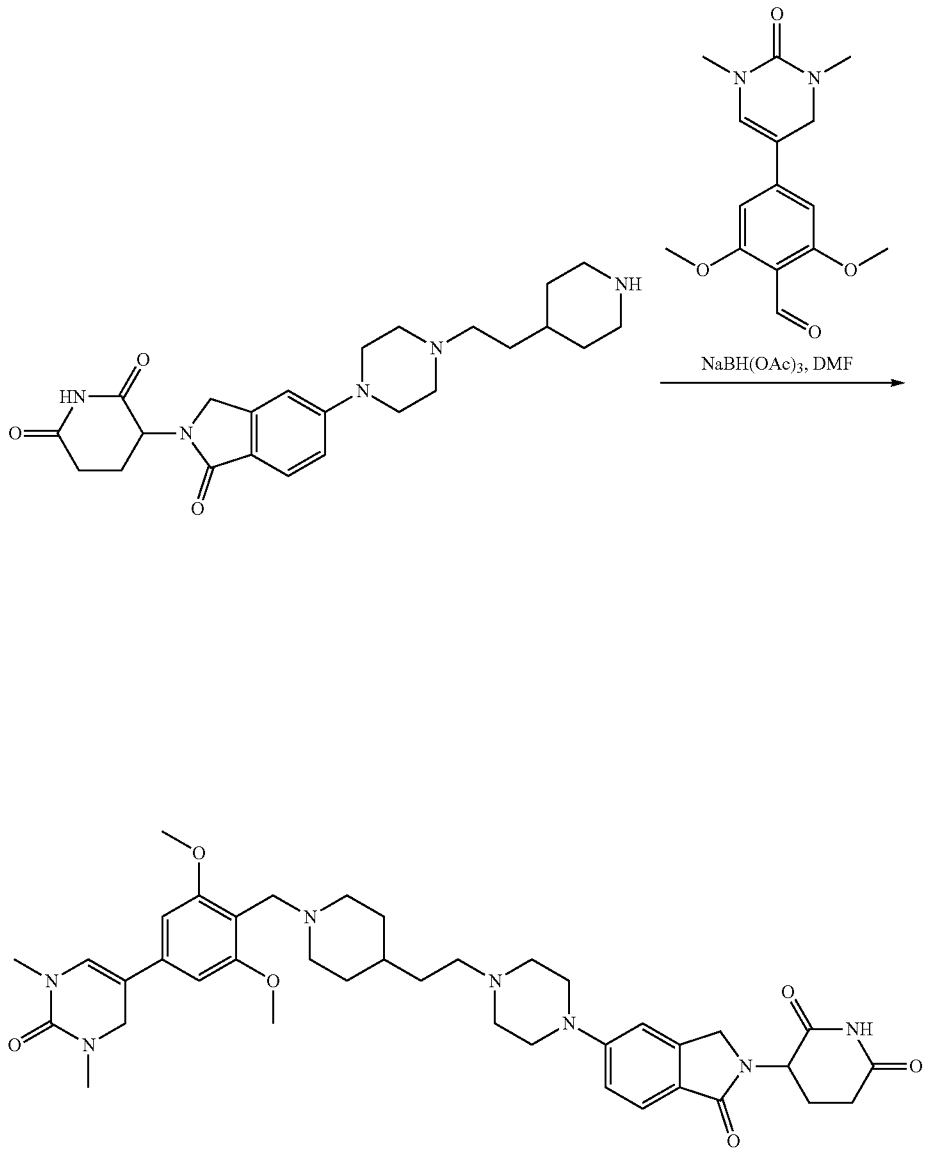

To a stirred solution of 3-(1-oxo-5-[4-[2-(piperidin-4-yl)ethyl]piperazin-1-yl]-3H-isoindol-2-yl)piperidine-2,6-dione (100.00 mg, 0.228 mmol, 1.00 equivalent) and 4-(1,3-dimethyl-2-oxo-4H-pyrimidin-5-yl)-2,6-dimethoxybenzaldehyde (66.05 mg, 0.228 mmol, 1.00 equivalent) in DMF (3.00 mL) was added $NaBH(OAc)_3$ (144.65 mg, 0.683 mmol, 3.00 equivalent) at room temperature under nitrogen atmosphere. The resulting mixture was stirred for overnight at room temperature. The mixture solution was purified by Prep-HPLC with the following conditions (Column: Xcelect CSH F-pheny OBD Column, 19*250 mm, 5 μm; Mobile Phase A: Water (0.05% TFA), Mobile Phase B: ACN; Flow rate: 25 mL/min; Gradient: 12 B to 28 B in 12 min; 254/220 nm; $R_{T1}$: 10.80) to afford 3-(5-[4-[2-(1-[[4-(1,3-dimethyl-2-oxo-4H-pyrimidin-5-yl)-2,6-dimethoxyphenyl]methyl]piperidin-4-yl)ethyl]piperazin-1-yl]-1-oxo-3H-isoindol-2-yl)piperidine-2,6-dione (42 mg, 19.91%) as a light yellow solid. $^1$H NMR (400 MHz, DMSO-d6) δ 10.97 (s, 1H), 7.61 (dd, J=8.4, 5.0 Hz, 1H), 7.23-7.10 (m, 3H), 6.67 (d, J=1.9 Hz, 2H), 5.07 (dd, J=13.3, 5.1 Hz, 1H), 4.36 (d, J=17.1 Hz, 1H), 4.31-4.19 (m, 3H), 4.14 (d, J=4.3 Hz, 2H), 4.04 (d, J=10.3 Hz, 2H), 3.95 (d, J=3.1 Hz, 1H), 3.88 (d, J=3.0 Hz, 6H), 3.83 (s, 1H), 3.37 (d, J=12.2 Hz, 3H), 3.15 (d, J=15.6 Hz, 6H), 3.09 (s, 3H), 3.03-2.92 (m, 2H), 2.91 (s, 4H), 2.60 (d, J=17.3 Hz, 1H), 2.39 (dd, J=13.2, 4.7 Hz, 1H), 2.01-1.93 (m, 1H), 1.84 (d, J=13.4 Hz, 2H), 1.64-1.58 (m, 3H), 1.44 (t, J=12.5 Hz, 2H). LCMS (ESI) m/z: [M+H]+=714.20.

Example 8. Preparation of 3-(5-[4-[2-(4-[[4-(1,3-dimethyl-2-oxo-4H-pyrimidin-5-yl)-2,6-dimethoxy-phenyl]methyl] piperazin-1-yl)ethyl]piperidin-1-yl]-1-oxo-3H-isoindol-2-yl)piperidine-2,6-dione Formic Acid (Compound D3 Formic Acid)
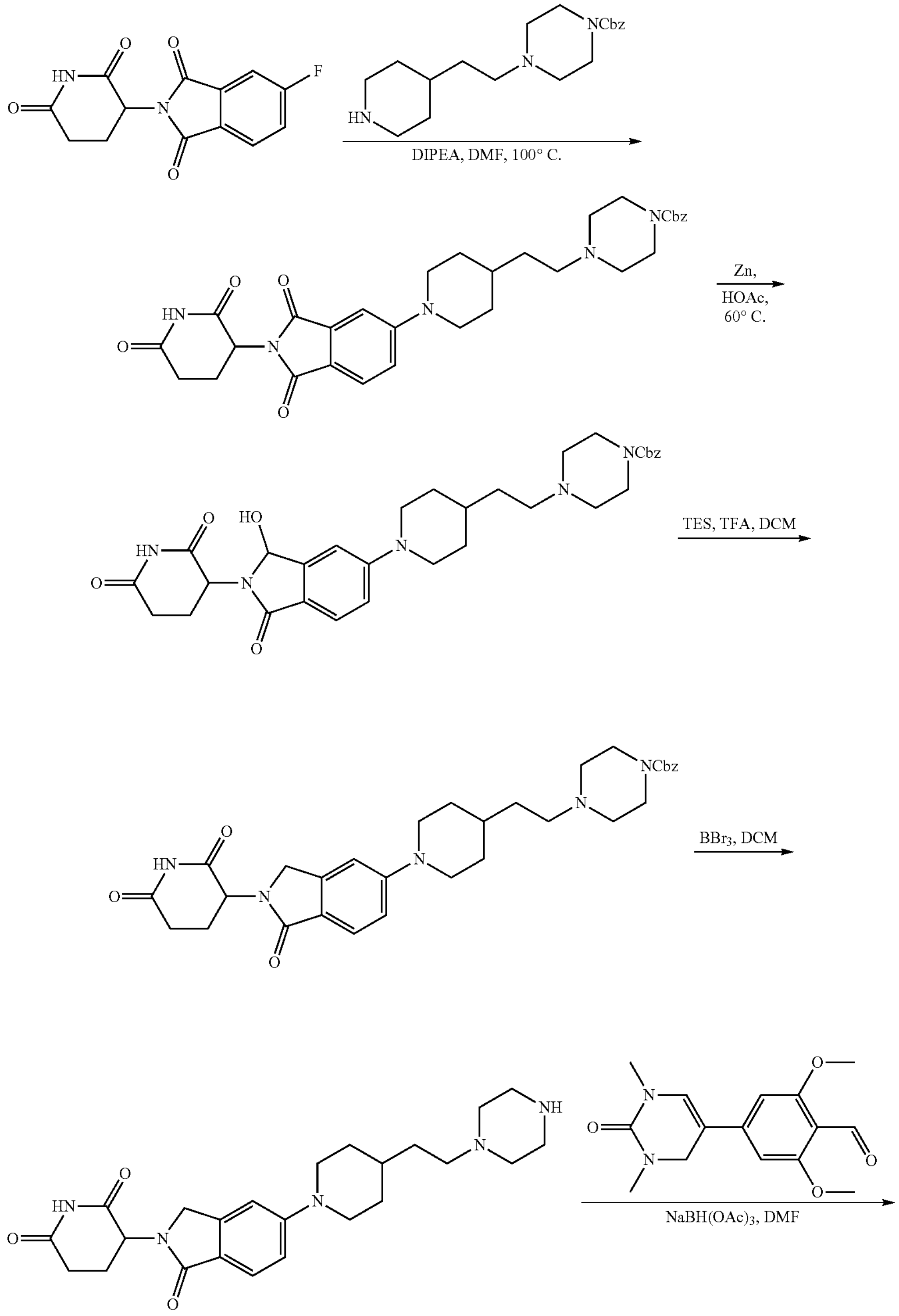

-continued

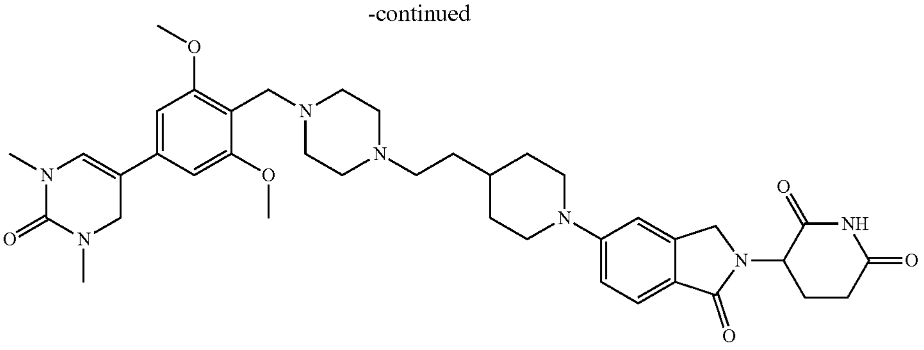

Step 1: Preparation of Benzyl 4-(2-[1-[2-(2,6-dioxopiperidin-3-yl)-1,3-dioxoisoindol-5-yl]piperidin-4-yl]ethyl)piperazine-1-carboxylate

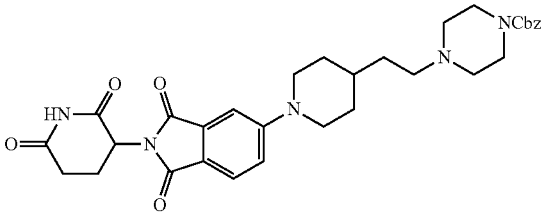 [SMILES: O=C1CCC(N2C(=O)c3ccc(N4CCC(CCN5CCN(C(=O)OCc6ccccc6)CC5)CC4)cc3C2=O)C(=O)N1]

To a stirred mixture of 2-(2,6-dioxopiperidin-3-yl)-5-fluoroisoindole-1,3-dione (1013.54 mg, 3.669 mmol, 1.00 equivalent) and benzyl 4-[2-(piperidin-4-yl)ethyl]piperazine-1-carboxylate hydrochloride (1350.00 mg, 3.669 mmol, 1.00 equivalent) in DMF (12 mL) was added DIPEA (1422.69 mg, 11.008 mmol, 3 equivalent) at room temperature under nitrogen atmosphere. The resulting mixture was stirred for 16 hours at 100° C. under nitrogen atmosphere. The mixture solution was purified by reverse phase flash with the following conditions (Mobile Phase A: Water (0.3% FA), Mobile Phase B: ACN; Flow rate: 80 mL/min; Gradient: 5% B to 20% B in 20 min)) to afford benzyl 4-(2-[1-[2-(2,6-dioxopiperidin-3-yl)-1,3-dioxoisoindol-5-yl]piperidin-4-yl]ethyl)piperazine-1-carboxylate (1300 mg, 54.26%) as a brown solid. LCMS (ESI) m/z: [M+H]+=588.

Step 2: Preparation of Benzyl 4-(2-[1-[2-(2,6-dioxopiperidin-3-yl)-3-hydroxy-1-oxo-3H-isoindol-5-yl]piperidin-4-yl]ethyl)piperazine-1-carboxylate

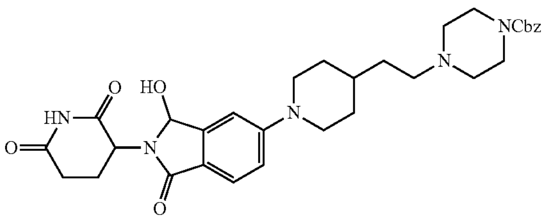 [SMILES: O=C1CCC(N2C(=O)c3ccc(N4CCC(CCN5CCN(C(=O)OCc6ccccc6)CC5)CC4)cc3C2O)C(=O)N1]

To a solution of Zn 1446.91 mg, 22.121 mmol, 10.00 equivalent) in Acetic Acid (10.00 mL) was added benzyl 4-(2-[1-[2-(2,6-dioxopiperidin-3-yl)-1,3-dioxoisoindol-5-yl]piperidin-4-yl]ethyl)piperazine-1-carboxylate (1300.00 mg, 2.212 mmol, 1.00 equivalent) at room temperature. The resulting mixture was stirred for 1 hour at 60° C. The resulting mixture was filtered, the filter cake was washed with ethyl acetate (2×10 mL). The filtrate was concentrated under reduced pressure. The residue was purified by reverse phase flash with the following conditions (Mobile Phase A: Water (0.3% FA), Mobile Phase B: ACN; Flow rate: 80 mL/min; Gradient: 5% B to 30% B in 50 minutes) to afford benzyl 4-(2-[1-[2-(2,6-dioxopiperidin-3-yl)-3-hydroxy-1-oxo-3H-isoindol-5-yl]piperidin-4-yl]ethyl)piperazine-1-carboxylate (1000 mg, 68.99%) as a yellow solid. LCMS (ESI) m/z: [M+H]+=590.

Step 3: Preparation of Benzyl 4-(2-[1-[2-(2,6-dioxopiperidin-3-yl)-1-oxo-3H-isoindol-5-yl]piperidin-4-yl]ethyl)piperazine-1-carboxylate

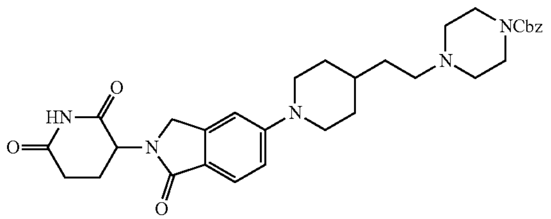 [SMILES: O=C1CCC(N2Cc3cc(N4CCC(CCN5CCN(C(=O)OCc6ccccc6)CC5)CC4)ccc3C2=O)C(=O)N1]

To a stirred solution of benzyl 4-(2-[1-[2-(2,6-dioxopiperidin-3-yl)-1-hydroxy-3-oxo-1H-isoindol-5-yl]piperidin-4-yl]ethyl)piperazine-1-carboxylate (1100.00 mg, 1.865 mmol, 1.00 equivalent) in DCM (15.00 mL) was added triethylsilane (3.00 mL) and TFA (3.00 mL) at room temperature. The resulting mixture was stirred for 3 hours at room temperature under nitrogen atmosphere. The mixture solution was concentrated under reduced pressure. The residue was purified by silica gel column chromatography, eluted with $CH_2Cl_2$/MeOH (30:1) to afford benzyl 4-(2-[1-[2-(2,6-dioxopiperidin-3-yl)-3-oxo-1H-isoindol-5-yl]piperidin-4-yl]ethyl)piperazine-1-carboxylate (1000 mg, 84.10%) as a white solid. LCMS (ESI) m/z: [M+H]+=574.

Step 4: Preparation of 3-(1-oxo-5-[4-[2-(piperazin-1-yl)ethyl]piperidin-1-yl]-3H-isoindol-2-yl)piperidine-2,6-dione

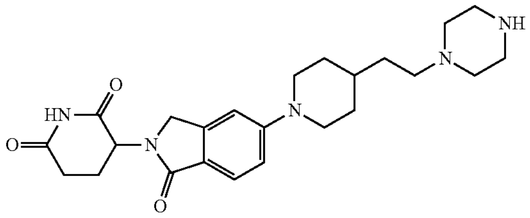 [SMILES: O=C1CCC(N2Cc3cc(N4CCC(CCN5CCNCC5)CC4)ccc3C2=O)C(=O)N1]

To a stirred solution of benzyl 4-(2-[1-[2-(2,6-dioxopiperidin-3-yl)-1-oxo-3H-isoindol-5-yl]piperidin-4-yl]ethyl) piperazine-1-carboxylate (1000.00 mg, 1.743 mmol, 1.00 equivalent) in DCM (100.00 mL) was added BBr3 (4366.84 mg, 17.431 mmol, 10 equivalent) dropwise at 0 degrees C. The resulting mixture was stirred for 1 hour at room temperature under nitrogen atmosphere. The mixture solution was purified by Prep-HPLC with the following conditions (Column: Atlantis Prep T3 OBD Column, 19*150 mm 5 μm; Mobile Phase A: Water (0.05% TFA), Mobile Phase B: ACN; Flow rate: 25 mL/min; Gradient: 4 B to 4 B in 2 min; 254/220 nm; $R_{T1}$: 6.02/7.57) to afford 3-(1-oxo-5-[4-[2-(piperazin-1-yl)ethyl]piperidin-1-yl]-3H-isoindol-2-yl)piperidine-2,6-dione (426 mg, 52.82%) as a brown oil. LCMS (ESI) m/z: [M+H]+=440.

Step 5: Preparation of 3-(5-[4-[2-(4-[[4-(1,3-dimethyl-2-oxo-4H-pyrimidin-5-yl)-2,6-dimethoxyphenyl]methyl]piperazin-1-yl)ethyl]piperidin-1-yl]-1-oxo-3H-isoindol-2-yl)piperidine-2,6-dione Formic Acid (Compound D3 Formic Acid)

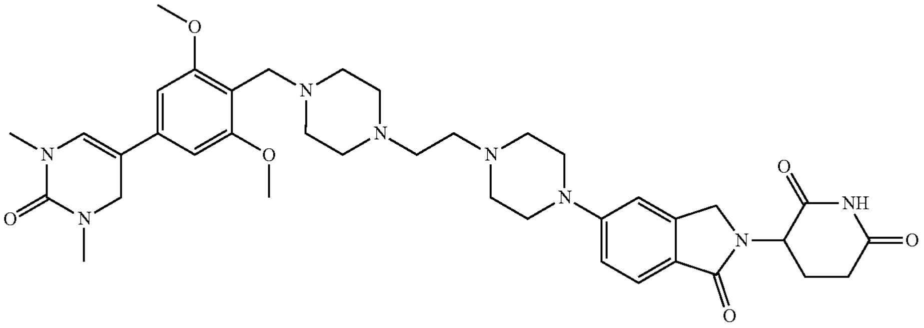 [SMILES: COc1cc(C2=CN(C)C(=O)N(C)C2)cc(OC)c1CN1CCN(CCN2CCN(c3ccc4c(c3)CN(C3CCC(=O)NC3=O)C4=O)CC2)CC1]

To a stirred mixture of 3-(1-oxo-5-[4-[2-(piperazin-1-yl) ethyl]piperidin-1-yl]-3H-isoindol-2-yl)piperidine-2,6-dione (100.00 mg, 0.228 mmol, 1.00 equivalent) and 4-(1,3-dimethyl-2-oxo-4H-pyrimidin-5-yl)-2,6-dimethoxybenzaldehyde (59.44 mg, 0.205 mmol, 0.90 equivalent) in DMF (2 mL) was added $NaBH(OAc)_3$ (96.43 mg, 0.455 mmol, 2 equivalent) at room temperature under nitrogen atmosphere. The resulting mixture was stirred for 2 h at room temperature under nitrogen atmosphere. The mixture solution was purified by Prep-HPLC with the following conditions (Column: XSelect CSH Prep C18 OBD Column, 19*250 mm, 5 μm; Mobile Phase A: Water (0.05% FA), Mobile Phase B: ACN; Flow rate: 25 mL/min; Gradient: 4 B to 28 B in 15 min; 254/220 nm; $R_{T1}$: 12.22) to afford 3-(5-[4-[2-(4-[[4-(1,3-dimethyl-2-oxo-4H-pyrimidin-5-yl)-2,6-dimethoxyphenyl]methyl]piperazin-1-yl)ethyl]piperidin-1-yl]-1-oxo-3H-isoindol-2-yl)piperidine-2,6-dione formic acid (25 mg, 15.37%) as a white solid. $^1H$ NMR (400 MHz, DMSO-d6) δ 10.95 (s, 1H), 8.19 (s, 1H, FA), 7.52-7.46 (m, 1H), 7.06-6.97 (m, 3H), 6.56 (s, 2H), 5.04 (dd, J=13.3, 5.1 Hz, 1H), 4.36-4.24 (m, 3H), 4.19 (d, J=16.8 Hz, 1H), 3.89-3.71 (m, 3H), 3.78 (s, 5H), 3.47 (s, 3H), 3.06 (s, 3H), 2.90 (s, 4H), 2.88-2.73 (m, 3H), 2.66-2.33 (m, 2H), 2.41-2.29 (m, 8H), 1.99-1.92 (m, 1H), 1.72 (d, J=12.5 Hz, 2H), 1.49 (s, 1H), 1.40-1.32 (m, 2H), 1.26-1.13 (m, 2H). LCMS (ESI) m/z: [M+H]+=714.45.

Example 9. SYO1 BRD9 NanoLuc Degradation Assay

This example demonstrates the ability of the compounds of the disclosure to degrade a Nanoluciferase-BRD9 fusion protein in a cell-based degradation assay.

Procedure: A stable SYO-1 cell line expressing 3×FLAG-NLuc-BRD9 was generated. On day 0 cells were seeded in 30 μL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 μM as final top dose). Subsequently plates were incubated for 6 hours in a standard tissue culture incubator and equilibrated at room temperature for 15 minutes. Nanoluciferase activity was measured by adding 15 μL of freshly prepared Nano-Glo Luciferase Assay Reagent (Promega N1130), shaking the plates for 10 minutes and reading the bioluminescence using an EnVision reader.

Results: The Inhibition % was calculated using the following formula: % Inhibition=100×($Lum_{HC}$−$Lum_{Sample}$)/($Lum_{HC}$−$Lum_{LC}$). DMSO treated cells are employed as High Control (HC) and 1 μM of a known BRD9 degrader standard treated cells are employed as Low Control (LC). The data was fit to a four parameter, non-linear curve fit to calculate $IC_{50}$ (μM) values as shown in Table 2. As shown by the results in Table 2, a number of compounds of the present disclosure exhibit an $IC_{50}$ value of <1 μM for the degradation of BRD9, indicating their use as compounds for reducing the levels and/or activity of BRD9 and their potential for treating BRD9-related disorders.

TABLE 2

| SYO1 BRD9-NanoLuc Degradation | |
|---|---|
| Compound No. | SYO1 BRD9-NanoLuc degradation $IC_{50}$(nM) |
| D1 | ++++ |
| D2 | ++++ |
| D3 | ++++ |

"+" indicates inhibitory effect of ≥1000 nM;
"++" indicates inhibitory effect of ≥100 nM;
"+++" indicatesinhibitory effect of ≥10 nM;
"++++" indicates inhibitory effect of <10 nM;
"NT" indicates not tested

OTHER EMBODIMENTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure of Formula I:

A-L-B    Formula I, wherein

B is a degradation moiety,

L is a linker, and

A has the structure of Formula II:

Formula II

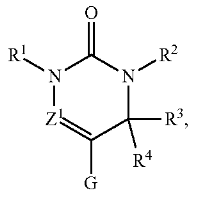

wherein the degradation moiety is a ubiquitin ligase binding moiety;

$R^1$ is, independently, H, optionally substituted $C_1$-$C_6$ alkyl, optionally substituted $C_1$-$C_6$ heteroalkyl, or optionally substituted $C_3$-$C_{10}$ carbocyclyl;

$Z^1$ is $CR^5$ or N;

$R^2$ is, independently, H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted sulfone, or optionally substituted sulfonamide, or $R^2$ and $R^3$ together with the atoms to which each is attached, form an optionally substituted $C_2$-$C_9$ heterocyclyl;

$R^3$ and $R^4$ are, independently, H, halogen, hydroxyl, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, thiol, optionally substituted sulfone, or optionally substituted amino, and/or $R^2$ and $R^3$ together with the atoms to which each is attached, form an optionally substituted $C_2$-$C_9$ heterocyclyl;

$R^5$ is H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl; and G is

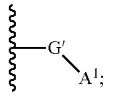

G' is optionally substituted $C_3$-$C_{10}$ carbocyclylene, $C_2$-$C_9$ heterocyclylene, optionally substituted $C_6$-$C_{10}$ arylene, or optionally substituted $C_2$-$C_9$ heteroarylene; and $A^1$ is a bond between A and the linker, or a pharmaceutically acceptable salt thereof.

2. The compound of claim 1, wherein $Z^1$ is $CR^5$.

3. The compound of claim 2, wherein $R^5$ is H.

4. The compound of claim 1, wherein $R^3$ and $R^4$ are both H.

5. The compound of claim 1, wherein $R^1$ is H, optionally substituted $C_1$-$C_6$ alkyl, or optionally substituted $C_3$-$C_{10}$ carbocyclyl.

6. The compound of claim 1, wherein $R^2$ is optionally substituted $C_1$-$C_6$ alkyl.

7. The compound of claim 1, wherein G' is optionally substituted $C_6$-$C_{10}$ aryl or optionally substituted $C_2$-$C_9$ heteroaryl.

8. The compound of claim 7, wherein G' is optionally substituted $C_6$-$C_{10}$ aryl.

9. The compound of claim 8, wherein G' is

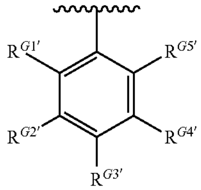

, each of $R^{G1'}$, $R^{G2'}$, $R^{G3'}$, $R^{G4'}$, and $R^{G5'}$is, independently, H, $A^1$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted -O-$C_3$-$C_6$ carbocyclyl, hydroxyl, thiol, or optionally substituted amino; or $R^{G1'}$ and $R^{G2'}$, $R^{G2'}$ and $R_{G3'}$, $R^{G3'}$ and $R^{G4'}$, or $R^{G4'}$ and $R^{G5'}$, together with the carbon atoms to which each is attached, combine to form

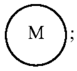;

and

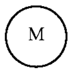

is optionally substituted $C_6$-$C_{10}$ aryl, optionally substituted $C_3$-$C_{10}$ carbocyclyl, optionally substituted $C_2$-$C_9$ heteroaryl, or optionally substituted $C_2$-$C_9$ heterocyclyl, any of which is optionally substituted with $A^1$, wherein one of $R^{G1'}$, $R^{G2'}$, $R^{G3'}$, $R^{G4'}$, and $R^{G5'}$ is $A^1$; or

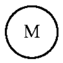

is substituted with $A^1$.

10. The compound of claim 9, wherein each of $R^{G1'}$, $R^{G2'}$, $R^{G3'}$, $R^{G4'}$, and $R^{G5'}$ is, independently, H, $A^1$, halogen, optionally substituted $C_1$-$C_6$ alkyl, optionally substituted $C_1$-$C_6$ heteroalkyl, or optionally substituted -O-$C_3$-$C_6$ carbocyclyl; or $R^{G1'}$ and $R^{G2}$, $R^{G2}$ and $R^{G3}$, $R^{G3}$ and $R^{G4}$, and/or $R^{G4}$ and $R^{G5}$ together with the carbon atoms to which each is attached, combine to form

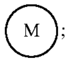;

and

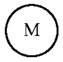

is optionally substituted $C_2$-$C_9$ heteroaryl or optionally substituted $C_2$-$C_9$ heterocyclyl, any of which is optionally substituted with $A^1$.

11. The compound of claim 10, wherein each of $R^{G1'}$, $R^{G2'}$, $R^{G3'}$, $R^{G4'}$, and $R^{G5'}$ is, independently, H, $A^1$, F, Cl,

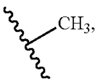 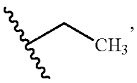, 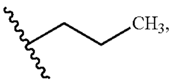

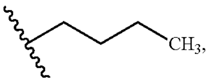 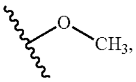 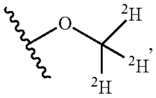,

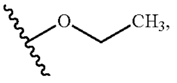 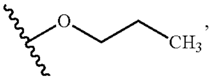,

-continued

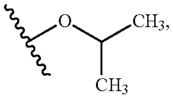 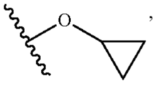, 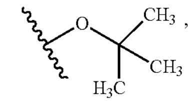

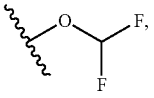 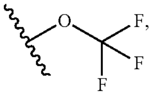 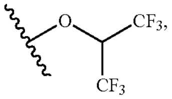

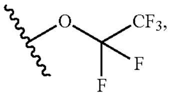 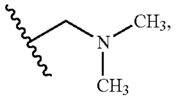 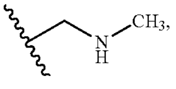

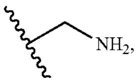 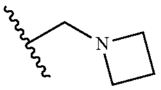, 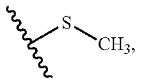 or

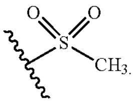

12. The compound of claim 9, wherein A has the structure of Formula IIa:

Formula IIa

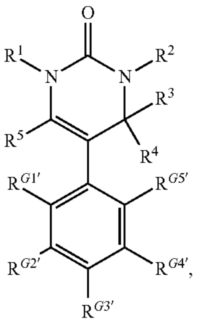

or a pharmaceutically acceptable salt thereof.

13. The compound of claim 12, wherein A has the structure of Formula IIb:

Formula IIIb

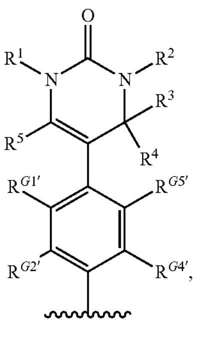

or a pharmaceutically acceptable salt thereof.

14. The compound of claim 13, wherein A has the structure of Formula IIc:

Formula IIc

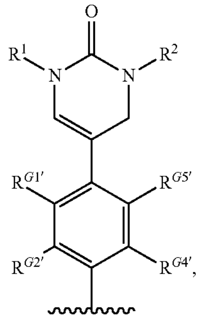

or a pharmaceutically acceptable salt thereof.

15. The compound of claim 1, wherein the ubiquitin ligase binding moiety comprises Cereblon ligands, IAP (Inhibitors of Apoptosis) ligands, mouse double minute 2 homolog (MDM2), or von Hippel-Lindau (VHL) ligands, or derivatives or analogs thereof.

16. The compound of claim 1, wherein the degradation moiety comprises the structure of Formula A:

Formula A

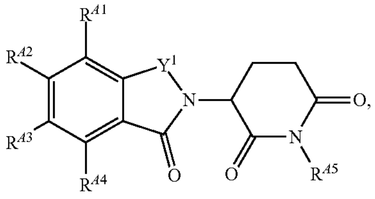

wherein $Y^1$ is

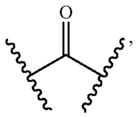, 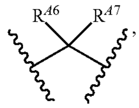, or 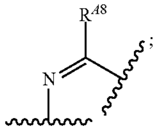;

$R^{A5}$ is H, optionally substituted $C_1$-$C_6$ alkyl, or optionally substituted $C_1$-$C_6$ heteroalkyl;

$R^{A6}$ is H or optionally substituted $C_1$-$C_6$ alkyl; and $R^{A7}$ is H or optionally substituted $C_1$-$C_6$ alkyl; or $R^{A6}$ and $R^{A7}$, together with the carbon atom to which each is bound, form an optionally substituted $C_3$-$C_6$ carbocyclyl or optionally substituted $C_2$-$C_5$ heterocyclyl; or $R^{A6}$ and $R^{A7}$, together with the carbon atom to which each is bound, form an optionally substituted $C_3$-$C_6$ carbocyclyl or optionally substituted $C_2$-$C_5$ heterocyclyl;

$R^{A8}$ is H, optionally substituted $C_1$-$C_6$ alkyl, or optionally substituted $C_1$-$C_6$ heteroalkyl;

each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted -O-$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

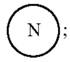;

and

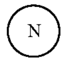

is optionally substituted $C_6$-$C_{10}$ aryl, optionally substituted $C_3$-$C_{10}$ carbocyclyl, optionally substituted $C_2$-$C_6$ heteroaryl, or $C_2$-$C_9$ heterocyclyl, any of which is optionally substituted with $A^2$, wherein one of $R^{A1}$, $R^{A2}$, $R^{A3}$, and $R^{A4}$ is $A^2$; or

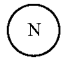

is substituted with $A^2$, or a pharmaceutically acceptable salt thereof.

17. The compound of claim 1, wherein the linker has the structure of Formula III:

$$A^1\text{-}(B^1)_f\text{-}(C^1)_g\text{-}(B^2)_h\text{-}(D)\text{-}(B^3)_i\text{-}(C^2)_j\text{-}(B^4)_k\text{-}A^2 \quad \text{Formula III}$$

wherein $A^1$ is a bond between the linker and A;

$A^2$ is a bond between B and the linker;

each of $B^1$, $B^2$, $B^3$, and $B^4$ is, independently, optionally substituted $C_1$-$C_2$ alkyl, optionally substituted $C_1$-$C_3$ heteroalkyl, O, S, S $(O)_2$, or $NR^N$;

each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

each of $C^1$ and $C^2$ is, independently, carbonyl, thiocarbonyl, sulphonyl, or phosphoryl;

each of f, g, h, i, j, and k is, independently, 0 or 1; and

D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$-$(C^1)_g$-$(B^2)_h$- to -$(B^3)_i$-$(C^2)_j$-$(B^4)_k$-$A^2$.

18. The compound of claim 1, wherein L has the structure of Formula IV:

$$A^1\text{-}(E^1)\text{-}(F^1)\text{-}(C^3)_m\text{-}(E^3)_n\text{-}(F^2)_{o1}\text{-}(F^3)_{o2}\text{-}(E^2)_p\text{-}A^2, \quad \text{Formula IV}$$

wherein $A^1$ is a bond between the linker and A;

$A^2$ is a bond between B and the linker;

each of m, n, o1, o2, and p is, independently, 0 or 1;

each of $E^1$ and $E^2$ is, independently, O, S, $NR^N$, optionally substituted $C_{1-10}$ alkyl, optionally substituted $C_{2-10}$ alkenyl, optionally substituted $C_{2-10}$ alkynyl, optionally substituted $C_2$-$C_{10}$ polyethylene glycol, or optionally substituted $C_{1-10}$ heteroalkyl;

$E^3$ is O, S, or $NR^N$;

each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

$C^3$ is carbonyl, thiocarbonyl, sulphonyl, or phosphoryl; and each of $F^1$, $F^2$, and $F^3$ is, independently, optionally substituted $C_3$-$C_{10}$ carbocyclyl, optionally substituted $C_{2-10}$ heterocyclyl, optionally substituted $C_6$-$C_{10}$ aryl, or optionally substituted $C_2$-$C_9$ heteroaryl.

19. The compound of claim 1, wherein the compound has the structure of:

| Compound No. | Structure |
|---|---|
| D1 | 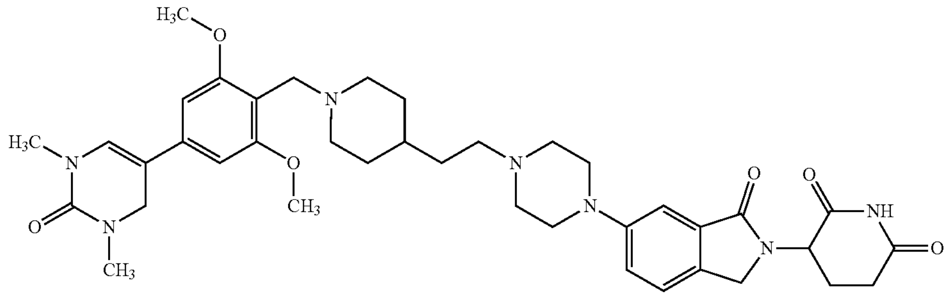 [SMILES: COc1cc(C2=CN(C)C(=O)N(C)C2)cc(OC)c1CN1CCC(CCN2CCN(c3ccc4c(c3)C(=O)N(C3CCC(=O)NC3=O)C4)CC2)CC1] |
| D2 | 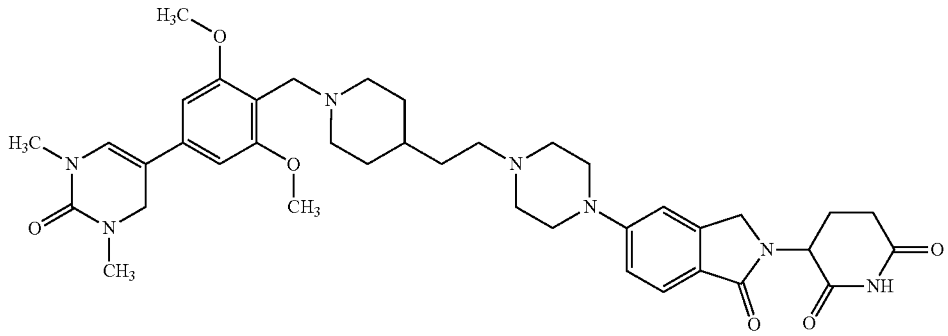 |
| D3 | 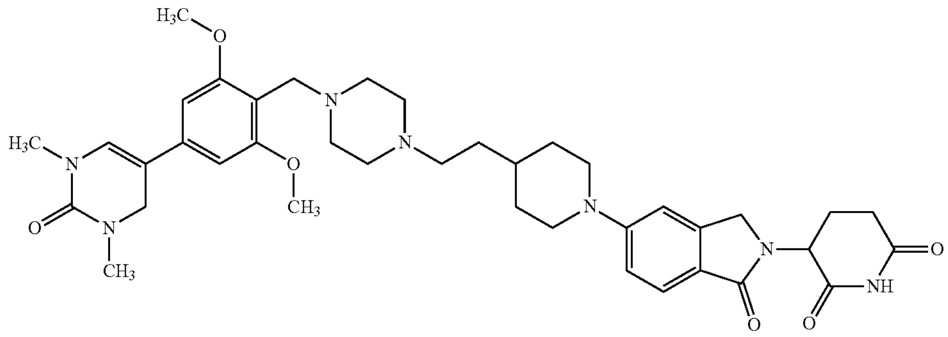 |

-continued
| Compound No. | Structure |
|---|---|
| D4 | 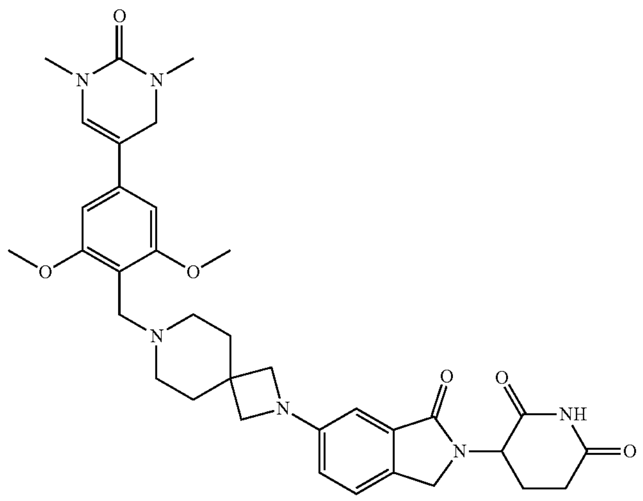 [SMILES: COc1cc(C2=CN(C)C(=O)N(C)C2)cc(OC)c1CN1CCC2(CC1)CN(c1ccc3c(c1)C(=O)N(C1CCC(=O)NC1=O)C3)C2] |
| D5 | 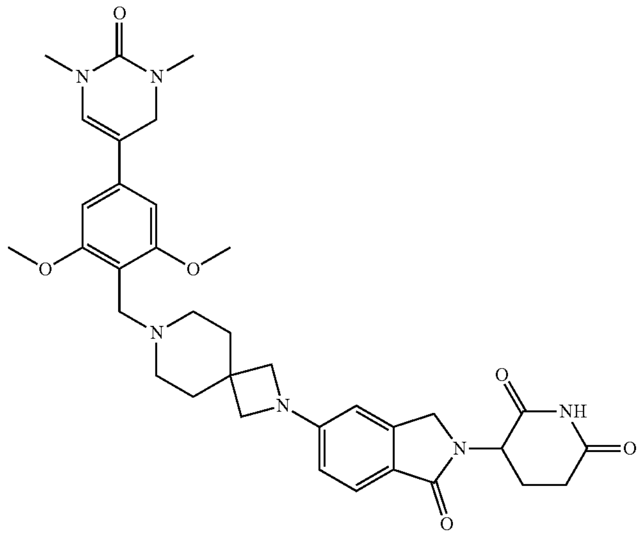 [SMILES: COc1cc(C2=CN(C)C(=O)N(C)C2)cc(OC)c1CN1CCC2(CC1)CN(c1ccc3c(c1)CN(C1CCC(=O)NC1=O)C3=O)C2] |
| D6 | 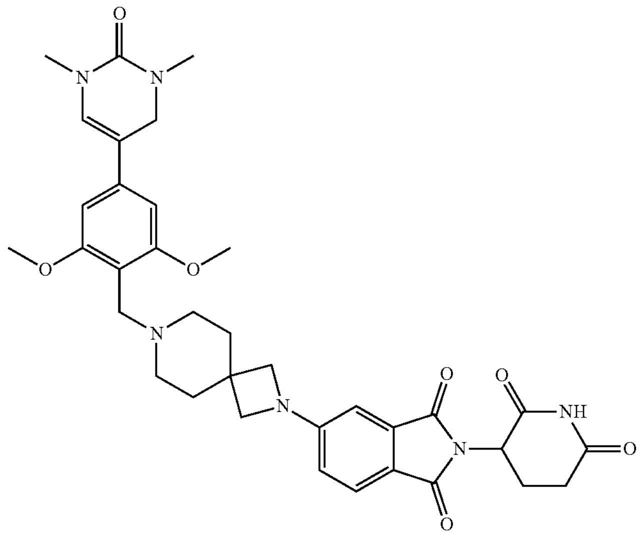 [SMILES: COc1cc(C2=CN(C)C(=O)N(C)C2)cc(OC)c1CN1CCC2(CC1)CN(c1ccc3c(c1)C(=O)N(C1CCC(=O)NC1=O)C3=O)C2] |

-continued
| Compound No. | Structure |
|---|---|
| D7 | 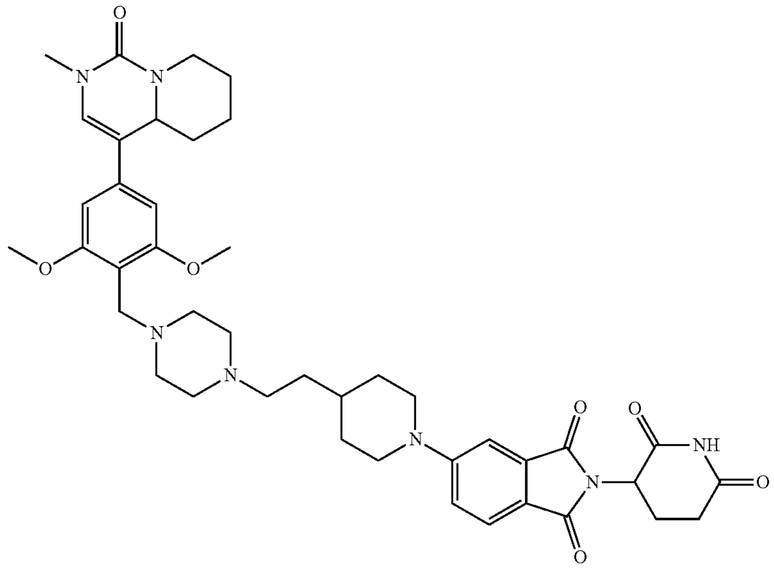 [SMILES: COc1cc(C2=CN(C)C(=O)N3CCCCC23)cc(OC)c1CN1CCN(CCC2CCN(c3ccc4c(c3)C(=O)N(C3CCC(=O)NC3=O)C4=O)CC2)CC1] |
| D8 | 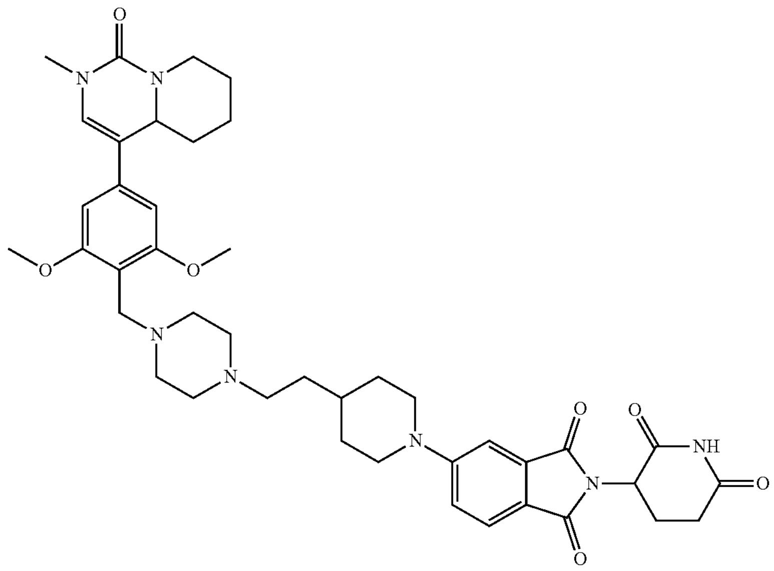 [SMILES: COc1cc(C2=CN(C)C(=O)N3CCCCC23)cc(OC)c1CN1CCN(CCC2CCN(c3ccc4c(c3)C(=O)N(C3CCC(=O)NC3=O)C4=O)CC2)CC1] |

-continued
| Compound No. | Structure |
| --- | --- |
| D9 | 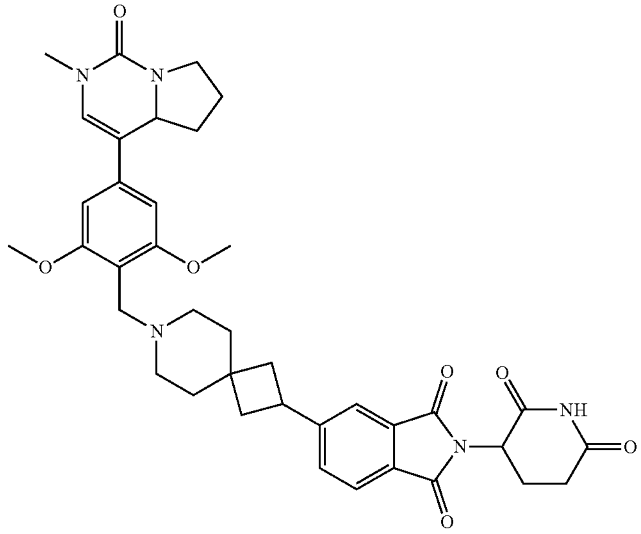 [SMILES: COc1cc(C2=CN(C)C(=O)N3CCCC23)cc(OC)c1CN1CCC2(CC1)CC(c1ccc3c(c1)C(=O)N(C1CCC(=O)NC1=O)C3=O)C2] |
| D10 | 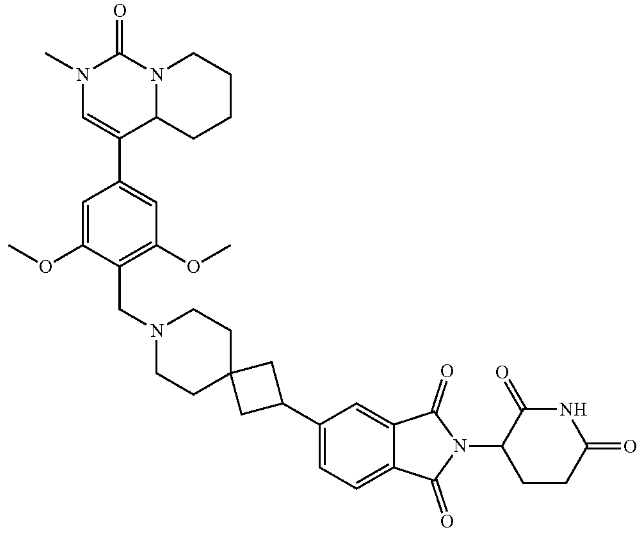 |

-continued
| Compound No. | Structure |
| --- | --- |
| D11 | 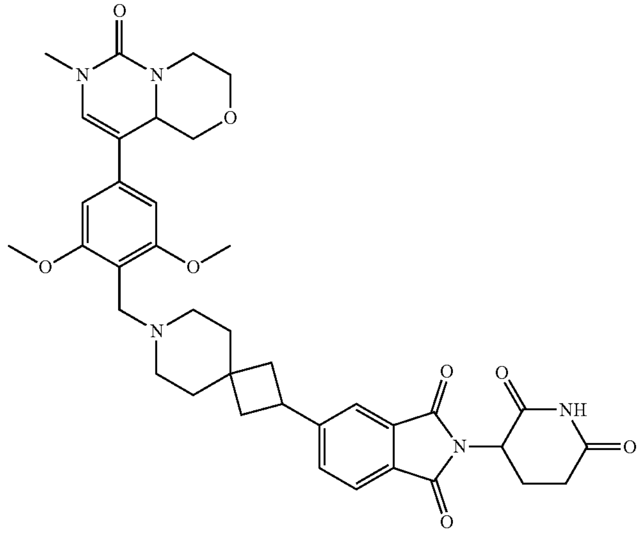 |
or a pharmaceutically acceptable salt thereof.
20. A method of treating a cancer in a subject in need thereof, the method including administering to the subject an effective amount of a compound of claim 1, or a pharmaceutically acceptable salt thereof.
* * * * *